(12) United States Patent
Sweigart et al.

(10) Patent No.: US 7,495,097 B2
(45) Date of Patent: Feb. 24, 2009

(54) RHODIUM QUINONOID CATALYSTS

(75) Inventors: Dwight A. Sweigart, Pawtucket, RI (US); Seung Uk Son, Suwon (KR); Jeffrey A. Reingold, Smithtown, NY (US); William C. Trenkle, Cranson, RI (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 11/454,760

(22) Filed: Jun. 15, 2006

(65) Prior Publication Data
US 2007/0117981 A1 May 24, 2007

Related U.S. Application Data

(60) Provisional application No. 60/739,623, filed on Nov. 23, 2005, provisional application No. 60/740,723, filed on Nov. 30, 2005.

(51) Int. Cl.
*C07F 15/00* (2006.01)
*B01J 31/00* (2006.01)

(52) U.S. Cl. ............... 546/2; 556/7; 556/136; 552/293; 552/294; 502/153

(58) Field of Classification Search ............ 556/7, 556/136; 552/293, 294; 546/2; 502/153
See application file for complete search history.

(56) References Cited

U.S. PATENT DOCUMENTS 4,469,897 A 9/1984 Rivetti et al. ............... 568/650

5,278,305 A 1/1994 Kelsey ....................... 526/135

OTHER PUBLICATIONS

Aleksandrov et al., Journal of Organometallic Chemistry, vol. 25, pp. 243-247 (1970).*
Bodner et al., Journal of Organometallic Chemistry, vol. 88, pp. 391-396 (1975).*
Rouhi, A. Maureen, "Fine Chemicals", Sep. 6, 2004, pp. 1-11, Chemical & Engineering News, Internet Article: http://pubs.acs.org/cen/coverstory/8236/8236finechecmicals.html.
Moussa, J. et al., "$\eta^3$-Semiquinone Complexes and the Related $\eta^4$-Benzoquinone of (Pentamethycyclopentadienyl) rhodium and -iridium: Synthesis, Structures, Hydrogen Bonding, and Electrochemical Behavior", 2004, pp. 6231-6238, Organometallics, vol. 23, No. 26.
Moussa, J. et al., "Self-Assembly of I-D Coordination Polymers Using Organometallic Linkers and Exhibiting Argentophilic Interations $AG^1 \cdots AG^1$", 2005, pp. 3808-3810, Eur. J. Inorg. Chem.
Son, S. U. et al., "Organometallic crystal engineering of [(1,4- and 1,3-hydroquinone)Rh(P(OPh)$_3$)$_2$]BF$_4$ by charge assisted hydrogen bonding", 2006, pp. 708-710, Journal Royal Society of Chemistry.
Son, S. U. et al., "Organometallic crystal engineering of [(1,4- and 1,3-hydroquinone)Rh(P(OPh)$_3$)$_2$]BF$_4$ by charge assisted hydrogen bonding", 2005, 2 pages, Supplementary Material (ESI) for Chemical Communications.

(Continued)

*Primary Examiner*—Porfirio Nazario Gonzalez
(74) *Attorney, Agent, or Firm*—Harrington & Smith, PC

(57) ABSTRACT

In accordance with one aspect of the invention a rhodium quinonoid catalyst is disclosed.

29 Claims, 21 Drawing Sheets

OTHER PUBLICATIONS

Son, S. U. et al., "An Anionic Rhodium $\eta^4$-Quinonoid Complex as a Multifunctional Catalyst for the Arylation of Aldenhydes with Arylboronic Acids", 2005, vol. 127, No. 35, pp. 12238-12239, J. American Chemical Society.

Son, S. U. et al., "Lithium Alkoxide {$Li_4O_4$} Cubanes Bridged by Rhodium-Quinonoid Organometalloligands", 2005, pp. 7710-7715, Angew. Chem. Int. Ed.

Son, S. U. et al.,"$Rh^{-Li+}$", 2005, pp. SI 1-6, Angewandte Chemie, Supporting Information.

Son, S. U. et al., "An Anionic Rhodium $\eta^4$-Quinonoid Complex as a Multifunctional Catalyst for the Phenylation of Aldehydes with Phenylboronic Acid", 2005, pp. S1-S9, Angewandte Chemie, Supporting Information.

Carreira, Erick M., Abstract, "Axial-chiral 1-phthalazinylnaphthyl monophosphine ligands and their transition metal complexes as asymmetric addition, hydroboration, cyclization and substitution reaction catalysts for production of optically active compounds", Dec. 22, 2005, 2 pages.

Boaz, N. W., Abstract, "Preparation of phosphine aminophosphine cocatalysts", Jun. 14, 2005, 2 pages.

Boaz, N. W., Abstract, "Preparation of Phosphine-phosphoramidite compounds useful as cocatalysts", Jun. 14, 2005, 2 pages.

Batey, Robert A., Abstract, "Rhodium-catalyzed addition of alkenyl- and aryltrifluoroborates to aldehydes and enones", Apr. 7, 2001, 1 page.

Maeda, A., Abstract, "Preparation of branched polyenes as monomers for unsaturated polymers", Nov. 17, 1998, 2 pages.

Hara, Y. et al., Abstract, "The acyloxy conversion catalyst of the conjugated diene and the manufacturing method for the preparation of unsaturated glycol diester", Sep. 2, 1998, 2 pages.

Auvray, P., Abstract, "Rhodium-phosphine catalysts for hydrogenation and addition reactions", Mar. 18, 1992, 1 page.

Abstract, "Alkenylmalanic acid cyclic esters", (Mitsui Petrochemical Industries, Ltd., Japan), May 2, 1980, 1 page.

Pierpont, C. G. et al., "The Chemistry of Transition Metal Complexes Containing Catechol and Semiquinone Ligands", Prog. Inorg. Chem. 1994, vol. 41, pp. 331-443.

Ebadi, M. et al., "Ruthenium Complexes of Quinone Related Ligands: A Study of the Electrochemical Properties of 2-Aminothiophenolatobis(2,2'-Bipridine) Ruthenium (II)", pp. 467-474.

Huang, Y. et al., "Reactions of Quinones and Quinoid Molecules with the CP $Ru^+$ Fragment. Electron Redistribution and Transposition Reactions", Organometallics 1992, vol. 11, pp. 3031-3035.

Koelle, U. et al., "Complexation and aromatization of α, β-unsaturated cyclic ketones by $Ru(H_2O)^{2+}{}_6$ and $(Bz)Ru(H_2O)^{2+}{}_3$: molecular structure of ($\eta^6$-Tosylate) ($\eta^5$-hydroxycyclopentadienyl) Ru and of ($\eta^6$-Tosylate) ($\eta^6$-1,4-dihydroxy-2,3,5,6-tetrametheylbenzene) Ru", Journal of Organometallic Chemistry 490 1995, pp. 101-109.

Schumann, H. et al., "Synthesis and Reactivity of 1,2- and 1,4-Dihydroxyarene Complexes of Chromium Tricarbonyl", Polyhedron 1999, vol. 9, No. 14, pp. 1677-1681.

Sun, S. et al., "$\eta^6$-Hydroquinone and cathechol complexes of manganese tricarbonyl", Journal of Organometallic Chemistry 1996, vol. 512, pp. 257-259.

Le Bras, J. et al., "p-,o-$\eta^4$-Benzoquinone and the Related $\eta^6$-Hydroquinone, $\eta^6$-Catechol Complexes of Pentamethylcyclopentadienyliridium: Synthesis, Structures, and Reactivity", Organometallics 1998, vol. 17, pp. 1116-1121.

Oh, M. et al., "$\eta^5$-Semiquinone and $\eta^4$-Quinone Complexes of Manganese Tricarbonyl. Intermolecular Hydrogen Bonding in the Solid State and in Solution", Organometallics 2002, vol. 21, pp. 1290-1295.

Oh, M. et al., "Supramolecular Metal—Organometallic Coordination Networks Based on Quinonoid—Complexes", Accounts of Chemical Research 2004, vol. 37, No. 1, pp. 1-11.

Casey, C. P. et al., "Hydrogen Elimination from a Hydroxycyclopentadienyl Ruthenium (II) Hydride: Study of Hydrogen Activation in a Ligand- Metal Bifunctional Hydrogenation Catalyst", J. Am. Chem. Soc. 2005, vol. 127, pp. 3100-3109.

Mermerian, A. et al., "Catalytic Enantioselective Synthesis of Quaternary Stereocenters via Intermolecular C-Acylation of Silyl Ketene Acetals: Dual Activation of the Electrophile and the Nucleophile", J. Am. Chem. Soc. 2003, vol. 125, pp. 4050-4051.

Suzuki, A., "Organoborates in New Synthetic Reactions", Acc. Chem. Res. 1982, vol. 15, pp. 178-184.

Miyaura, N. et al., "Palladium-Catalyzed Cross-Coupling Reactions of Organoboron Compounds", Chem. Rev. 1995, vol. 95, pp. 2457-2483.

Sakai, M. et al., "Rhodium-Catalyzed Addition of Organoboronic Acids to Aldehydes", Angew. Chem. Int. Ed..1998, vol. 37, No. 23, pp. 3279-3281.

Ueda, M. et al., "A Large Accelerating Effect of Tri(tert-butyl)phosphine in the Rhodium-Catalyzed Addition of Arylboronic Acids to Aldehydes", J. Org. Chem. 2000, vol. 65, pp. 4450-4452.

Furstner, A. et al., "Practical Method for the Rhodium-Catalyzed Addition of Aryl- and Alkenylboronic Acids to Aldehydes", Adv. Synth. Catal. 2001, vol. 343, No. 4, pp. 343-350.

Pucheault, M. et al., "Direct Access to Ketones from Aldehydes via Rhodium-Catalyzed Cross-Coupling Reaction with Potassium Trifluoro(organo)borates", J. Am. Chem. Soc. 2004, vol. 126, pp. 15356-13537.

Takaya, Y. et al., "Rhodium-Catalyzed Asymmetric 1,4-Addition of Aryl- and Alkenylboronic Acids to Enones", J. Am. Chem. Soc. 1998, vol. 120, pp. 5579-5580.

Batey, R. A. et al., "Potassium Alkenyl- and Aryltrifluoroborates: Stable and Efficient Agents for Rhodium-Catalyzed Addition to Aldehydes and Enones", Organic Letters 1999, vol. 1, No. 10, pp. 1683-1686.

Ramnauth, J. et al., "Stereoselective C-Glycoside Formation by A Rhodium(I)-Catalyzed 1,4-Addition of Arylboronic Acids to Acetylated Enones Derived from Glycals", Organic Letters 2001, vol. 3, No. 16, pp. 2571-2573.

Kuriyama, M. et al., "Hemilabile Amidomonophosphine Ligand-Rhodium(I) Complex-Catalyzed Asymmetric 1,4-Addition of Arylboronic Acids to Cycloalkenones", J. Am. Chem. Soc. 2002, vol. 124, pp. 8932-8939.

Hayashi, T. et al., "Catalytic Cycle of Rhodium-Catalyzed Asymmetric 1,4-Addition of Organoboronic Acids. Arylrhodium, Oxa—allylrhodium, and Hydroxorhodium Intermediates", J. Am. Chem. Soc. 2002, vol. 124, pp. 5052-5058.

Yoshida, K. et al., " New Type of Catalytic Tandem 1,4-Addition-Aldol Reaction Which Proceeds through an (Oxa-π-allyl)rhodium Intermediate", J. Am. Chem. Soc. 2002, vol. 124, pp. 10984-10985.

Itooka, R. et al., "Rhodium-Catalyzed 1,4-Addition of Arylboronic Acids to a,β-Unsaturated Carbonyl Compounds: Large Accelerating Effects of Bases and Ligands", J. Org. Chem. 2003, vol. 68, pp. 6000-6004.

Duursma, A. et al., "Highly Enantioselective Conjugate Additions of Potassium Organotrifluoroborates to Enones by Use of Monodentate Phosphoramidite Ligands", J. Org. Chem. 2004, vol. 69, pp. 8045-8052.

Sammis, G. et al., "Cooperative Dual Catalysis: Application to the Highly Enantioselective ConjugateCyanation of Unsaturated Imides", J. Am. Chem. Soc. 2004, vol. 126, pp. 9928-9929.

Shibasaki. M. et al., "Lanthanide Complexes in Multifunctional Asymmetric Catalysis", Chem. Rev. 2002, vol. 102, pp. 2187-2209.

Yamagiwa, N. et al., "Heterobimetallic Catalysis in Asymmetric 1,4-Addition of O-Alkylhydroxylamine to Enones", J. Am. Chem. Soc. 2003, vol. 125, pp. 16178-16179.

Li, C. et al., "The $Rh_4(CO)_{12}$-Catalyzed Hydroformylation of 3,3-Dimethylbut-1-ene Promoted with $HMn(CO)_5$. Bimetallic Catalytic Binuclear Elimination as an Origin for Synergism in Homogenous Catalysis", J. Am. Chem. Soc. 2003, vol. 125, pp. 5540-5548.

Guo, N. et al., "Bimetallic Catalysis for Styrene Homopolymerization and Ethylene-Styrene Copolymerization. Exceptional Comonomer Selectivity and Insertion Regiochemistry", J. Am. Chem. Soc. 2004, vol. 126, pp. 6542-6543.

Comte, V. et al., "[TiPHOS(Rh)]$^+$: A Fortuitous Coordination Mode and an Effective Hydrosilylation Bimetallic Catalyst", Organometallics 2005, vol. 24, pp. 1439-1444.

Braga, A. C. et al., "Computational Characterization of the Role of the Base in the Suzuki-Miyaura Cross-Coupling Reaction", J. Am. Chem. Soc. 2005, vol. 127, pp. 9298-9307.

Noyori, R. et al., "Asymmetric Transfer Hydrogenation Catalyzed by Chiral Ruthenium Complexes", Acc. Chem. Res. 1997, vol. 30, pp. 97-102.

Josephson, N. S. et al., "Mechanism of Enantioselective Ti-Catalyzed Strecker Reaction: Peptide-Based Metal Complexes as Bifunctional Catalysts", J. Am. Chem. Soc. 2001, vol. 123, pp. 11594-11599.

Sakai, M. et al., "Rhodium-Catalyzed Conjugate Addition of Aryl- or I-Alkenylboronic Acids to Enones", Organometallics, vol. 16, No. 20, Sep. 30, 1997, pp. 4229-4231.

Fagnou, K. et al., "Rhodium-Catalyzed Carbon Carbon Bond Forming Reactions of Organometallic Compounds", Chem. Rev. 2003, vol. 103, pp. 169-196.

Hayashi, T. et al., "Rhodium-Catalyzed Asymmetric 1,4-Addition and Its Related Asymmetric Reactions", Chem. Rev. 2003, vol. 103, pp. 2829-2844.

Hayashi, T. "Rhodium-Catalyzed Asymmetric Addition of Aryl- and Alkenylboron Reagents to Electron-Deficient Olefins", Pure Appl. Chem. 2004, vol. 76, No. 3, pp. 465-475.

Chapman, C.J. et al., "Synthesis of Functionalised Phenylalanines Using Rhodium Catalysis in Water", Adv. Synth. Catal. 2003, vol. 345, No. 3, pp. 353-355.

Moss, R. J. et al., "Rhodium Catalysed Tandem Conjugate Addition-Protonation: An Enantioselective Synthesis of 2-Substituted Succinic Exters", Chem. Commun. 2004, pp. 1984-1985.

Paquin, J. et al., "Asymmetric Synthesis of 3,3-Diarylpropanals with Chiral Diene-Rhodium Catalyst", J. Am. Chem. Soc. 2005, vol. 127, pp. 10850-10851.

Son, S. U. et al., "An Anionic Rhodium $\eta^4$-Quinonoid Complex as a Multifunctional Catalysts for the Arylation of Aldehydes with Arylboronic Acids", J. Am. Chem. Soc. 2005, vol. 127, pp. 12238-12239.

Zou, G. et al., "Rhodium-Catalyzed Heck-Type Reaction of Arylboronic Acids With $\alpha,\beta$-hydrogen Elimination vs. Hydrolysis of Alkylrhodium Species", Chem. Commun. 2003, pp. 2438-2439.

Mori, A. et al., "Hydroxorhodium Complex-Catalyzed Carbon-Carbon Bond-Forming Reactions of Silanediols with $\alpha,\beta$-Unsaturated Carbonyl Compounds. Mizoroki-Heck-Type Reaction vs Conjugate Addition", J. Am. Chem. Soc. 2001, vol. 123, pp. 107774-10775.

Son, S. et al., "Charge-Assisted Hydrogen Bonding and Other Non-Covalent Interactions in the Self-Assembly of the Organometallic Building Block [($\eta^6$-Hydroquinone)Rh(P(OPh)$_3$)$_2$]$^+$ with a Range of Counteranions", Organometalics 2006, pp. 1-27.

Braga, D. et al., "Crystal Engineering and Organometallic Architecture", Chem. Rev. 1998, vol. 98, pp. 1375-1405.

Sun, S. et al., "Self-Assembly Organometallic Squares With Terpyridyl Metal Complexes as Bridging Ligands", Inorg. Chem. 2001, vol. 40, pp. 3154-3160.

Kuehl, C. J. et al., "Self-Assembly of Molecular Prisms via an Organometallic 'Clip'", Organic Letters 2002, vol. 4. No. 6, pp. 913-915.

Shin, D. M. et al., "Self-Assembly of Discrete Organometallic-Organic Hybrid Supramolecular Arrays from Ferrocenyl Dipyridines and Terephthalic and Trimesic Acids", Crystal Growth & Design 2002, vol. 2, No. 6, pp. 493-496.

Kim, Y. et al., "Organic-Organometallic Crystal Engineering: Novel Formation of a Honeycomb Supramolecular Architecture of [Re$_2$($\mu$-OMe)$_3$(CO)$_6$]$^-$ Anions Encapsulating a Linear H-Bonded Chain of [DABCO-H]$^+$ Cations", Inorganic Chemistry 2003, vol. 42, No. 14, pp. 4262-4264.

Hartnell, R. D. et al., "Peripherally $\eta^1$-Platinated Organometallic Porphyrins as Building Blocks for Multiporphyrin Arrays", Organometallics 2004, vol. 23, pp. 391-399.

Dong, Y. et al., "Organometallic Silver(I) Supramolecular Complexes Generated from Multidentate Furan-Containing Symmetric and Unsymmetric Fulvene Ligands and Silver(I) Salts", Inorg. Chem. 2005, vol. 44, pp. 1693-1703.

Eaton E. F. et al., "Control of Bulk Dipolar Alignment Using Guest-Host Inclusion Chemistry: New Materials for Second-Harmonic Generation", J. Am. Chem. Soc. 1987, vol. 109, pp. 1886-1888.

Lee, I. S. et al., "Organometallic-Organic Hybrid Crystals from Ferrocenyl Dipyridine and Binaphthol: Different Crystal Structures and Nonlinear Optical Properties Depending upon the Reaction Medium and Optical Purity of Binaphthol", Organometallics 1999, vol. 18, pp. 5080-5085.

Barlow, S. et al., "Electronic and Optical Properties of Conjugated Group 8 Metallocene Derivatives", Chem. Commun., 2000, pp. 1555-1562.

Albrecht, M. et al., "Organoplatinum Crystals for Gas-Triggered Switches", Nature, Aug. 31, 2000, vol. 406, pp. 970-974.

Albrecht, M. et al., "Platinum Group Organometallics Based on 'Pincer' Complexes: Sensors, Switches, and Catalysts", Angew. Chem. Int. Ed. 2001, vol. 40, pp. 3750-3781.

Dinolfo, P. H. et al., "Supramolecular Coordination Chemistry and Functional Microporous Molecular Materials", Chem. Mater. 2001, vol. 13, pp. 3113-3125.

Lee, S. J. et al., "The First Chiral Organometallic Triangle for Asymmetric Catalysis", J. Am. Chem. Soc. 2002, vol. 124, pp. 12948-12949.

Resendiz, M. J. et al., "A Self-Assembled Supramolecular Optical Sensor for Ni(II), Cd(II), and Cr(III)", Organic Letters 2004, vol. 6, No. 5, pp. 651-653.

Braga, D. et al., "Novel Organometallic Building Blocks for Crystal Engineering. Synthesis and Structural Characterization of the Dicarboxylic Acid [Cr$^0$($\eta^6$-C$_6$H$_5$COOH)$_2$], of Two Polymorphs of Its Oxidation Derivative [(Cr$^1$($\eta^6$-C$_6$H$_2$COOH)$_2$]+[PF$_6$]-, and of the Zwitterionic Form [Cr$^1$($\eta^6$-C$_6$H$_5$COOH)($\eta^{6-C}_6$H$_5$COO)]", Organometallics 2001, vol. 20, pp. 1875-1881.

Braga, D. et al., "Reversible Gas-Solid Reactions between the Organometallic Zwitterion [($\eta^5$-C$_5$H$_4$COOH) ($\eta^5$-C$_5$H$_4$COO)Co$^{III}$] and Vapors of Trifluoroacetic and Tetrafluoroboric Acids", Organometallics 2002, vol. 21, pp. 1315-1318.

Braga, D. et al., "Design, Synthesis, and Structural Characterization of Molecular and Supramolecular Heterobimetallic Metallamacrocycles Based on the 1,1'-Bis(4-pyridyl)ferrocence (Fe($\eta^5$-C$_5$H$_4$-I-C$_5$H$_4$N)$_2$) Ligand" Organometallics 2003, vol. 22, pp. 4532-4538.

Braga, D. et al., "Novel Organometallic Building Blocks for Molecular Crystal Engineering. 2. Synthesis and Characterization of Pyridyl and Pyrimidyl Derivatives of Diboronic Acid, [Fe($\eta^5$-C$_5$H$_4$-B(OH)$_2$)$_2$], and of Pyridyl Boronic Acid, [Fe($\eta^{5-C}_5$H$_4$-4-C$_5$H$_4$N)($\eta^5$-C$_5$H$_4$-B(OH)$_2$)]", Organometallics 2003, vol. 22, pp. 2142-2150.

Braga, D. et al., "Novel Organometallic Building Blocks for Molecular Crystal Engineering. 3. Synthesis, Characterization and Hydrogen Bonding of the Crystalline Mono- and Bis-Amide Derivatives of [CO$^{III}$($\eta^5$-C$_5$H$_4$-COOH)$_2$]$^+$and of the Cationic Zwitterion [Co$^{III}$($\eta^5$-C$_5$H$_4$CONHC$_5$H$_4$NH)($\eta^5$-C$_5$H$_4$COO)]$^{+}$", Crystal Growth & Design 2004, vol. 4, No. 4, pp. 769-774.

Braga, D. et al., "Intermolecular Interactions In Nonorganic Crystal Engineering", Acc. Chem. Res. 2000, vol. 33, pp. 601-608.

Xu, X. et al., "A Nanoporous Metal-Organic Framework Based on Bulky Phosphane Ligands", Angew. Chem. Int. Ed. 2002, vol. 41, No. 5, pp. 764-767.

Pschirer, N. G. et al., "Noninterpenetrating Square-Grid Coordination Polymers With Dimensions of 25 X 25 Å$^2$ Prepared by Using N,N$^1$-Type Ligands: The First Chiral Square-Grid Coordination Polymer", Agnew. Chem. Int. Ed. 2002, vol. 41, No. 4, pp. 583-585.

Moulton, B. et al., "Coordination Polymers: Toward Functional Transition Metal Sustained Materials and Supermoledules", Current Opinion in Solid State & Materials Science 2002, vol. 6, pp. 117-123.

Kannan, S. et al., "Reaction chemistry of [Pd$_2$($\mu$-OH)$_2$L$_4$]$^{2+}$ with aryl amines. Structures of [Pd$_2$($\mu$-OH){$\mu$-NH($\rho$-tol}(PPh$_3$)$_4$](BF$_4$)$_2$, [Pd($\eta^3$-CH$_2$C(NH($\rho$-tol)CH$_2$)(PPh$_3$)$_2$](BF$_4$), and [Pd(PMe$_2$Ph)$_2$($\mu$-PF$_2$O$_2$)]$_2$(PF$_6$)$_2$", Inorganica Chimica Acta 2003, vol. 345, pp. 8-14.

Son, S. et al., "Charge-Assisted Hydrogen Bonding and Other Non-Covalent Interactions in the Self-Assembly of the Organometallic Building Block [($\eta^6$-Hydroquinone)Rh(P(OPh)$_3$)$_2$]$^+$ with a Range of Counteranions", Organometallics 2006, pp. 1-27.

Kazarian, S. G. et al., "Is Intermolecular Hydrogen-Bonding to Uncharged Metal Centers of Organometallic Compounds Widespread in Solution ? A spectroscopic Investigation in Hydrocarbon, Noble Gas, and Supercritical Fluid Solutions of the Interaction between Fluoro Alcohols and ($\eta^5$-C$_5$R$_5$)ML$_2$ (R=H, Me; M=Co, Rh, Ir; L=CO, $C_2H_4$, $N_2$, $PMe_3$) and Its Relevance to Protonation", J. Am. Chem. Soc. 1993, vol. 115, pp. 9069-9079.

Iogansen, A. V. et al., "Hydrogen Bond Energy and Proton-Donating Ability of Fluorinated Alcohols", Translated from Zhurnal Prikl. Spektrosk., 1980, vol. 33, pp. 460-466.

Kesanli, B. et al., "Highly Interpenetrated Metal-Organic Frameworks for Hydrogen Storage", Angew. Chem. Int. Ed. 2005, vol. 44, pp. 72-75.

Lautens, Mark et al., "Rhodium-Catalyzed Heck-Type Coupling of Boronic Acids with Activated Alkenes in an Aqueous Emulsion", 2004, pp. 2006-2014, Synthesis 2004, No. 12.

Weiss, E., "Structures of Organo Alkali Metal Complexes and Related Compounds", Nov. 1993, pp. 1501-1670, Angew. Chem. Int. Ed. Engl. vol. 32, No. 11.

Beswick, M.A. et al., "Alkali Metals", 1994, pp. 1, Comprehensive Organometallic Chemistry II, vol. 1.

Williard, P. G. et al., "X-Ray Crystal Structure of a Lithium Aldolate-A Tetrameric Aggregate", 1985, pp. 3931-3934, Tetrahedron Letters, vol. 26, No. 33.

Gais, H. et al., "Isolation and X-ray Crystal Structure of the Tetrameric Lithium-Coordinated α-Sulfonimidoyl Carbanion [$Me_3Si$]CH{S(O)(NSiMe$_3$)}Li]$_4$: The First Structure of an α-SO Substituted Lithium Alkyl Having No External Donor Ligands", 1987, pp. 3775-3776, J. Am. Chem. Soc., vol. 109, No. 12.

Nichols, M.A. et al., "Chelation of-Substituted-1-lithoxides: Structural and Energetic Factors of Relevance to Synthetic Organic Chemistry", 1991, pp. 6222-6233, J. Am. Chem. Soc., vol. 113, No. 16.

Pospisil, P. J. et al., "A Substoichiometric Pyridine-Lithium Enolate Complex: Solution and X-ray Data and Implications for Catalysis in the Aldol Reaction", 1992, pp. 7585-7587, J. Am. Chem. Soc., vol. 114, No. 19.

Schutte, S. et al., "A stable aquo-complex of lithiated di-tert-butylfluorosilanol", 1993, pp. 45-49, Journal of Organometallic Chemistry, vol. 446.

Piarulli, U. et al., "Carbohydrate Metal Complexes as Ligands for Alkali Cations", 1994, pp. 1409-1410, J. Chem. Soc.

Apeloig, Y. et al., "Synthesis and the electronic spectra of the first β-ketoacylsilanes and their lithium enolates: new insights into hyperconjugation in acylsilanes and their anolates", 1995, pp. 73-82, Journal of Organometallic Chemistry, vol. 499.

Clegg, W. et al., "The synthesis and solid-state and solution structures of an unprecedented mixed chiral α-amino lithium alkoxide-lithium alkoxide aggregate", 1998, pp. 1323-1326, New J. Chem.

Armstong, D. R. et al., "Dynamic process in organolithium chemistry: tetrameric and 'open' tetrameric chiral α-amino lithium alkoxides", 1999, 7 pgs, New J.,Chem.

Hoskin, A. J. et al., "Decametylzirconocene-Chalcogenide-Hydride Complexes", 1999, pp. 2479-2483, Organometallics, vol. 18.

Jones, C. et al.,"Syntheses and structural studies of lithium complexes of 2-amino-6-methylpyridine", 2000, 5 pgs, J. Chem. Soc., Dalton Trans.

Strauch, J. et al., "Formation and structural properties of salicylaldiminato complexes of zirconium and titanium", 2000, pp. 810-821, Inorganica Chimica Acta 300-302.

Lorenz, V. et al., "ƒ-Element Disiloxanediolates: Novel Si-O-based Inorganic Heterocycles", 2001, pp. 848-857, Chem. Eur. Journal, vol. 7, No. 4.

Boyle, T. J. et al., "Structual Diversity of Lithium Neopentoxide Compounds", 2001, pp. 6281-6286, Inorg. Chem., vol. 40.

Seebach, D. et al., "Structures of Three Lithium Ester Enolates by X-ray Diffraction: Derivation of Reaction Path for Cleavage into Ketene and Alcoholate,"1985, pp. 5403-5409, J. Am Chem. Soc., vol. 107.

Jackman, L. M. et al., "Structural Factors Controlling the Aggregation of Lithium Phenolates in Weakly Polar Aprotic Solvents", 1988, pp. 3829-3835, J. Am. Chem. Soc., vol. 110.

Brehon, M. et al., "Structural studies of lithiated enaminones: the 1-oxa-5-azapenta-dienyllithium fluxional heterocubane [($Pr^iNCMeCHCMeOLi$)$_4$] and its dimeric hexamethylphosphoric triamide complex [{$Pr^iNCMeCHCMeOLi$-$OP(Nme_2)_3$}$_2$]", 1997, 5 pgs., J. Chem. Soc., Dalton Trans.

Clegg, W. et al., "Lithiated organophosphorus enamines: a new synthetic approach and the first crystal structures", 1999, 2 pgs., Chem. Comm.

Boyle, T. J. et al., "Structural Diversity in Solvated Lithium Aryloxides. Syntheses, Characterization, and Structures of [Li(Oar)(THF)$_x$ ]$_n$ and [Li(Oar)(py)$_x$ ]$_2$ Complexes Where Oar=$OC_6H_5$, $OC_6H_4$(2-Me), $OC_6H_3$(2,6-(Me))$_2$ , $OC_6H_4$(2-$Pr^i$), $OC_6H_4$(2-$Pr^1$), $OC_6H_3$(2,6-($Pr^1$))$_2$ $OC_6H_3$(2,6)-$Bu^i$))$_2$", 2000, pp. 5133-5146, Inorg. Chem. vol. 39.

Maetzke, T. et al., "X-ray Crystal Structure Analysis of an Octameric Lithium N-Isopropylbenzamide Aza Enolate Complex", 1990, pp. 3032-3037, Organometallics, vol. 9.

Ball, S. C. et al., "Dilithiated salen Complexes Chiral [(salen)Li2•hmpa]2 and Deliberate Partial hydrolysis to give [(salen)Li2]3•Li2O•2tmen•H2O [H2salen=N,N'-ethylenebis(salicyclideneimine); hmpa=hexamethylphosphoramide; tmen=tetramethylethylenediamine]", 1995, pp. 2147-2149, J. Chem. Soc., Chem. Comm.

Hyvärinen, K. et al., "Synthesis and Crystal Structure of a Novel Multiple Bridged Cubane Type (Li4O3Cl)3 Lithium Carbonato Chloro HMPA Siloxane Complex, [[Li$_4$($\mu_3$-Cl($\mu_6$-Osi(CH$_3$)$_2$O(CH$_3$)$_2$SiO)($\mu$-OP(N(CH$_3$)$_2$)$_3$)(OP(N(CH$_3$)$_2$)$_3$,]3($\mu_3$-Cl)($\mu_3$-C1)($\mu_9$-CO$_3$)]•2C$_4$H$_8$O", 1996, pp. 2171-2177, Polyhedron, vol. 15, No. 13.

Barnett, N. D. et al., "Butyllithium Cubane Tetramers Linked by Li-TMEDA-Li Bridges in an Infinite, Zig-Zag Chain Arrangement: First Crystallographic Study of a Simple Butyl Compound of an Early Main Group Element", 1993, pp. 1573-1574, J. Am. Chem. Soc., vol. 115.

Henderson, K. W. et al., "Rational Design of Molecular Sheets Composed of Interconnecting Eight- and Twenty-Four-Membered Rings: Use of Lithiated Aggregates To Control Network Assembly", 2003, pp. 2839-2841, Inorganic Chem. Comm., vol. 42.

MacDougall, D. J. et al., "Use of tetrameric cubane aggregates of lithium aryloxides as secondary building units in controlling network assembly", 2005, pp. 456-458, Chem. Commun.

Oh, M. et al., "Megal-Mediated Self-Assembly of π-Bonded Benzoquinone Complexes into Polymers with Tunable Geometries", 2001, pp. 3191-3194, Angew. Chem. Int. Ed., vol. 40, No. 17.

Oh, M. et al., "The $\eta^4$-o-Benzoquinone Manganese Tricarbonyl Anion (o-QMTC) as an Organometalloligand in the Formation of M(o-QMTC)$_2$(L-L) Complexes (M=Mn, Co, Cd; L-L=bipy, phen): Generation of Neutral 2-D Networks Containing Two Types of π-π Stacking", 2003, pp. 1437-1442, Organometallics, vol. 22.

Fairhurst, G. et al., "Cyclopentadienyl- or Pentamethylcyclopentadienyl-(arene)cobalt(III) Complexes: Arene—Indole, Benzene, Mesitylene, Hexamethylbenzene, 1,4-Dihydroxy- and 1-Hydroxy-4-methoxytetramethylbenzene", 1979, pp. 1531-1538, J. Chem. Soc.

Burrows, A.D. et al., "Multidemensional Crystal Engineering of Bifunctional Metal Complexes Containing Complementary Triple Hydrogen Bonds", 1995, pp. 329-339, Chem. Soc. Ref.

Spartan '04, Version 1.0.3; pp. 215-224, Wavefunction, Inc., Irvine, CA, W.J.A. Guide to Molecular Mechanics and Quantum Chemical Calculations, Chapter 16.

Braga, D. et al., "Polymorphism of Molecular Organometallic Crystals. A Third Form of the Supramolecular Hydrogen-Bonded Dimer {[Fe$_{11}$($\eta^5$-C$_5$H$_4$COOH)$_2$]}$_2$", 2004, pp. 1109-1112, Crystal Growth & Design, vol. 4, No. 6.

Whittall, I.R. et al., "Organometallic Complexes in Nonlinear Optics II . . . ," pp. 349-405, Adv. Organomet. Chem, vol. 43 (1999).

Lenaz G., Ed., Coenzyme Q: Biochemistry, Bioenergetics and Clinical Applications of Ubiquinone, 6 pages including title and table of contents, New York (1985).

* cited by examiner

| PRODUCT | BENZYLPROTON(ppm) | OTHER(ppm) | ARENE(ppm) | REF. |
|---|---|---|---|---|
| Ph-CH(OH)-Ph | 5.85(1H) | 2.20(OH,1H) | 7.48–7.05(10H) | 1 |
| Ph-CH(OH)-C6H4-OMe | 5.73(1H) | 3.74(Ome,3H) 2.51(OH,1H) | 7.30(5H) 7.22(2H),6.82(2H) | 1 |
| Ph-CH(OH)-(2,4,6-trimethylphenyl) | 6.32(1H) | 2.52(OH,1H) 2.28(3H) 2.23(6H) | 7.27–7.15(5H) 6.85(2H) | 2 |
| Ph-CH(OH)-C6H4-Me | 5.85(1H) | 2.56(OH,1H) 2.40(Me,3H) | 7.47–7.18(9H) | 1 |
| Ph-CH(OH)-C6H4-Cl | 5.60(1H) | 2.56(OH,1H) | 7.40–7.12(9H) | 1 |
| Ph-CH(OH)-C6H4-Ph | 5.73(1H) | 2.42(OH,1H) | 7.39–7.10(14H) | 2 |
| Ph-CH(OH)-C6H4-NO2 | 5.85(1H) | 2.66(OH,1H) | 8.00(2H),7.59(2H) 7.40(5H) | 3 |

1. Chen, D.-W.; Ochiai, M. *J Org Chem.* 1999, *64*, 6804.
2. Rudolf, J.; Schmidt, F.; Bolm, C. *Adv. Synth. Catal.* 2004, *346*, 867.
3. Strassolini, P.; Giumanini, A. G.; Verardo, G. *Tetrahedron* 1994, *50*, 217

FIG. 5

FIG.6  $[Li_4(OBu^t)_3(THF)_3(\eta^4-BENZOQUINONE)Rh(COD)]_2$

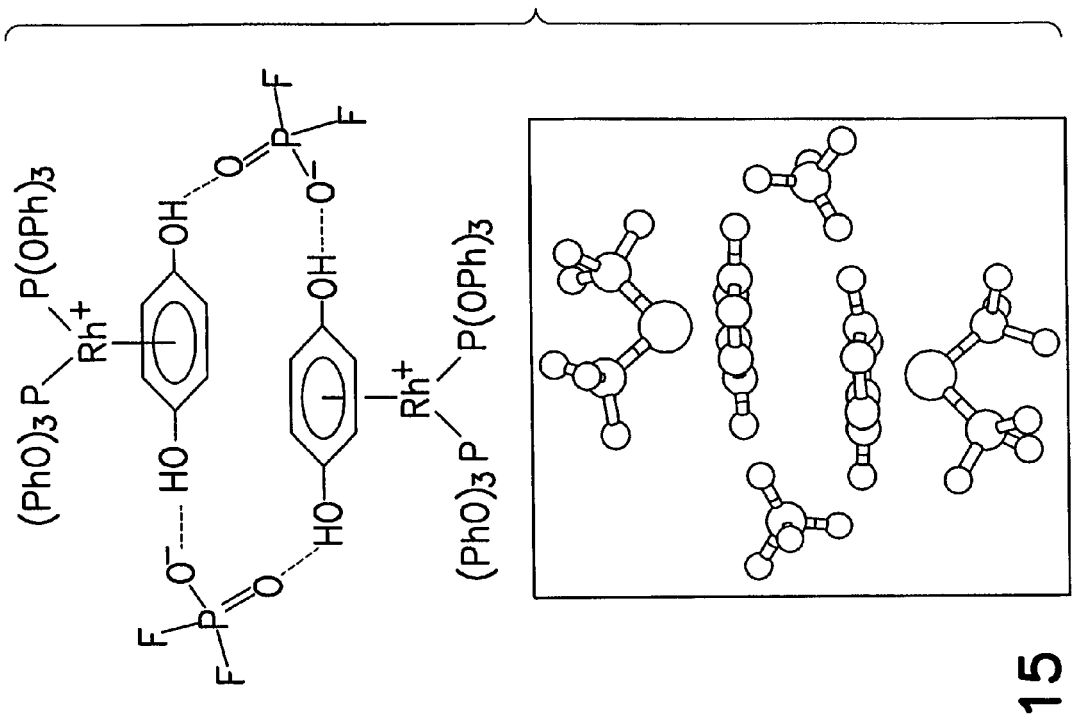
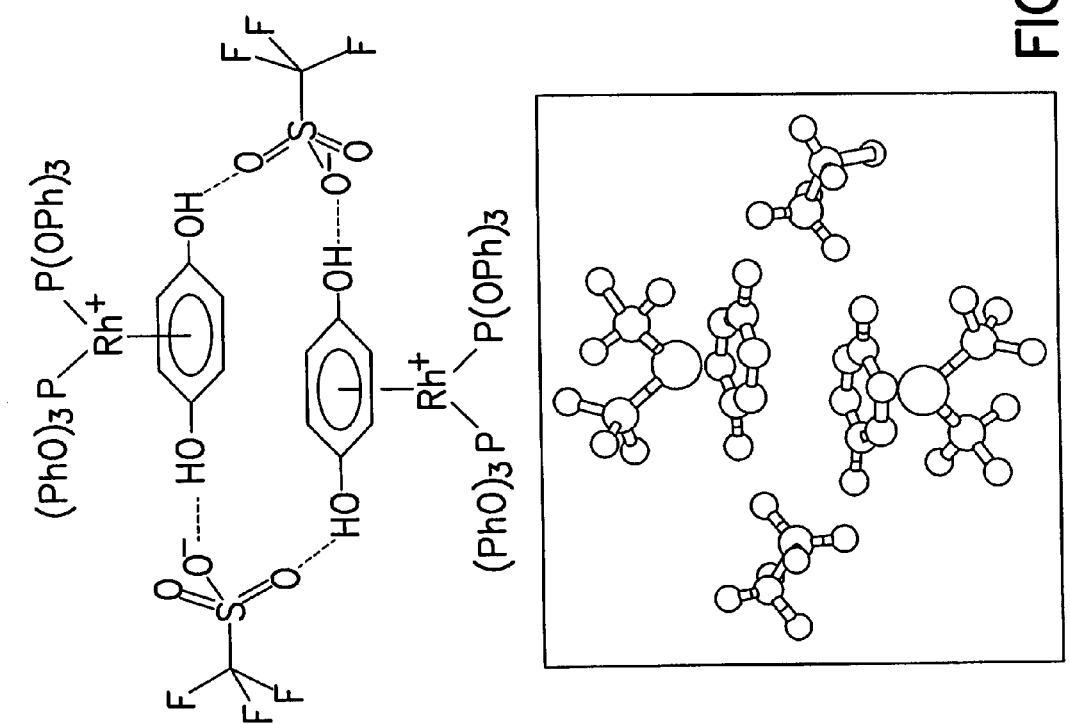
FIG.15

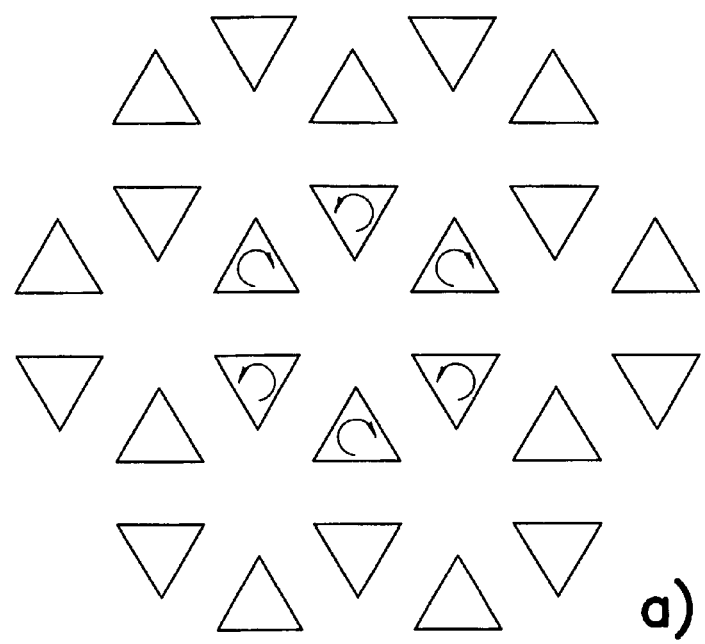
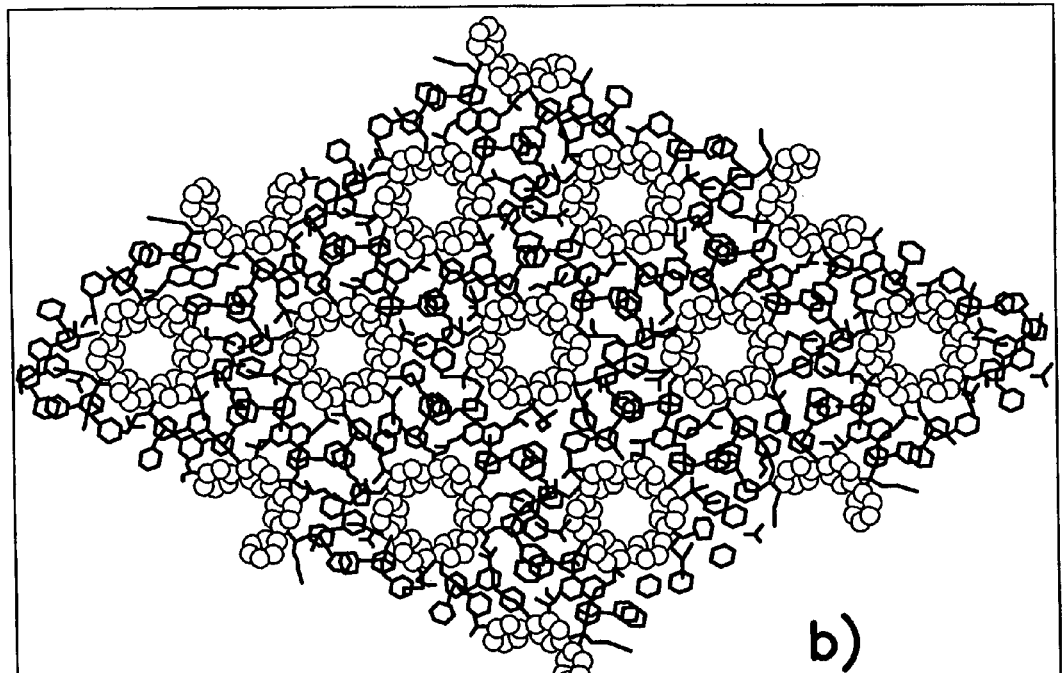
FIG. 20

RHODIUM QUINONOID CATALYSTS

PRIORITY CLAIM

This application claims priority from U.S. Provisional Patent Application No. 60/739,623 filed on Nov. 23, 2005 and U.S. Provisional Patent Application No. 60/740,723 filed on Nov. 30, 2005, the contents of each of which are hereby incorporated by reference in their entireties.

STATEMENT OF GOVERNMENT RIGHTS

The invention was made in part under U.S. Government contract number NSF CHE-0308640. Accordingly, the Government has certain rights in this invention.

RELATED APPLICATION

The subject application shares certain attributes with co-pending application Ser. No. 11/454,685, entitled, Method of Using Rhodium Quinonoid Catalysts, filed on even date herewith, the contents of which are hereby incorporated by reference in its entirety.

TECHNICAL FIELD

The invention concerns organometallic rhodium quinonoid compounds employed in chemical reactions.

BACKGROUND

Hydroquinones are of enormous fundamental importance in chemistry and biology. In spite of this importance, stable metal complexes containing a hydroquinone π-bonded to a metallic fragment are rare. Nevertheless, complexes containing 1,4-hydroquinone (H2Q)π-bonded to a transition metal are of great interest because of the importance of quinonoid molecules in mediating proton and electron transfer reactions. See: Pierpont, C. G.; Langi, C. W. *Prog. Inorg. Chem.* 1994, 41, 331. Ebadi, M.; Lever, A. B. P. *Inorg. Chem.* 1999, 38, 467. *Coenzyme Q: Biochemistry, Bioenergetics and Clinical Applications of Ubiquinone*; Lenaz, G., Ed.; Wiley: New York, 1985. Those skilled in the art desire new hydroquinone complexes having multifunctional applications. Embodiments of the subject invention satisfy this need and others.

SUMMARY OF THE INVENTION

The foregoing and other problems are overcome, and other advantages are realized, in accordance with embodiments of the invention.

In accordance with one aspect of the invention, a rhodium quinonoid catalyst or catalyst precursor is disclosed.

In accordance with another aspect of the invention disclosed is a rhodium quinonoid catalyst or catalyst precursor comprising the formula (I)

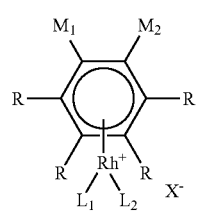
(I)

wherein $X^-$ is selected from the group consisting of $BF_4^-$, $SbF_6^-$, $PO_2F_2^-$, $PF_6^-$, $OTf^-$, $OTs^-$, $SO_4^{2-}$, $B(C_6F_5)_4^-$, $B(C_6H_5)_4^-$, $ClO_4^-$, $NO_3^-$, $NO_2^-$, $HOSO_3^-$, $CO_3^{2-}$; $O_3SCF_2CF_2CF_2CF_3^-$ wherein $OTf=O_3SCF_3^-$; $OTs=O_3SC_6H_4CH_3^-$; $R'CO_2^-$;

wherein R' is selected from the group consisting of hydrogen or an alkyl, aryl or carbon atom bearing three identical or non-identical substituents;

wherein $L_1$ and $L_2$ are each a ligand that donates electron density to rhodium to stabilize it; and may be identical or non-identical ligands that are either chiral or achiral and selected from the group consisting of alkenes, dialkenes, alkynes, phosphines, water, phosphates, sulfides, sulfoxides, sulfonates, sulfonamides, sulfones, ethers, amines, imines, amides, aldehydes, ketones, esters, nitriles and combinations thereof;

wherein

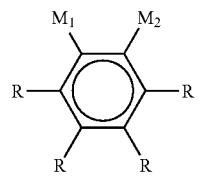

is either chiral or achiral and $M_1$ and $M_2$ comprise hydroxo (OH) groups in the ortho-, meta-, and para-positions and R is selected from the group consisting of H, C, O, N and S, with or without substituents, said substituents being identical or non-identical.

In accordance with a further aspect of the invention disclosed is a rhodium quinonoid catalyst or catalyst precursor comprising the formula (II)

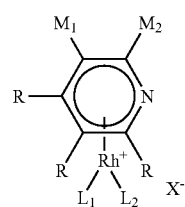
(II)

wherein $X^-$ is selected from the group consisting of $BF_4^-$, $SbF_6^-$, $PO_2F_2^-$, $PF_6^-$, $OTf^-$, $OTs^-$, $SO_4^{2-}$, $B(C_6F_5)_4^-$, $B(C_6H_5)_4^-$, $ClO_4^-$, $NO_3^-$, $NO_2^-$, $HOSO_3^-$, $CO_3^{2-}$, $O_3SCF_2CF_2CF_3$ wherein $OTf=O_3SCF_3^-$; $OTs=O_3SC_6H_4CH_3^-$; $R'CO_2^-$;

wherein R' is selected from the group consisting of hydrogen or an alkyl, aryl or carbon atom bearing three identical or non-identical substituents;

wherein $L_1$ and $L_2$ are each a ligand that donates electron density to rhodium to stabilize it; and may be identical or non-identical ligands that are either chiral or achiral and selected from the group consisting of alkenes, alkynes, phosphines, water, phosphates, sulfides, sulfoxides, sulfonates, sulfonamides, sulfones, ethers, amines, imines, amides, aldehydes, ketones, esters, nitriles and combinations thereof;

wherein R is selected from the group consisting of H, C, O, N and S, with or without substituents, said substituents being identical or non-identical.

In accordance with another aspect of the invention disclosed is a rhodium quinonoid catalyst or catalyst precursor comprising formula (III)

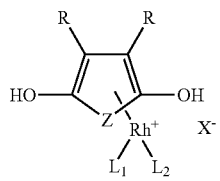

wherein Z is nitrogen, oxygen or sulfur;

wherein R is selected from the group consisting of H, C, O, N and S, with or without substituents, said substituents being identical or non-identical;

wherein $X^-$ is selected from the group consisting of $BF_4^-$, $SbF_6^-$, $PO_2F_2^-$, $PF_6^-$, $OTf^-$, $^-OTs$, $SO_4^{2-}$, $B(C_6F_5)_4^-$, $B(C_6H_5)_4^-$, $ClO_4^-$, $NO_3^-$, $NO_2^-$, $HOSO_3^-$, $CO_3^{2-}$, $O_3SCF_2CF_2CF_3^-$ wherein $OTf = O_3SCF_3^-$; $OTs = O_3SC_6H_4CH_3^-$; $R'CO_2^-$;

wherein R' is selected from the group consisting of hydrogen or an alkyl, aryl or carbon atom bearing three identical or non-identical substituents;

wherein $L_1$ and $L_2$ are each a ligand that donates electron density to rhodium to stabilize it; or formula (IV)

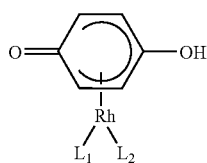

(IV)

wherein $L_1$ and $L_2$ are each a ligand that donates electron density to rhodium to stabilize it; or formula (V)

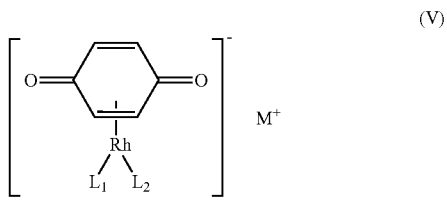

(V)

wherein $L_1$ and $L_2$ are each a ligand that donates electron density to rhodium to stabilize it; and wherein $M^+$ is a positively charged ion including any metal ion having an oxidation state at or higher than +1. $M^+$ may also be selected from the group consisting of cationic Li, K, Cs, Be, Sr, Ba, Al, Ti, Zr, B, Si, Cd, Ag, $Ph_3PNPPh_3$, Rb, $Mg^{2+}$, $Ca^{2+}$, Na, $R_4N^+$, $Zn^{2+}$, ammonium salts including tetraalkylammonium cations, tetraalkylarsonium cations, guanidinium salts, amidinium salts, other suitable counter-ions, and combinations thereof; and $L_1$ and $L_2$ may also be identical or non-identical ligands that are either chiral or achiral and selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitriles, other ligands, and combinations thereof.

In accordance with still further aspects of the invention disclosed is a catalyst or catalyst precursor comprising 1,3-hydroquinone π-bonded to rhodium, including $[1,3\text{-(hydroquine)}Rh(COD)]^+$ cations.

In accordance with other aspects of the invention disclosed is a catalyst or catalyst precursor comprising 1,2-hydroquinone, 1,3-hydroquinone or 1,4-hydroquinone π-bonded to $Rh(P(OPh)_3)_2^+$ cation.

Also disclosed in accordance with aspects of the invention is a porous organometallic structure comprising rhodium quinonoid salt $[1,4\text{-(hydroquine)}Rh(P(OPh)_3)_2]^+X^-$ ($X^- = BF_4^-$, $ClO_4^-$) and $[1,3\text{-(hydroquine)}Rh(P(OPh)_3)_2]^+$ $BF_4^-$, wherein the structure can be a porous media (i.e., one containing channels or pores of empty space) for gas storage, such as hydrogen gas storage.

Also disclosed in accordance with aspects of the invention is a catalyst or catalyst precursor, which is a multifunctional catalyst for the arylation of aldehydes with arylboronic acids and conjugate addition to activated carbon-carbon double bonds with arylboronic acids, wherein both the quinone and the rhodium participate in a catalytic reaction.

Further disclosed in accordance with aspects of the invention is a method comprising: a) mixing $[Rh(COD)Cl]_2$ and $AgBF_4$ in a solution of methylene chloride and acetone to form a precipitate; b) dissolving 1,4-hydroquinone in acetone and adding to a); c) followed by removing the solvent wherein a residue remained.

BRIEF DESCRIPTION OF THE DRAWINGS

The foregoing and other aspects of these teachings are made more evident in the following Detailed Description of the Preferred Embodiments, when read in conjunction with the attached Drawing Figures, wherein:

FIG. 5 shows $^1H$ NMR data of diaryl alcohols obtained using the rhodium quinonoid catalyst;

FIG. 15 shows dimeric structures of 14$^+$OTf$^-$ (left) and 14$^+$OPf$^-$, (right), both of which features charge assisted hydrogen bonding and π-π stacking interactions;

FIG. 20 shows (a) 3-D packing of the C$_3$ helices in 14$^+$ClO$_4^-$ and 14$^+$BF$_4^-$, and (b) a depiction of the resultant hydrophobic channels;

DETAILED DESCRIPTION

Non-limiting embodiments of the invention are further described below. However, it should be appreciated that some of the features of embodiments of the invention could be used to advantage without the corresponding use of other features. As such, the foregoing description should be considered as merely illustrative of the principles of the invention, and not in limitation thereof. Further, one skilled in the art will appreciate that the invention can be practiced by other than the described embodiments; that these described embodiments are presented for the purposes of illustration and not of limitation. For example, while various substituents are noted herein, other substituents known to those of skill in the art may also be employed in the compounds and formulas referenced herein.

By way of introduction, there is a great need for efficient catalysts in carbon-carbon coupling reactions of boronic acid derivatives (in general synthesis, pharmaceuticals, etc.) and for coupling monomers to give polymers. Due to the unique mechanism provided by the synergistic action of Applicants' rhodium and quinone components, the rhodium quinonoid catalysts promote reactions at a higher level of efficiency than previously available with non-quinone catalysts. This is further detailed in the sections below, which are set forth as I-IV for ease of reference.

It is also noted that the various publications that are cited in this document are incorporated by reference.

I. An Anionic Rhodium η$_4$-Quinonoid Complex as a Multifunctional Catalyst for the Arylation of Aldehydes with Arylboronic Acids Hydroquinone has been coordinated in a π-bonded η$^6$-manner to the metal fragments Cr(CO)$_3$, Mn(CO)$_3^+$, and Cp*M$^{2+}$ (M=Rh, Ir). See: Huang, Y.-S.; Sabo-Etienne, S.; He, X.-D.; Chaudret, B. *Organometallics* 1992, 11, 303. Koelle, U.; Weisschadel, C.; Englert, U. *J. Organomet. Chem.* 1995, 490, 101. Schumann, H.; Arif, A. M.; Richmond, T. G. *Polyhedron* 1990, 9, 1677. Sun, S.; Carpenter, G. B.; Sweigart, D. A. *J. Organomet. Chem.* 1996, 512, 257. Le Bras, J.; Amouri, H.; Vaissermann, *J. Organometallics* 1998, 17, 1116. Oh, M.; Carpenter, G. B.; Sweigart, D. A. *Organometallics* 2002, 21, 1290. Moussa, J.; Guyard-Duhayon, C.; Herson, P.; Amouri, H.; Rager, M. N.; Jutand, A. *Organometallics* 2004, 23, 6231. Fairhurst, G.; White, C. J. *Chem. Soc., Dalton Trans.* 1979, 1531. An important chemical property displayed by some of these complexes is facile deprotonation of the —OH groups, which is accompanied by electron transfer to the metal and changes in the hapticity of the quinonoid ring. See, e.g., Sun et al., and Oh et al. above.

Figure 1:
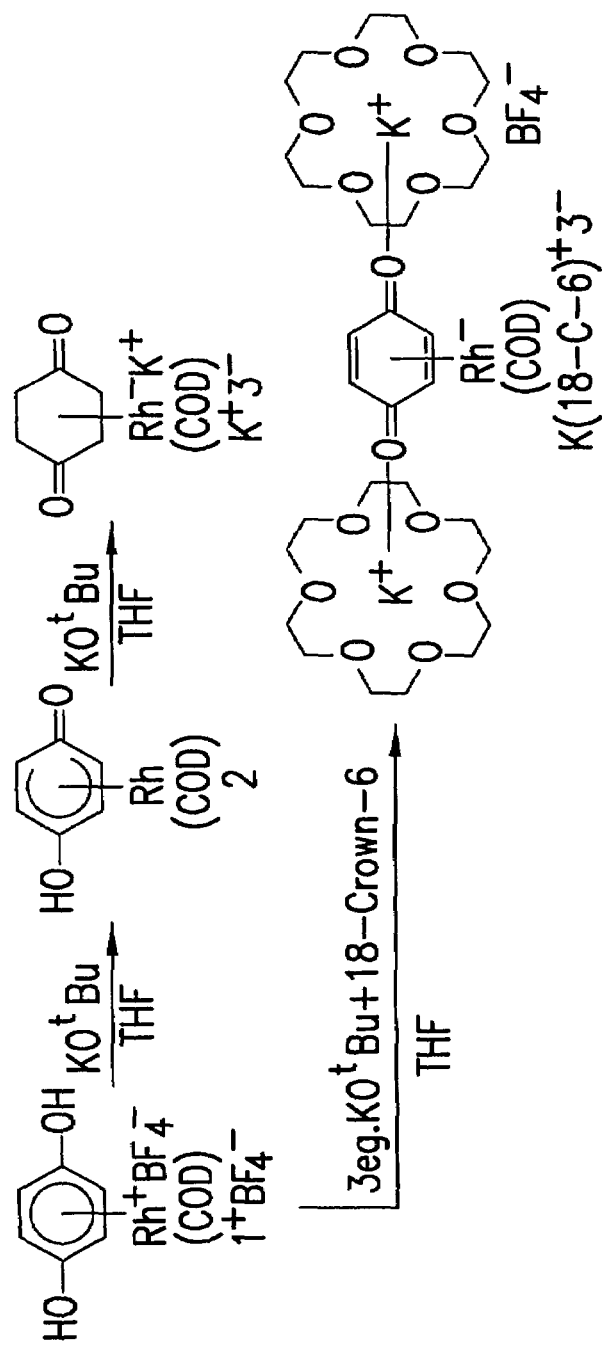
FIG. 1. shows deprotonation and concomitant oxidation of hydroquinonone to quinone with the π-bonded metal fragment acting as an internal electron acceptor.

The foregoing is illustrated in FIG. 1 for the new η$^6$-H$_2$Q complex [(1,4-hydroquinone)Rh(COD)]BF$_4$ (1$^+$BF$_4^-$), synthesized in 74% isolated yield by the reaction of [Rh(COD)Cl]$_2$ with AgBF$_4$ and H$_2$Q. 1$^+$BF$_4^-$ cleanly undergoes deprotonation to afford stable neutral semiquinone (2) and anionic quinone (3$^-$) complexes.

With a catalytically-active metal such as rhodium, it was thought that the ability to alter the charge on the metal center by simple reversible deprotonation at the quinonoid center may constitute a powerful way to tune catalytic activity. In addition, the anionic doubly deprotonated η$^4$-quinone complex 3$^-$ may be able to function as a ligand ("organometalloligand"), thereby offering the possibility of bifunctional activation of appropriate substrates by simultaneous interaction at the rhodium and quinonoid centers. The ability of a quinone complex to function as an organometalloligand has been demonstrated in the case of (η$^4$-benzoquinone)Mn(CO)$_3^-$. See: Oh, M.; Carpenter, G. B.; Sweigart, D. A., *Acc. Chem. Res.* 2004, 37, 1.

Figure 2:
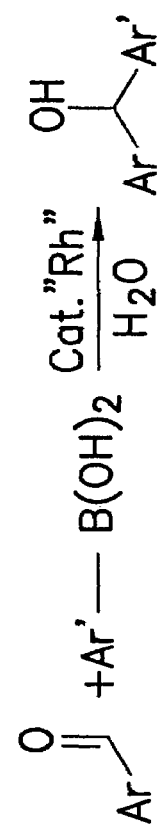
FIG. 2. shows catalytic arylation of benzaldehydes.

Catalysts able to operate in a bifunctional manner are of considerable current interest. See: Casey, C. P.; Johnson, J. B.; Singer, S. W.; Cui, Q. *J. Am. Chem. Soc.* 2001, 123, 11594. Mermerian, A. H.; Fu, G. C. *J. Am. Chem. Soc.* 2003, 125, 4050. Herein it is demonstrated that the hydroquinone complex 1$^+$BF$_4^-$ is a convenient precursor to M$^+$3$^-$, where M$^+$ can be any of a variety of cations such as an alkali metal or tetraalkylammonium cation, which serves as a catalyst for the coupling of arylboronic acids and benzaldehydes to produce diaryl alcohols (see FIG. 2). It is shown that M$^+$3$^-$ acts in a multifunctional manner by simultaneously activating both the boronic acid and the aldehyde, the former by coordination of a quinonoid oxygen in 3$^-$ to the boron and the latter through a Lewis acid interaction among the aldehyde, the counterion M$^+$ and a quinonoid oxygen.

Figure 3:
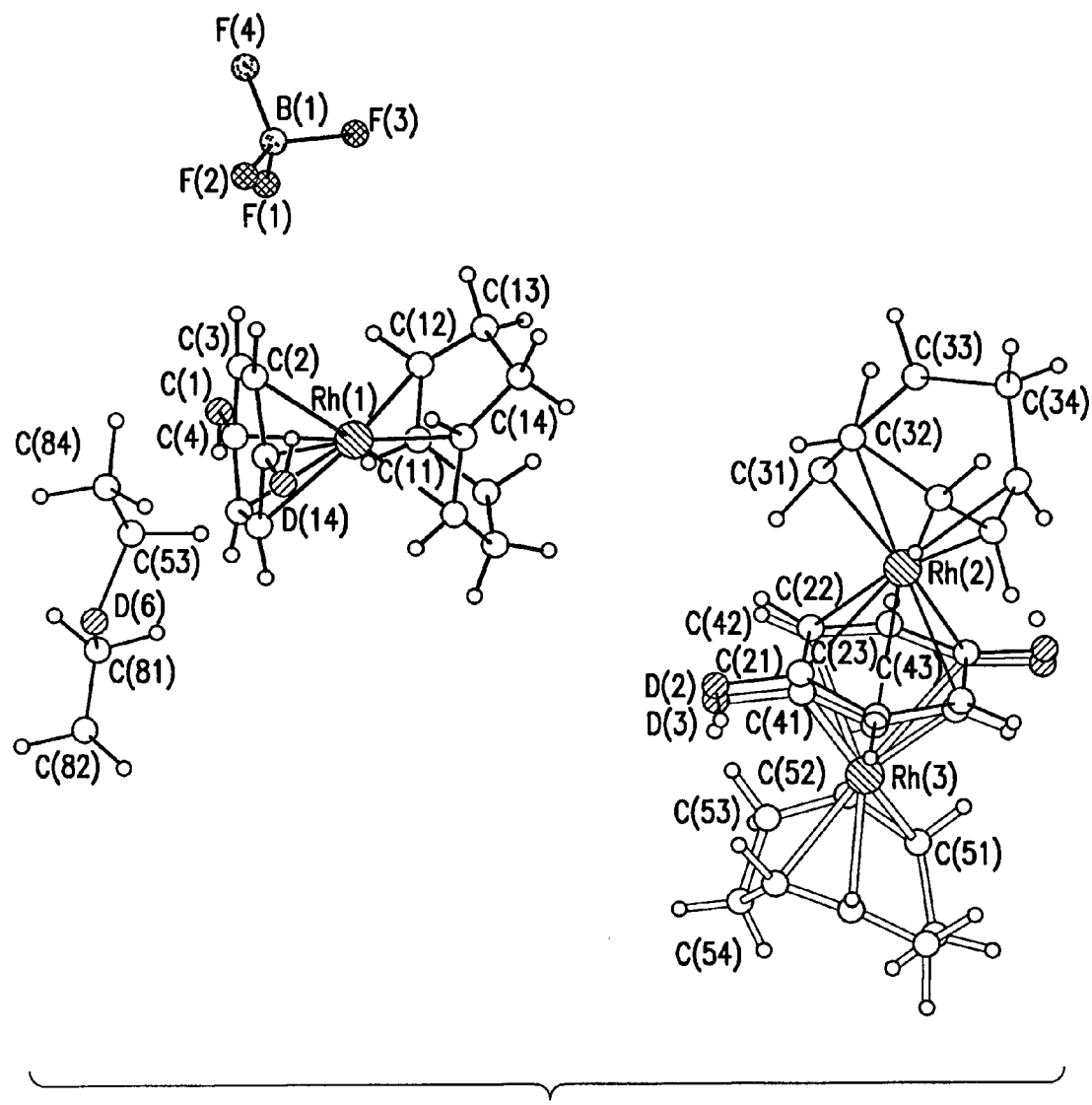
FIG. 3 shows the X-ray structure of $[(1,4\text{-hydroquinone}) Rh(COD)]BF_4$ or $1^+BF_4^-$, where "COD" is cyclooctadiene. There are three crystallographically independent Rh atoms, two of which show disorder, as shown at the right.

The X-ray structure of [(H$_2$Q)Rh(COD)]BF$_4$.Et$_2$O (1$^+$BF$_4^-$) established the anticipated η$^6$-bonding mode. The structure obtained from X-ray analysis is shown in FIG. 3. The solid state structure of 1$^+$BF$_4^-$ displays several types of crystallographic disorder, but the connectivity and chemical structure indicated is certain; the structure was solved to a acceptable R1 factor of 8.9%.

Deprotonation of 1$^+$BF$_4^-$ with KO$^t$Bu in THF (tetrahydrofuran) occurred readily to afford the semiquinone (2) and the quinone (K$^+$3$^-$) analogues (FIG. 1). X-ray quality crystals of K$^+$3$^-$ could not be grown, but the butylammonium salt was readily obtained by metathesis and its X-ray structure determined as Bu$_4$N$^+$[(1,4-Q)Rh(COD)]$^-$.3 Bu$_4$NBF$_4$. The Rh—C bond lengths clearly indicated an η$^1$-bonding mode, with the quinone Rh—C distances being ca. 0.2 Å greater for the C(O) carbons in comparison to the other four quinone carbons. Deprotonation of 1$^+$BF$_4^-$ with KO$^t$Bu in the presence of 18-crown-6 produced the salt K(18-C-6)$^+$[(1,4-Q)Rh(COD)]$^-$.K(18-C-6)BF$_4$, in which each quinone oxygen is linked to a crown ether encapsulated potassium ion (FIG. 1). It is noted that X-ray data for this salt were of moderate quality, but sufficient to establish the connectivity shown and establish that the indicated structure is correct.

The cross-coupling of organoborates and organic electrophiles has become an important synthetic tool in organic chemistry. See: Suzuki, A. *Acc. Chem. Res.* 1982, 15, 178. Miyaura, N.; Suzuki, A. *Chem. Rev.* 1995, 95, 2457. While palladium is often used as the transition metal in the catalyst for this reaction, rhodium can also be effective. Especially noteworthy are the rhodium-catalyzed addition of arylboronic acids to aldehydes and the 1,4-addition of arylboronic acids to enones. See, respectively, (1) Sakai, M.; Ueda, M.; Miyaura, N. *Angew. Chem. Int. Ed.* 1998, 37, 3279. Ueda, M.; Miyaura, N. *J. Org. Chem.* 2000, 65, 4450. Fürstner, A.; Krause, H. *Adv. Synth. Catal.* 2001, 343. Pucheault, M.; Darses, S.; Genet, J. P. *J. Am. Chem. Soc.* 2004, 126, 15356; (2) Takaya, Y.; Ogasawara, M.; Hayashi, T. *J. Am. Chem. Soc.* 1998, 120, 5579. Batey, R. A.; Thadani, A. N.; Smil, D. V. *Org. Lett.* 1999, 1, 1683. Ramnauth, J.; Poulin, O.; Bratovanov, S. S.; Rakhit, S.; Maddaford, S. P. *Org. Lett.* 2001, 3, 2571. Kuriyama, M.; Nagai, K.; Yamada, K.; Miwa, Y.; Taga, T.; Tomioka, K. *J. Am. Chem. Soc.* 2002, 124, 8932. (e) Hayashi, T.; Takahashi, M.; Takaya, Y.; Ogasawara, M. *J. Am. Chem. Soc.* 2002, 124, 5052. Yoshida, K.; Ogasawara, M.; Hayashi, T. *J. Am. Chem. Soc.* 2002, 124, 10984. Itooka, R.; Iguchi, Y.; Miyaura, N. *J. Org. Chem.* 2003, 68, 6000. Duursma, A.; Boiteau, J.-G.; Kefort, L.; Boogers, J. A. F.; de Vries, A. H. M.; de Vries, J. G.; Minnaard, A. J.; Fering a, B. L. *J. Org. Chem.* 2004, 69, 8045. The results obtained for arylboronic acid addition to benzaldehydes as catalyzed by rhodium quinone complexes are given in Table 1.

An inspection of the data in Table 1 shows some remarkable behavior. From entries 1-6 it is shown that the cationic rhodium hydroquinone complex $1^+BF_4^-$ had catalytic activity when a base (KOH) is present. Addition of the neutral salt $1^+BF_4^-$ had no effect (entry 5). It is concluded that the base likely functions to deprotonate the—quinonoid —OH groups. In agreement with this, the anionic quinone complex $K^+3^-$ was found to be a very effective catalyst, giving high yields at 75° C. or higher temperatures. Interestingly, the yield drops dramatically when a crown ether is added to the reaction mixture or when $K(18\text{-}C\text{-}6)^+3^-$ is used as the catalyst in place of $K^+3^-$-(entries 13, 15). In a similar vein, the activity is reduced by the inclusion of $n\text{-}Bu_4N^+BF_4^-$ (entries 14, 16). Likely related to this is the observation that $Li^+3^-$ is a more effective catalyst than $K^+3^-$, as indicated by entries 10 and 12 compared to 17 and 18. This behavior clearly signals heterobimetallic or dual function catalysis in which the alkali metal $Li^+$ or $K^+$ enhances the electrophilic activation of the aldehyde carbon by interacting with the carbonyl oxygen, thus facilitating aryl transfer from the rhodium catalyst. See: Sammis, G. M.; Danjo, H.; Jacobsen, E. N. *J. Am. Chem. Soc.* 2004, 126, 9928. Shibasaki, M.; Yoshikawa, N. *Chem. Rev.* 2002, 102, 2187. Yarnagiwa, N.; Matsunaga, S.; Shibasaki, M. *J. Am. Chem. Soc.* 2003, 125, 16178. Li, C.; Eidjaja, E.; Garland, M. *J. Am. Chem. Soc.* 2003, 125, 5540. Guo, N.; Li, L.; Marks, T. J. *J. Am. Chem. Soc.* 2004, 126, 6542. Comte, V.; Le Gendre, P.; Richard, P.; Moise, C. *Organometallics* 2005, 24, 1439. This hypothesis is in accord with the reduced reactivity that is found when the alkali metal is chelated with a crown ether or replaced with the much larger $n\text{-}Bu_4N^+$ ion.

See Table 1 below setting forth results of the rhodium-catalyzed arylation of ArCHO with Ar'B(OH)$_2$ in water solvent.

TABLE 1

Results for Rhodium-Catalyzed Arylation of Aldehydes

| entry | aldehyde | catalyst | additives(eg) | T/° C. | time(h) | yield(%)[b] |
|---|---|---|---|---|---|---|
| 1 | $C_6H_5CHO$ | $1^+BF_4^-$ | none | 95 | 3 | NR[c] |
| 2[d] | $C_6H_5CHO$ | $1^+BF_4^-$ | none | 95 | 3 | NR |
| 3 | $C_6H_5CHO$ | $1^+BF_4^-$ | none | 75 | 3 | NR |
| 4 | $C_6H_5CHO$ | $1^+BF_4^-$ | KOH(1.2) | 75 | 3 | 97 |
| 5 | $C_6H_5CHO$ | $1^+BF_4^-$ | $K^+BF_4^-$(1.2) | 75 | 3 | NR |
| 6 | $C_6H_5CHO$ | $1^+BF_4^-$ | none | 50 | 16 | NR |
| 7 | $C_6H_5CHO$ | $K^+3^-$ | none | 95 | 3 | 96 |
| 8 | $C_6H_5CHO$ | $K^+3^-$ | none | 75 | 3 | 93(90) |
| 9 | $C_6H_5CHO$ | $K^+3^-$ | none | 60 | 3 | 81 |
| 10 | $C_6H_5CHO$ | $K^+3^-$ | none | 50 | 3 | 48 |
| 11 | $C_6H_5CHO$ | $K^+3^-$ | none | 50 | 16 | 84 |
| 12 | $C_6H_5CHO$ | $K^+3^-$ | none | 25 | 16 | 19 |
| 13 | $C_6H_5CHO$ | $K^+3^-$ | 18-C-6(0.075) | 75 | 3 | 14 |
| 14 | $C_6H_5CHO$ | $K^+3^-$ | $n\text{-}Bu_4N^+BF_4^-$(0.075) | 75 | 3 | 24 |
| 15 | $C_6H_5CHO$ | $K^+(18\text{-}C\text{-}6)3^-$ | none | 75 | 3 | 13 |
| 16 | $C_6H_5CHO$ | $n\text{-}Nu_4N^+3^-$ | none | 75 | 3 | 2 |
| 17 | $C_6H_5CHO$ | $Li^+3^-$ | none | 50 | 3 | 96(91) |
| 18 | $C_6H_5CHO$ | $Li^+3^-$ | none | 25 | 16 | 40 |
| 19 | $C_6H_5CHO$ | $[Rh(COD)Cl]_2$ | none | 75 | 3 | NR |
| 20 | $C_6H_5CHO$ | $[Rh(COD)_2]^+BF_4^-$ | none | 75 | 3 | NR |
| 21 | $C_6H_5CHO$ | $[Rh(COD)_2]^+BF_4^-$ | KOH(0.025) | 75 | 3 | 1 |
| 22 | $C_6H_5CHO$ | $[Rh(COD)_2]^+BF_4^-$ | KOH(1.2) | 75 | 3 | 99 |
| 23 | $C_6H_5CHO$ | none | KOH(1.2) | 75 | 3 | NR |
| 24 | $4\text{-}MeOC_6H_4CHO$ | $K^+3^{3-}$ | none | 75 | 3 | 81(78) |
| 25 | $2,4,6\text{-}Me_3C_6H_2CHO$ | $K^+3^-$ | none | 75 | 3 | 69(68) |
| 26 | $4\text{-}MeC_6H_4CHO$ | $K^+3^-$ | none | 75 | 3 | 99(97) |
| 27 | $4\text{-}ClC_6H_4CHO$ | $K^+3^-$ | none | 75 | 3 | 99(97) |
| 28 | $4\text{-}PhC_6H_4CHO$ | $K^+3^-$ | none | 75 | 3 | 98(93) |
| 29 | $4\text{-}O_2NC_6H_4CHO$ | $K^+3^-$ | none | 75 | 3 | 99(92) |
| 30[e] | $C_6H_5CHO$ | $K^+3^-$ | none | 75 | 3 | 96(91) |
| 31[f] | $C_6H_5CHO$ | $K^+3^-$ | none | 75 | 3 | 94(90) |

TABLE 1-continued

Results for Rhodium-Catalyzed Arylation of Aldehydes

| entry | aldehyde | catalyst | additives(eg) | T/° C. | time(h) | yield(%)[b] |
|---|---|---|---|---|---|---|
| 32[g] | $C_6H_5CHO$ | $K^+3^-$ | none | 75 | 3 | 20 |
| 33[h] | $C_6H_5CHO$ | $K^+3^-$ | none | 75 | 3 | 2 |

Figure 4:
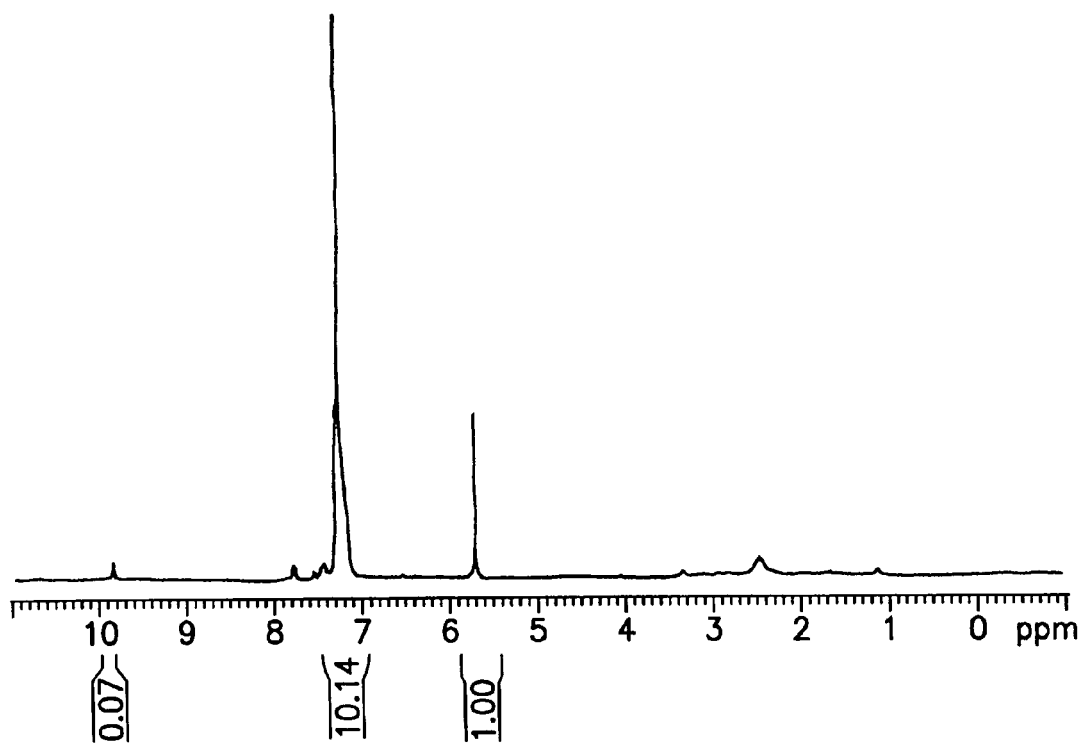
FIG. 4 shows the $^1H$ NMR spectrum of diphenyl alcohol, the product of the rhodium-quinonoid catalyzed addition of phenyl boronic acid to benzaldahyde.

[a]Conditions: 2 mL water, 0.025 mmol catalyst, 1.0 mmol aldehyde substrate, 1.2 mmol Ar'B(OH)$_2$ (Ar' = $C_6H_5$ for entries 1-29).
[b]Yield determined by NMR; isolated yields in parentheses.
[c]No reaction.
[d]Solvent p-dioxane (2 mL).
[e]Ar' = 4-MeOC$_6$H$_4$B(OH)$_2$.
[f]Ar' = 4-MeC$_6$H$_4$B group in Ar'B(OH)$_2$ hinder the reaction, as has been found with other catalyst systems. See: Sakai, M.; Ueda, M.; Miyaura, N. Angew. Chem. Int. Ed. 1998, 37, 3279. Table 1 also indicates that the catalytic conditions are tolerant of a wide range of aryl substituents in the aldehyde reactant (entries 8 and 24-29). See also FIGS. 4 and 5, which present typical proton NMR data for the products of the arylation reactions.

Suzuki-Miyaura type coupling reactions involving boronic acids are usually facilitated by the presence of stoichiometric external base (e.g., compare entries 20 and 22). It has been debated whether the base serves to increase the rate of transmetallation from boron to the transition metal catalyst by binding to the former or by binding to the latter. Recent theoretical studies suggest that the hard base OH$^-$ functions by binding to the electrophilic boron, and that this increases the rate of subsequent transmetallation. See: Braga, A. A. C.; Morgon, N. H.; Ujaque, G.; Maseras, F. J. Am. Chem. Soc. 2005, 127, 9298.

The data in Table 1 show that K$^+$3$^-$ and Li$^+$3$^-$ are effective catalysts without the necessity of adding an external base. From this we conclude that the 3$^-$ complex itself can function as the base by binding to the boron via the quinonoid oxygens. In the present case, the binding of 3$^-$ to the boronic acid assists the transmetallation step by decreasing the electrophilicity of the boron and by placing the transition metal in the vicinity of the transferring group (Ar'). $^1$H NMR spectra of PhB(OH)$_2$ in D$_2$O with and without K$^+$3$^-$ present indicate that an interaction occurs.

The ability of the quinone ring system to undergo facile hapticity changes ($\eta^4 \rightarrow \eta^5$, etc.) may play a role in the ability of 3$^-$ to function as an organometalloligand in this manner. It is concluded that catalyst 3$^-$ is able to act in a bifunctional (and cooperative) manner, as has recently been suggested for other types of catalytic reactions. See: Casey, C. P.; Johnson, J. B.; Singer, S. W.; Cui, Q. J. Am. Chem. Soc. 2005, 127, 3100. (b) Noyori, R.; Hashiguchi, S. Acc. Chem. Res. 1997, 30, 97. (c) Josephsohn, N. S.; Kuntz, K. W.; Snapper, M. L.; Hoveyda, A. H. J. Am. Chem. Soc. 2001, 123, 11594. (d) Mermerian, A. H.; Fu, G. C. J. Am. Chem. Soc. 2003, 125, 4050.

In summarizing the above, Applicants have characterized a π-bonded rhodium quinonoid complex that functions as a good catalyst for the coupling of arylboronic acids and aldehydes. The catalysis is heterobimetallic in that both the transition metal and concomitant alkali metal counterion play an integral part in the reaction. In addition, the anionic quinonoid catalyst itself plays a bifunctional role by acting as a ligand to the boronic acid and as a Lewis acid receptor site for the aryl group in the requisite transmetallation. In the reaction with aldehydes, the anionic rhodium catalyst appears to operate in an intriguing multifunctional manner with one quinone oxygen acting as a ligand by binding to the boron center, thus facilitating transmetallation, while the other quinone oxygen binds to the alkali metal counterion of the catalyst and indirectly activates the aldehyde electrophile (rate: M$^+$=Li$^+$>K$^+$ >>Bu$_4$N$^+$). These interactions from the quinone oxygen atoms imply a supramolecular assembly of the boronic acid donor, the catalyst and the organic acceptor, as illustrated in Scheme 1. Such a preorganization is unprecedented and offers opportunities to significantly improve product yields and stereoselectivities in comparison to standard catalytic systems.

Scheme 1.
Rhodium quinonoid catalyst is multifunctional by pre-assembling the reactants prior to formation of product.

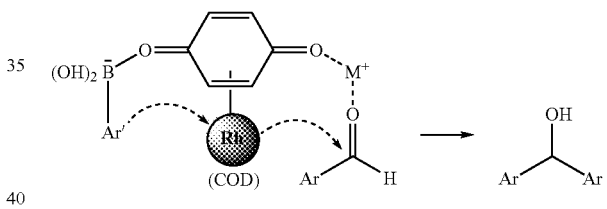

Thus, it can be seen that Applicants have successfully synthesized an anion rhodium quinone complex that can function as a catalyst for Suzuki-like coupling of arylboronic acids and aldehydes. Advantageously, the catalytic reactivity can be adjusted/tuned by protonation/deprotonation of the quinone complex. The catalyst as a potassium salt also functions in a heterobimetallic manner in that both the rhodium and the alkali metal play an integral role in the reaction. Moreover, the anionic rhodium complex is itself bifunctional in that it acts as a ligand in activating the boronic acid towards transmetallation of the rhodium center. The determination of a heterobimetallic catalyst that is also bifunctional (cooperative) and pH-tunable for an important class of reactions is believed to be unique.

Synthetic Procedure and Characterization of the New Materials General: All reactions were carried out under N$_2$ in flame-dried glassware. HPLC grade THF and Diethyl Ether solvents were used as received. [Rh(COD)Cl]$_2$ was provided by Strem Chemicals. The $^1$H NMR spectra were recorded by Bruker(300 MHz) spectrometers. Elementary analyses were performed by Quantitative Technologies Inc.

Synthesis of 1$^+$BF$_4$$^-$: After flame drying the glassware, [Rh(COD)Cl]$_2$ (0.20 g, 0.41 mmol) and AgBF$_4$(0.19 g, 0.97 mmol) were mixed for 1 h at room temperature in a mixed solution of methylene chloride (4 mL) and acetone (1 mL). While stirring, a white precipitate formed on the bottom of the glassware. 1,4-hydroquinone (0.18 g, 1.63 mmol) was dissolved in acetone (2 mL) and added to the reaction mixture. After stirring for 2 h at r.t., the solvent was removed via rotary evaporation. The residue was taken up in methylene chloride (3 mL) and slowly added dropwise to ether through a glass filter. The yellow precipitate was filtered and washed three times with 10 mL aliquots of diethyl ether. The isolated yield was 72% (0.24 g, 0.59 mmol). To get the single crystals: $1^+BF_4^-$ (25 mg) was dissolved in a mixture of acetone (0.1 mL) and methylene chloride (1.5 mL) in a 5 mL-vial. Diethyl ether (3 mL) was carefully added to the upper layer. The solution was placed in a refrigerator for 3 days. Yellow crystals formed on the wall of vial.

$^1$H NMR (CD$_2$Cl$_2$): δ 7.64 (brs, OH, 2H), 6.53 (s, hydroquinone ring, 4H), 4.41 (br, COD, 4H), 2.40 (m, COD, 4H), 2.12 (m, COD, 4H) ppm. Elemental Anal. Calcd for $C_{14}O_2H_{18}Rh_1B_1F_4$: C, 41.21; H, 4.45. Found: C, 41.44; H, 4.31.

Synthesis of 2: $1^+BF_4^-$ (0.1 g, 0.24 mmol) was dissolved in THF (5 mL) in a 20 mL-one neck Schlenk flask and the solution was mixed with 1 eq. K$^t$BuO (0.027 g, 0.25 mmol) and stirred at r.t. for 2 h. While, stirring the solution became turbid and a yellow precipitate formed. The precipitate was filtered under N$_2$ and the collected solid was washed three times with THF and dried in vacuum. The isolated yield was 83% (0.065 g, 0.20 mmol).

$^1$H NMR (DMSO-d$^6$): δ 5.94 (d, J=6.3 Hz, arene ring, 2H), 5.51 (br, OH, 1H) 5.20 (d, J=6.3 Hz, arene ring, 2H), 3.83 (br, COD, 4H), 2.20 (m, COD, 4H), 1.97 m, COD, 4H) ppm. Elemental Anal. Calcd for $C_{14}O_2H_{17}Rh_1$: C, 52.52; H, 5.35. Found: C, 50.82; H, 5.33.

Synthesis of K$^+$3$^-$: 1 (0.1 g, 0.24 mmol) was dissolved in THF (5 mL) in 20 mL-one neck Schlenk flask and the solution was mixed with 3 eq. K$^t$BuO (0.082 g, 0.74 mmol) and stirred at r.t. for 2 h. While stirring, the solution became turbid and a yellow precipitate formed. The precipitate was filtered under N$_2$ and the collected solid was washed five times with THF and dried in vacuum. The isolated yield was 50% (0.074 g, 0.12 mmol).

$^1$H NMR (DMSO-d$^6$): δ 4.89 (s, benzoquinone ring, 4H), 3.47 (br, COD, 4H), 2.18 (m, COD, 4H), 1.96 (m, COD, 4H) ppm. $^1$H NMR (D$_2$O): δ 5.67 (s, benzoquinone ring, 4H), 4.01 (br, COD, 4H), 2.35 (m, COD, 4H), 2.13 (m, COD, 4H) ppm. Elemental Anal. Calcd for $C_{14}O_2H_{16}Rh_1K_3B_2F_8$: C, 27.56; H, 2.64. Found: C, 27.20; H, 2.59.

Synthesis of K(18-crown-6)$^+$3$^-$: 18-crown-6 (0.19 g, 0.74 mmol) was dissolved in THF (5 mL) in 20 mL-one neck Schlenk flask and K$^t$BuO solution (0.082 g, 0.74 mmol) in 5 mL was added to this solution. The solution was stirred for 30 minutes. To this solution, a THF (5 mL) solution of $1^+BF_4^-$ (0.1 g, 0.24 mmol) was added. The solution was stirred for 5 hours at room temperature. Compared to the synthetic procedure of K$^+$3$^-$, no precipitate formed. The solvent was evaporated and the resulting yellow solid was washed five times with diethyl ether (15 mL, five times). After drying in vacuum, the solid was dissolved in THF and diethyl ether was added carefully on the layer of THF. After a few days yellow crystals were collected and the isolated yield was 79% (0.20 g, 0.19 mmol).

$^1$H NMR (DMSO-d$^6$): δ 4.88 (s, benzoquinone ring, 4H), 3.54 (s, crown ether, 48H), 3.47 (br, COD, 4H), 2.19 (m, COD, 4H), 1.96 (m, COD, 4H) ppm. $^1$H NMR (CD$_2$Cl$_2$): δ 5.24 (s, benzoquinone ring, 4H), 3.69 (br, COD, 4H), 3.60 (s, crown ether, 48H), 2.26 (m, COD, 4H), 2.03 (m, COD, 4H) ppm. $^1$H NMR (D$_2$O): δ 5.68 (s, benzoquinone ring, 4H), 4.02 (br, COD, 4H), 3.72 (s, crown ether, 48H), 2.35 (m, COD, 4H), 2.14 (m, COD, 4H) ppm. Elemental Anal. Calcd. for $C_{38}O_{15}H_{66}Rh_1K_2B_1F_4$: C, 44.28; H, 6.45. Found; C, 44.48; H, 6.61.

Synthesis of Li$^+$3$^-$: $1^+BF_4^-$: (0.1 g, 0.24 mmol) was dissolved in THF (5 mL) in a 20 mL-one neck Schlenk flask and the solution was mixed with 3 eq. Li$^t$BuO (0.060 g, 0.75 mmol) and stirred at r.t. for 5 h. The solvent was evaporated and the resulting yellow solid was washed five times with mixture of THF and diethyl ether (v/v=1:5, 15 mL, five times). The precipitate was filtered under N$_2$ and the collected solid was washed five times with THF and dried in vacuum. The isolated yield was 56% (0.057 g, 0.14 mmol)

$^1$H NMR (DMSO-d$^6$): δ 4.96 (s, benzoquinone ring, 4H), 3.51 (br, COD, 4H), 2.20 (m, COD, 4H), 1.98 (m, COD, 4H) ppm. Elemental Anal. Calcd. for $C_{14}O_2H_{16}Rh_1Li_2B_1F_4$: C, 40.05; H, 3.84. Found; C, 40.04; H, 4.17.

Synthesis of n-Bu$_4$$^+$3$^-$: $1^+BF_4^-$ (0.1 g, 0.24 mmol) and Bu$_4$N+BF$_4$-(0.21 g, 0.75 mmol) were dissolved in THF (5 mL) in a 20 mL-one neck Schlenk flask and the solution was mixed with 3 eq. K$^t$BuO (0.082 g, 0.74 mmol) and stirred at r.t. for 4 h. After reaction, in comparison to the synthetic procedure for K$^+$3$^-$, there was no precipitate. The solvent was evaporated and the resulting yellow solid was washed five times with diethyl ether (15 mL, five times). After drying in vacuum, the solid was dissolved in THF and the diethyl ether was added carefully on the layer of THF. After a few days yellow crystals were collected and the isolated yield was 61% (0.23 g, 0.15 mmol).

$^1$H NMR (DMSO-d$^6$): δ 4.90 (s, benzoquinone ring, 4H), 3.48 (br, COD, 4H), 3.17 (t, J=7.8 Hz, Bu, 32H), 2.19 (m, COD, 4H), 1.97 (m, COD, 4H), 1.57 (brm, Bu, 32H), 1.32 (m, Bu, 32H), 0.94 (t, J=7.2 Hz, Bu, 48H) ppm. Elemental Anal. Calcd. for $C_{78}H_{160}O_2N_4Rh_1B_3F_{12}$: C, 60.46; H, 10.41; N, 3.62. Found; C, 59.23; H, 10.52; N, 3.52.

General Procedure of Catalytic Reaction

Distilled water (2 mL) was added to an elongated 15 mL-Schlenk flask. The water was bubbled for 5 minutes with nitrogen gas. After bubbling, the catalyst K$^+$3$^-$ (15 mg, 0.024 mmol), phenylboronic acid (0.15 g, 1.23 mmol) and benzaldehyde (0.1 ml, 0.98 mmol) were added. The mixture solution was heated at 75° C. for 3 hours. After reaction, the solution was cooled to room temperature and CDCl$_3$ (3.5 mL) was added. The solution was shaken for 1 minute and the CDCl$_3$ part was directly analyzed by $^1$H NMR. The yield was calculated by the comparison of peak area of aldehyde reactant and the benzyl proton of the product alcohol.

Crystallography. X-ray data collection was carried out using a Bruker single-crystal diffractometer equipped with an APEX CCD area detector and controlled by SMART version 5.0. Collection was done either at room temperature or 100 K. Data reduction was performed by SAINT version 6.0 and absorption corrections were applied by SADABS version 2.0. The structures were typically determined by direct methods and refined on F squared by use of programs in SHELXTL version 5.0. Most hydrogen atoms appeared in a difference map, or they were generally inserted in ideal positions, riding on the atoms to which they are attached.

The X-ray structure of [(H$_2$Q)Rh(COD)]BF$_4$.Et$_2$O established the anticipated η$^6$-bonding mode. The solved structure contained two independent complexes of rhodium with hydroquinone (HQ) and (COD) ligands, a BF$_4$ counterion and a diethyl ether molecule filling the void. Each HQ-Rh-COD complex is positioned on a two-fold axis, Rh(1) along an axis parallel to b, Rh(2) along one parallel to a (the asymmetric unit is charge-balanced, +1 for the two half complexes, and −1 for the BF$_4$). Notable features remained, particularly a "ghost" atom, and the R value remained high—around 13%.

Rechecking by different methods showed that orthorhombic symmetry (mmm) produced R(int) and R(symm) convincingly below 5%. Cell_now ranked the original cell first (C-centered). The space group was uniquely determined to be C222(1) by the systematic absences. Solving by use of the Patterson method yielded the same solution for the heavy atoms as found earlier. However, some original difficulties were highlighted: three independent heavy atoms found, with estimated atomic numbers 48, 39, and 24—although the only heavy atom is believed to be rhodium. The third heavy atom had been tentatively treated as carbon, but it may be something bigger, and its position mirrored the second rhodium atom on the other side of the HQ ligand. This suggested that the atom might be a fractional part of a disordered rhodium atom. When its identification as Rh(3) was tested, the R values dropped and the bonds to the expected ligands became apparent. Rh(3) occupied a position between the HQ coordinated to Rh(2) and the COD coordinated to the Rh(2) in the adjacent cell. Since neither ligand can bond to two rhodium atoms, disorder of the whole Rh(2) complex is believed to be present. The HQ ligand on Rh(2) is approximately overlapped by another on Rh(3), and the COD on the adjacent Rh(2) is approximately overlapped by another on Rh(3). This "whole molecule disorder" is difficult to model accurately, so an approximate model was constructed by restraining the ligands on Rh(2) and Rh(3) to be similar to the better-defined ligands on Rh(1), by treating all atoms except rhodium in the Rh(3) complex as isotropic, and by ignoring the likely disorder in the diethyl ether. With this model, the occupancy of the Rh(2) complex was about 68%, the Rh(3) complex about 32%; hence the electron counts on the three rhodium atoms are roughly consistent with the Patterson results. That is not the end of the disorder besetting this crystal; it is also a racemic twin, with enantiomers in a 55:45 ratio. Some complications in the analysis may preclude placing much weight on bond lengths and angles, but the connectivity is certainly determined (R1=0.089%).

X-ray quality crystals of $K^+3^-$ could not be grown, but the butylammonium salt was readily obtained by metathesis and its X-ray structure determined as $Bu_4N^+[(1,4-Q)Rh(COD)]^-\cdot 3\ Bu_4NBF_4$ (R1=0.076%). The Rh—C bond lengths clearly indicated an $\eta^4$-bonding mode, with the quinone Rh—C distances being ca. 0.2 Å greater for the C(O) carbons in comparison to the other four quinone carbons. Deprotonation of $1^+BF_4^-$ with KO$^t$Bu in the presence of 18-crown-6 produced the salt $K(18-C-6)+[(1,4-Q)Rh(COD)]^-\cdot K(18-C-6)BF_4$, in which each quinone oxygen is linked to a crown ether encapsulated potassium ion. X-ray data for this salt were only moderate in quality (R1=12.8%), but sufficient to establish connectivity.

II. Highly Efficient 1,4-Additions of Electron Deficient Aryl Boronic Acids with a Novel Rhodium(I) Quinonoid Catalyst As noted above, rhodium(I) quinonoid catalysts are a remarkably efficient new class of reagents for the conjugate addition of aryl boronic acids. In this section, the use of these reagents in catalyzing the highly efficient 1,4-additions of a broad range of boronic acids, including heteroaromatic and an example of trihalogenated aryl boronic acids is described. The rhodium(I) catalyzed conjugate addition of aryl boronic acids to electron deficient olefins is a mild approach to carbon-carbon bond formation. See Sakai, M.; Hayashi, H.; Miyaura, N. *Organometallics,* 1997, 16, 4229-4231; Fagnou, K.; Lautens, M. *Chem. Rev.* 2003, 103, 169-196; Hayashi, T.; Yamasaki, K. *Chem. Rev.* 2003, 103, 2829-2844.d) Hayashi, T. *Pure Appl. Chem.* 2004, 76, 465-475. This approach has been shown to be more chemoselective and widely applicable for molecules with reactive functionality than traditional cuprate or grignard chemistry. See Chapman, C. J.; Frost, C. G. *Adv. Synth. Catal.* 2002, 345, 353-355; Moss, R. J.; Wadsworth, K. J.; Chapman, C. J.; Frost, C. G. *Chem. Commun.* 2004, 1984-1985; Paquin, J.; Defieber, C.; Stephenson, C. R. J.; Carreira, E. M. *J. Am. Chem. Soc.* 2005, 127, 10850-10851. In addition, the enantioselective rhodium catalyzed conjugate addition reaction with chiral ligands, as shown by Hayashi and others, demonstrates the application of this methodology toward asymmetric synthesis. See Chapman, C. J.; Frost, C. G. *Adv. Synth. Catal.* 2002, 345, 353-355; Moss, R. J.; Wadsworth, K. J.; Chapman, C. J.; Frost, C. G. *Chem. Commun.* 2004, 1984-1985; Paquin, J.; Defieber, C.; Stephenson, C. R. J.; Carreira, E. M. *J. Am. Chem. Soc.* 2005, 127, 10850-10851. While this methodology is mild and highly effective for most substrates, aryl boronic acids with electron withdrawing substituents undergo competitive proto-deborylation. Attempts to favor 1,4-addition have included increasing aryl boronic acid equivalents, increasing catalyst loading, altering the aqueous/organic solvent ratio, decreasing temperature and in situ generation of aryl boronate reactants. The highest reported yields are afforded with 2-10 equivalents of aryl boronic acid, $\geq 3$ mol % catalyst loading and prolonged reaction at 90-100° C. In this section, it is reported that the use of a new rhodium quinone catalyst provides a mild, highly effective and operationally facile procedure for conjugate addition of aryl boronic acids to 1-cyclohexen-2-one.

As noted in the previous sections, the development of the anionic rhodium $\eta^4$-quinonoid complex $K^+3^-$ (or "3.K") is described and it was found that it efficiently catalyzes the 1,2-addition of aryl boronates to aldehydes according to Eq. 1 below. See, Son, S. U.; Kim, S. B.; Reingold, J. A.; Carpenter, G. B.; Sweigart, D. A. *J. Am. Chem. Soc.* 2005, 127, 12238-12239. The oxygen sensitive 3.K was synthesized and isolated by double deprotonation of the hydroquinone precursor complex 1 in THF, via the neutral semiquinone 2 (Scheme 2).

In this section it is reported that preformed catalyst 3.K is also effective in conjugate 1,4-addition reactions, as described in Scheme 3. The air-sensitivity of anionic catalyst 3.K may be a drawback in this procedure, potentially necessitating greater catalyst loadings than may otherwise be required. In addressing this problem, it was found that the operational ease of the catalyzed conjugate additions of aryl boronic acids can be greatly

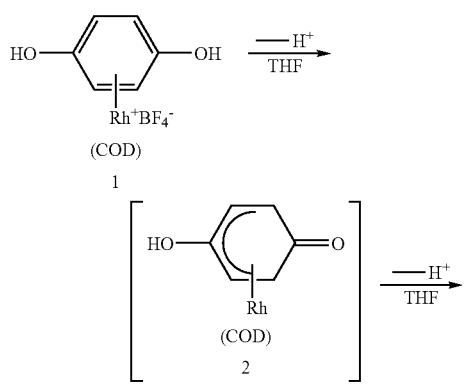

Scheme 2.
Double deprotonation of rhodium hydroquinone 1 to afford the active quinonoid complex 3·K.

-continued

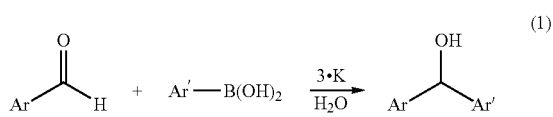
3·K facilitated by the in situ generation of catalyst 3.M (M=Li, Na, K, Cs) from the air stable rhodium hydroquinone salt 1. The conjugate addition reactions in DME/H$_2$O with catalyst 3.Li, which is generated in situ from 1 and LiOH, are highly efficient and afford excellent yields with negligible side products in short reaction times at 50° C. (Table 2). A significant aspect of the new procedure is the low catalyst loading (0.5 mol % reduced from 2.5 mol % in Scheme 3) and low boronic acid equivalency (1.2 equiv) relative to the $$Ar \overset{O}{\underset{H}{\|}} + Ar'-B(OH)_2 \xrightarrow[H_2O]{3\cdot K} Ar \overset{OH}{\underset{Ar'}{\|}} \quad (1)$$

conjugate acceptor as compared to the conditions reported in the literature. An evaluation of counter ions indicates that 3.Li is more efficacious than the corresponding potassium salt 3.K (Table 2, entries 4-6). This counter ion effect was also evident in catalyzed 1,2-additions and may be ascribed to general acid activation of the organic electrophile.

Scheme 3.
An example of conjugate addition with an aryl
boronic acid using preformed quinonoid catalyst 3·K.

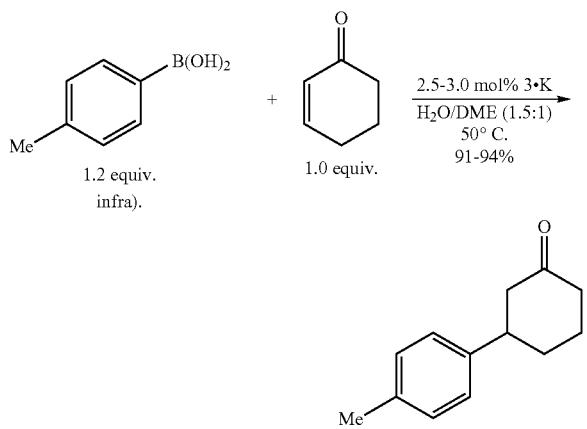

TABLE 2

Base study for an electron rich and electron poor

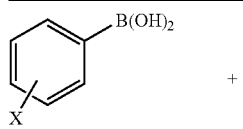
+

4b. X = p-Me
e. X = m-NO$_2$

TABLE 2-continued

Base study for an electron rich and electron poor

[diagram: cyclohexenone + 1. LiOH, DME/H$_2$O, 50° C., 1 h → product]

5

[product structure]

6b. X = p-Me
e. X = m-NO$_2$

| entry | 1 (mol %) | LiOH (mol %) | 6b yield[a] (%) | 6e yield[a] (%) |
|---|---|---|---|---|
| 1 | 0.5 | 0 | 4 | 0 |
| 2 | 0.5 | 0.25 | 17 | 23 |
| 3 | 0.5 | 0.5 | 30 | 38 |
| 4 | 0.5 | 0.75 | 63 (31)[b] | 46 (33)[b] |
| 5 | 0.5 | 1.0 | 90 (31)[b] | 57 (59)[b] |
| 6 | 0.5 | 2.0 | 96 (81)[b] | 87 (56)[b] |
| 7 | 0.5 | 120 | 99 | 19 |

[a]Isolated yield after silica gel chromatography.
[b]Yield in parentheses arises from substitution of KOH in place of LiOH.

Preliminary results showed that the reaction exhibited a marked dependence on base equivalency, which was studied through systematic variation (Table 2). The role of base in the conjugate addition of aryl boronic acids to electron deficient olefins is not well understood. For the conjugate addition of p-tolyl boronic acid to 2-cyclohexen-1-one, stoichiometric LiOH (1.2 eq) affords excellent yield of desired ketone 6b (99%, entry 7, Table 2), although the reaction is equally productive with 2.0 mol % of base (96%, entry 6). The most dramatic change in yield was seen upon increasing base from 0.75 mol % (63%) to 1.0 mol % (90%) (entries 4-5). This behavior is consistent with complete activation of hydroquinone 1 into the active quinonoid catalyst 3.Li where 1 mol % of LiOH is required for complete double deprotonation of the precatalyst. In contrast, the m-nitrophenyl boronic acid analogue affords the highest yield of desired ketone 6e (87%) with 2.0 mol % of LiOH. Increasing the base quantity to 120 mol % results in reduced yield (19%, entry 7) and a prevalent side product, nitrobenzene, resulting from proto-deborylation. This study demonstrates that base is required for the reaction and 2.0 mol % provides optimal yield of the desired conjugate addition product.

During further studies to optimize the reaction conditions, a series of additives and bases were examined. Catalytic amounts of carbonate bases, Na$_2$CO$_3$ (2.0 mol %) or Cs$_2$CO$_3$ (2.0 mol %), are effective at producing high yielding conjugate additions with boronic acid 4a (Table 3, entries 6 & 8), while stoichiometric amounts (120 mol %) of carbonate bases (entries 7 & 9) attenuated reactivity. Pyridine, either catalytic or quantitative, arrests all reactivity and consistent with this observation is the lack of product with pyridine boronic acids. Additional hydroquinone shows no detectable effect upon reaction outcome while lithium salts, such as LiCl or LiBF$_4$, either diminish the amount of product or completely arrest the reaction. The addition reaction can be run in the absence of organic solvent, however, stoichiometric base (120 mol %) is required for efficient reaction (entry 10 versus 11). This result is presumably due to the solubilization of the boronic acid into the aqueous phase by formation of the corresponding -ate complex. Preferred reaction conditions, outlined as a general procedure in the experimental section, are highly effective and facile for a range of boronic acid substrates. Using 2-cyclohexen-1-one as our conjugate acceptor, a number of different aryl boronic acids were studied with our optimized reaction conditions (Table 4). Ketone products 6a-g (entries 1-7) are afforded in high yields, with low catalyst loading (0.5 mol %) and low boronic acid equivalency (1.2 eq). Electron deficient boronic acids (entries 5-9) are afforded in excellent yields (94-99%) without any procedural modification from the earlier analogues. Improved yields (92-93%) of meta-nitro analogue 6l were achieved either by increasing the catalyst loading (2.0 mol %, entry 12) or increasing equivalencies of boronic acid (1.5 equiv, entry 13). Tri-fluoro analogues 6j and 6k (entry 14,15) were afforded in good to moderate yields (70% and 30% respectively). This is believed to be the first report of conjugate addition of a tri-halogenated aryl boronic acid. Efforts are underway to further optimize the additions of tri-fluorophenyl boronic acids 4j and 4k. Both 2,4-bis(trifluoromethyl)phenyl boronic acid and ortho-nitro phenyl boronic acid failed to produce the desired addition products under our standard conditions. The 4-, 5- or 6-indoloboronic acids (Table 5) undergo conjugate addition while N-Boc-2-indoloboronic acid (entry 1) does not afford any product. The additions of 4-indoloboronic acid (entry 2, Table 4) and o-tolyl boronic acid (entry 3, Table 4) show that ortho substitution can be tolerated, despite the attenuated reactivity observed for o-substituted boronic acids and documented difficulties of reactions with N-Boc protected pyrrole-2-boronic acids. See Lautens, M.; Mancuso, J.; Grover, H. *Synthesis* 2004, 12, 2006-2014.

TABLE 3

The role of additives and alternate bases upon conjugate addition reaction.

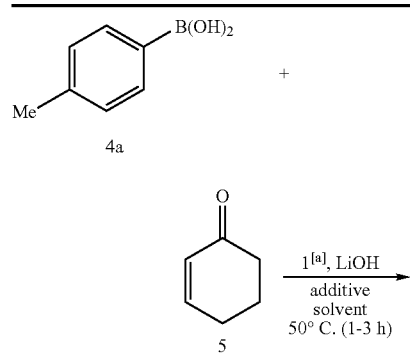

| entry | LiOH (mol %) | additive (mol %) | solvent | 6a yield[b] (%) |
|---|---|---|---|---|
| 1 | 0.5 | hydroquinone (2.0) | DME/H$_2$O | 31[c] |
| 2 | 0.5 | LiBF$_4$ (120) | DME/H$_2$O | — |
| 3 | 0.5 | LiCl (120) | DME/H$_2$O | 20 |
| 4 | — | pyridine (2.0) | DME/H$_2$O | — |
| 5 | — | pyridine (120) | DME/H$_2$O | — |
| 6 | — | Cs$_2$CO$_3$ (2.0) | DME/H$_2$O | 97 |
| 7 | — | Cs$_2$CO$_3$ (120) | DME/H$_2$O | 68 |
| 8 | — | Na$_2$CO$_3$ (2.0) | DME/H$_2$O | 93 |
| 9 | — | Na$_2$CO$_3$ (120) | DME/H$_2$O | 74 |
| 10 | 2.0 | — | H$_2$O | — |
| 11 | 120 | — | H$_2$O | 99 |

[a]0.5 mol %
[b]Isolated yield after silica gel chromatography.
[c]Compare to Table 1 entry 3.

TABLE 4

Conjugate addition of a variety of boronic acids to 2-cyclohexen-1-one.

| entry | boronic acid[b] (4) | 1 (mol %) | product | yield[c] (%) |
|---|---|---|---|---|
| 1 | a. X = H | 0.5 | 6a | 98 |
| 2 | b. X = p-Me | 0.5 | 6b | 97 |
| 3 | c. X = o-Me | 0.5 | 6c | 99 |
| 4 | d. X = 4-NH-Boc | 0.5 | 6d | 99 |
| 5 | e. X = p-OMe | 0.5 | 6e | 97 |
| 6 | f. X = p-Cl | 0.5 | 6f | 99 |
| 7 | g. X = p-F | 0.5 | 6g | 94 |
| 8 | g. X = p-F[d] | 0.5 | 6g | 99 |

TABLE 4-continued

Conjugate addition of a variety of boronic acids to 2-cyclohexen-1-one.

| 9 | h. X = 3-Cl, 4-F | 0.5 | 6h | 96 |
|---|---|---|---|---|
| 10 | i. X = m-NO$_2$ | 0.5 | 6i | 85 |
| 12 | i. X = m-NO$_2$ | 2.0 | 6i | 93 |
| 13 | i. X = m-NO$_2$[e] | 0.5 | 6i | 92 |
| 14 | j. X = 3,4,5-tri-F[d] | 2.0 | 6j | 70 |
| 15 | k. X = 2,3,4-tri-F | 2.0 | 6k | 30 |

[a]2.0 mol %
[b]1.2 equiv. relative to 1-cyclohexen-2-one
[c]Isolated yield after silica gel chromatography.
[d]from boroxime
[e]1.5 eq of boronic acid

TABLE 5

Indole boronic acid conjugate addition to 1-cyclohexene-2-one.

| entry | boronic acid (7) | 1 (mol %) | product | yield[b] (%) |
|---|---|---|---|---|
| 1 | a, 2-B(OH)$_2$ R = Boc | 0.5 | 8a | — |
| 2 | b, 4-B(OH)$_2$ R = H | 0.5 | 8b | 80 |
| 3 | c, 5-B(OH)$_2$ R = H | 0.5 | 8c | 63 |
| 4 | d, 6-B(OH)$_2$ R = H | 0.5 | 8d | 86 |

[a]2.0 mol %
[b]Isolated yield after silica gel chromatography.

TABLE 6

Conjugate addition to a variety of conjugate acceptors

| entry | substrate | product | yield[c] (%) |
|---|---|---|---|
| 1 | 9a | 10a | 96[d] |
| 2 | 9b | 10b | 95[d] |
| 3 | 9c | 10c | 14[e] |
| 4 | 9d | 10d | 97 |

[a]0.5 mol %
[b]2.0 mol %
[c]Isolated yield after silica gel chromatography based on 9:
[d]1 mol % 1 and 4.0 mol % LiOH.
[e]1.5 equiv of 4b and 150 mol % LiOH.

We hypothesize that the reactivity observed for quinone complex 3.Li is due to bifunctional activation in catalyzing the reaction of boronic acids and electron deficient olefins. In the activation of the boronic acid, the alkoxide of the hydroquinone ligand can act as a nucleophile to activate the boronic acid directly for transmetallation to the rhodium center (Scheme 4). After formation of the rhodium aryl species, the lithium counter-ion can act as a generalacid to pre-organize and activate the conjugate acceptor for carbo-metallation. This pre-organization acts to accelerate the rate of conjugate addition in relation to the rate of proto-deborylation, thereby allowing the use of extremely electron deficient aryl boronic acids. Mechanistic studies are underway to elucidate the details of this new class of Rh$^I$ catalysts.

Scheme 4.

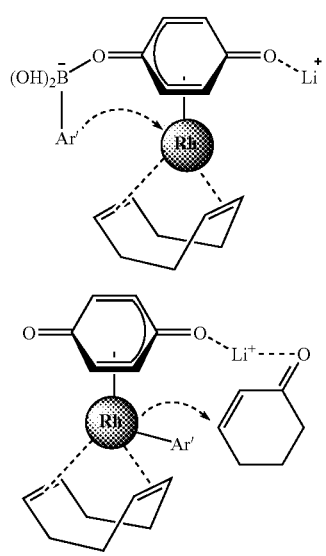

[a] General base activation of the boronic acid to the -ate complex.
[b] General acid activation of the electron deficient olefin.

Thus, Applicants have developed and disclose an efficient procedure for the conjugate addition of electron deficient aryl boronic acids to 2-cyclohexen-1-one and other activated conjugate acceptors (Table 6). Accordingly, examples of conjugate acceptors also include those of Table 6 above.

Scheme 5.
Summary of 1,4-conjugate additions to 2-cyclohex-1-one catalyzed by the rhodium hydroquinone precursor complex 1.

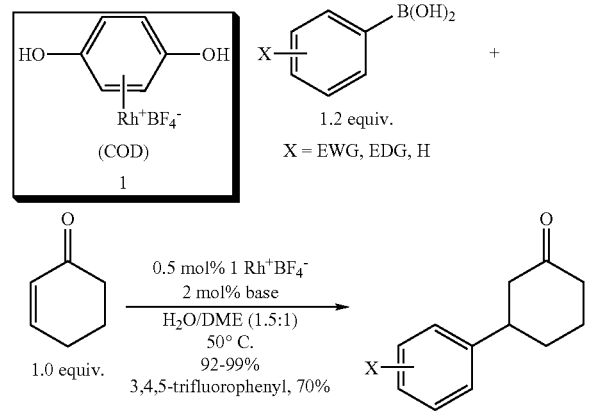

This catalyst system is noteworthy due to the operational and high isolated yields with low levels of catalyst and boronic acid loading in an aqueous solution. The yields of addition products, using extremely electron deficient aryl boronic acids including the first report of trihalogenated aryl boronic acids, are excellent with minimal proto-deborylation and a complete absence of Heck type products. See Zou, G.; Wang, Z.; Zhu, J.; Tang, J. *Chem. Commun.* 2003, 2438-2439; Mori, A.; Danda, Y.; Fujii, T.; Hirabayashi, K.; Osakada, K. *J. Am. Chem. Soc.* 2001, 123, 1077-410775.

In summary, disclosed is a new and highly efficient catalytic system using a rhodium quinonoid complex to catalyze the conjugate addition of aryl boronic acids. The process is characterized by high isolated yields of product using extremely electron deficient aromaticboronic acids while maintaining low catalyst loadings in short reaction times at about 50° C. Additionally, examples of trifluoronated aryl additions are presented above which may be of interest to the biomedical and pharmaceutical communities. Experimental Section—The rhodium(I) hydroquinone catalyst was synthesized as described above. Also see, for customary synthetic procedures, e.g. Y.-S. Huang, S. Sabo-Etienne, X.-D. He, B. Chaudret, *Organometallic* 1992, 11, 303; S. Sun, G. B. Carpenter, D. A. Sweigart, *J. Organomet. Chem.* 1996, 512, 257; J. Le Bras, H. Amouri, J. Vaissermann, *Organometallics* 1998, 17, 1116; M. Oh, G. B. Carpenter, D. A. Sweigart, *Organometallics* 2002, 21, 1290; J. Moussa, C. Guyard-Duhayon, P. Herson, H. Amouri, M. N. Ragwr, A. Jutand, *Organometallics* 2004, 23, 6231.

General Procedure: A 1-dram vial fitted with a Teflon cap was charged with aryl boronic acid (1.2 mmol) and enone (1.0 mmol) and dimethoxyethane (DME, 1.0 mL). A solution of 1 (0.02 M DME, 0.250 mL, 0.005 mmol, 0.5 mol %) followed by an aqueous LiOH solution (1.0 M, 0.020 mL, 0.020 mmol, 2.0 mol %). The headspace of the vial was flushed with $N_2$ and deoxygenated $H_2O$ (1.5 mL) was added. The vial was capped and the resulting mixture was stirred at 50° C. for 1 h. The reaction mixture was diluted with a saturated solution of $NH_4Cl$ (5 mL), extracted with 25% EtOAc/hexanes (2×5 mL), dried ($Na_2SO_4$), filtered through a silica plug, and concentrated to afford pure product as characterized by $^1H$ and $^{13}C$ NMR and high resolution mass spectrometry. Note, it was also found that diethyl ether and THF can be used in place of DME, however no reaction is observed in toluene as solvent.

Rhodium quinonoid catalysts, arising from precatalyst 1, are believed to be a remarkably efficient new class of reagents for the conjugate addition of aryl boronic acids. Thus, as explained above, herein Applicants describe the use of these reagents in catalyzing the highly efficient addition of a broad range of boronic acids, including heteroaromatic and the first believed example of trihalogenated aryl boronic acids.

Figure 6:
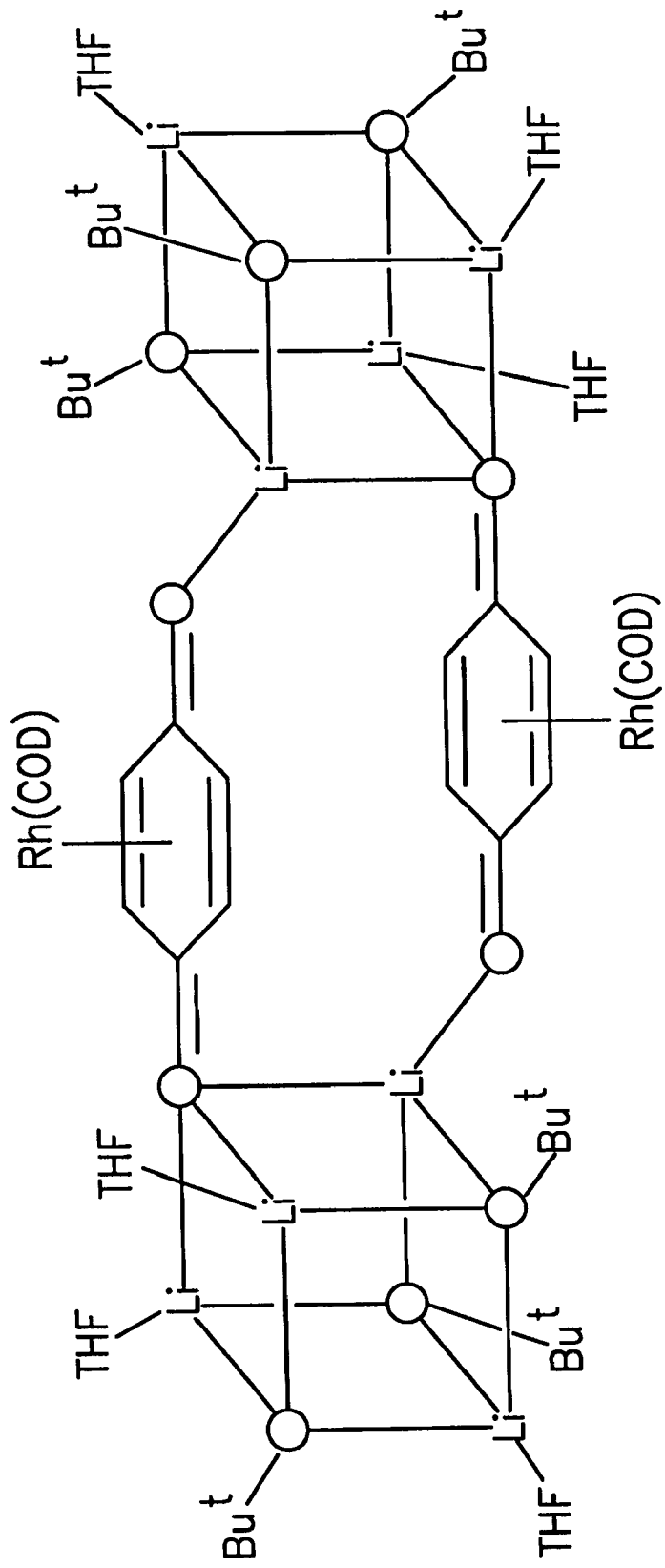
FIG. 6 shows lithium $Li_4O_4$ cubanes linked by the bifunctional organometalloligand $[(\eta^4\text{-quinone})Rh(COD)]^-$.

III. Lithium Alkoxide $Li_4O_4$ Cubanes Bridged by Rhodium Quinonoid Organometalloligands The afore-described rhodium quinonoid complexes may also be used to bridge lithium alkoxide cubanes. Lithium $Li_4O_4$ cubanes linked by the bifunctional organometalloligand [($\eta^4$ quinone)Rh (COD)]$^-$ can result in an unprecedented doubly-bridged motif. The dimeric assembly features cubane units that are connected by a transition metal complex and which incorporate a quinone oxygen at one of the corners, as shown in FIG. 6.

Organolithium reagents with alkoxide and similar oxygen-donor ligands frequently aggregate in aprotic solvents into rectangular $Li_2O_2$ and cubic $Li_4O_4$ fragments, and lithium $Li_4O_4$ cubane species are especially prevalent and have been extensively investigated because of the great importance of organolithium reagents in organic synthesis. See E. Weiss, *Angew. Chem.* 1993, 105, 1565; *Angew. Chem. Int. Ed.* 1993, 32, 1501; M. A. Beswick, D. S. Wright in *Comprehensive Organometallic Chemistry*, Vol. 1, (Eds.: E. W. Abel, F. G. A. Stone, G. Wilkinson), Pergamon, Oxford, 1995, pp. 1 34; P. G. Williard, J. M. Salvino, *Tet. Lett.* 1985, 26, 3931; H.-J.

Gais, U. Dingerdissen, C. Krüger, K. Angermund, *J. Am. Chem. Soc.* 1987, 109, 3775; M. A. Nichols, A. T. McPhail, E. M. Arnett, *J. Am. Chem. Soc.* 1991, 113, 6222; P. J. Pospisil, S. R. Wilson, E. N. Jacobsen, *J. Am. Chem. Soc.* 1992, 114, 7585; S. Schütte, U. Pieper, U. Klingebiel, D. Stalke, *J. Organomet. Chem.* 1993, 446, 45; U. Piarulli, D. N. Williams, C. Floriani, G. Gervasio, D. Viterbo, *Chem. Commun.* 1994, 1409; Y. Apeloig, I. Zharov, D. Bravo-Zhivotovskii, Y. Ovchinnikov, Y. Struchkov, *J. Organomet. Chem.* 1995, 499, 73; W. Clegg, S. T. Liddle, R. Snaith, A. E. H. Wheatley, *New J. Chem.* 1998, 1323; D. R. Armstrong, J. E. Davies, R. P. Davies, P. R. Raithby, R. Snaith, A. E. H. Wheatley, *New J. Chem.* 1999, 35; A. J. Hoskin, D. W. Stephan, *Organomtallics* 1999, 18, 2479; C. Jones, P. C. Junk, S. G. Leary, N. A. Smithies, *J. Chem. Soc., Dalton Trans.* 2000, 3186; J. Strauch, T. H. Warren, G. Erker, R. Fröhlich, P. Saarenketo, *Inorg. Chim. Acta* 2000, 300-302, 810; V. Lorenz, A. Fischer, K. Jacob, W. Bruser, F. T. Edelmann, *Chem. Eur. J.* 2001, 7, 848; T. J. Boyle, T. M. Alam, K. P. Peters, M. A. Rodriguez, *Inorg. Chem.* 2001, 40, 6281; D. Seebach, R. Amstutz, T. Laube, W. B. Schweizer, J. D. Dunitz, *J. Am. Chem. Soc.* 1985, 107, 5403; L. M. Jackman, B. D. Smith, *J. Am. Chem. Soc.* 1988, 110, 3829; M. Brehon, E. K. Cope, F. S. Mair, P. Nolan, J. E. O'Brien, R. G. Pritchard, D. J. Wilcock, *J. Chem. Soc., Dalton Trans.* 1997, 3421; W. Clegg, R. P. Davies, L. Dunbar, N. Feeder, S. T. Liddle, R. E. Mulvey, R. Snaith, A. E. W. Wheatley, *Chem. Commun.* 1999, 1401; T. J. Boyle, D. M. Pedrotty, T. M. Alam, S. C. Vick, M. A. Rodriguez, *Inorg. Chem.* 2000, 39, 5133. In this section, the synthesis and characterization of the novel lithium cubane aggregate 11 shown in FIG. 6, which possesses two unprecedented features: (i) $Li_4O_4$ units incorporating a quinone oxygen donor atom at one of the corners and (ii) $Li_4O_4$ units bridged by two rhodium [(7'-benzoquinone)Rh(COD)]⁻ organometalloligands is described. See also FIG. 7. $li_4O_4$ cubanes can link or bridge by sharing a corner oxygen donor atom. Bridged structures are also known in which the organic moiety attached to a cubane corner oxygen either covalently links to an oxygen in a second cubane, or provides a donor atom that coordinates to a lithium corner in a second cubane. Examples of bridging units in these categories include carbonate and benzamide aza enolates. See T. Maetzke, D. Seebach, *Organometallics* 1990, 9, 3032; S. C. Ball, I. Cragg-Hine, M. G. Davidson, R. P. Davies, M. I. Lopez-Solera, P. R. Raithby, D. Reed, R. Snaith, E. M. Vogl, *Chem. Commun.* 1995, 2147; K. Hyvarinen, M. Kling a, M. Leskelä, *Polyhedron* 1996, 15, 2171. Cubane fragments can also be linked together by "external" multifunctional donors that coordinate to two or more lithium corners. See K. Hyvärinen, M. Kling a, M. Leskelä, *Polyhedron* 1996, 15, 2171; N. D. R. Barnett, R. E. Mulvey, W. Clegg, P. A. O'Neil, *J. Am. Chem. Soc.* 1993, 115, 1573; K. W. Henderson, A. R. Kennedy, L. Macdonald, D. J. MacDougall, *Inorg. Chem.* 2003, 42, 2839; D. J. MacDougall, J. J. Morris, B. C. Noll, K. W. Henderson, *Chem. Commun.* 2005, 456. In these cases the cubanes function as so-called secondary building units (SBUs) that self-assemble in the presence of multifunctional ligands or spacers to generate main-group metal coordination networks. Spacers utilized in this manner include chloride, TMEDA, and p-dioxane.

The molecule reported in this section is unique in that the bifunctional ligand connecting the cubane units is a transition metal complex. As described below, the supramolecular structures analogous to 11 may be accessible with a variety of transition metal fragment. The starting materials for the synthesis of cubane 11 were LiOBuᵗ in THF and the afore-described quinonoid complex [(η⁶-hydroquinone)Rh(COD)]⁺ (1). See also U. Son, S. B. Kim, J. A. Reingold, G. B. Carpenter, D. A. Sweigart, *J. Am. Chem. Soc.* 2005, 127, 12238. Pi-coordination of a metal to hydroquinone is known to greatly facilitate deprotonation, which is accompanied by electron transfer to the metal and changes in the hapticity of the quinonoid ring. See S U. Son, S. B. Kim, J. A. Reingold, G. B. Carpenter, D. A. Sweigart, *J. Am. Chem. Soc.* 2005, 127, 12238; Y.-S. Huang, S. Sabo Etienne, X.-D. He, B. Chaudret, *Organometallics* 1992, 11, 303; S. Sun, G. B. Carpenter, D. A. Sweigart, *J. Organomet. Chem.* 1996, 512, 257; J. Le Bras, H. Amouri, J. Vaissermann, *Organometallics* 1998, 17, 1116; M. Oh, G. B. Carpenter, D. A. Sweigart, *Organometallics* 2002, 21, 1290; J. Moussa, C. Guyard-Duhayon, P. Herson, H. Amouri, M. N. Rager, A. Jutand, *Organometallics* 2004, 23, 6231.

In the case of [(η⁶-hydroquinone)Rh(COD)]⁺(1), neutral η⁵-semiquinone and anionic η⁴-quinone complexes (2 and 3, respectively) are formed as shown in Scheme 6. As described above, pi-bonded quinone complexes analogous to 3 have already found significant applications in 1,2- and 1,4-conjugate addition reactions, in the polymerization of phenylacetylene with nanocatalysts, and in the formation of metal-organometallic coordination networks (manganese as the metal). See S U. Son, S. B. Kim, J. A. Reingold, G. B. Carpenter, D. A. Sweigart, *J. Am. Chem. Soc.* 2005, 127, 12238; M. Oh, G. B. Carpenter, D. A. Sweigart, *Acc. Chem. Res.* 2004, 37.

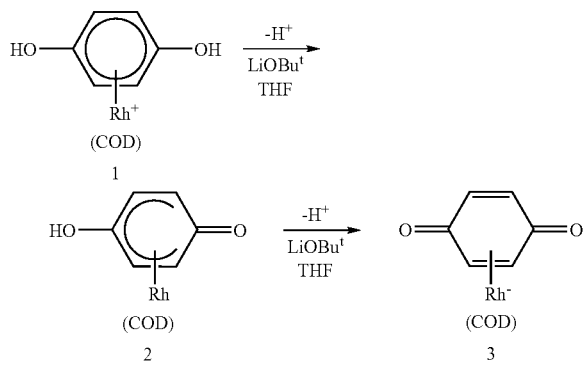

Scheme 6.
Double deprotonation of rhodium hydroquinone 1 to afford the active quinonoid complex 3.

Herein it is shown that the rhodium quinone complex 1 reacts with LiOBuᵗ in THF to afford a novel structural motif in which a quinone oxygen functions as a pseudo-butoxide ligand in a $Li_4O_4$ cubane unit while the other quinone oxygen links to a lithium atom in a second companion cubane unit.

Figure 7:
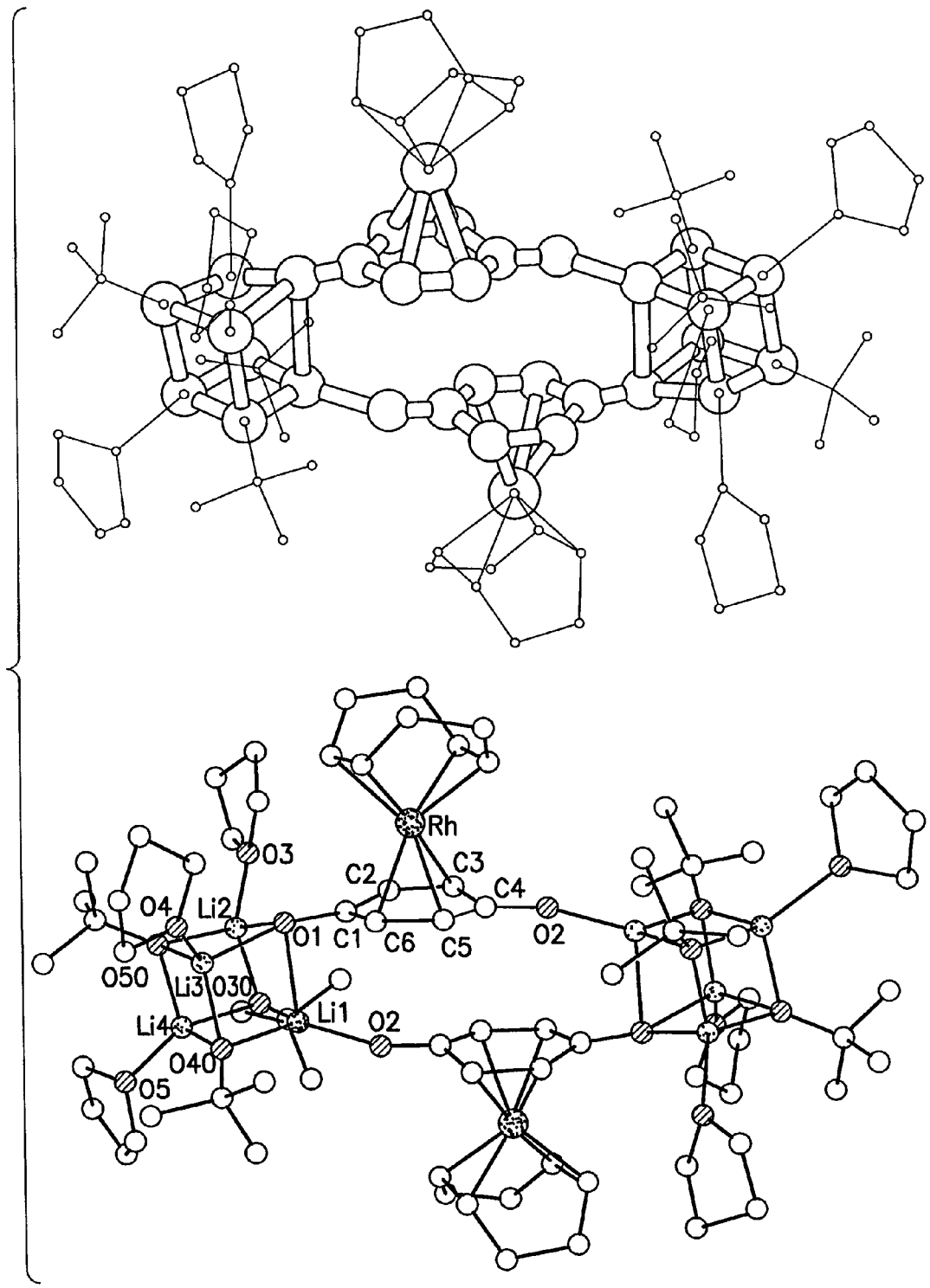
FIG. 7 shows two views of the X-ray structure of the lithium cubane aggregate $[Li_4(OBu^t)_3(THF)_3(\eta^4\text{-benzoquinone})Rh(COD)]_2$ (THF is tetrahydrofuran)

Deprotonation of 1 in THF at room temperature with a fivefold excess of LiOBuᵗ led to a homogeneous yellow solution that slowly deposited crystals of 11 when stored at −15° C. for a period of weeks. The X-ray structure of 11 is shown in FIG. 7. Each of the two $Li_4O_4$ cubanes contains three butoxide oxygens and one quinone oxygen. Three THF ligands and an "external" quinone oxygen complete the pseudo-tetrahedral coordination at each cubane lithium. The quinonoid ring in 11 adopts a boat conformation with the phenolic carbons C1 and C4 bent out of the C2-C3-C5-C6 diene plane away from the rhodium atom by 10° and 13°, respectively. As a consequence, the Rh(COD) fragment is only weakly bonded to C1 and C4 and the overall structure is perhaps best described as an eta-4-quinone. The relatively short C1-O1 and C4-O2 bond lengths of 1.29 and 1.26 Å support this interpretation.

The Li—O bond lengths in 11 are all in the typical 1.8-2.0 Å range except for Li1-O1, which is much larger at 2.36(2) Å. The consequence of the long Li1-O1 bond is that the O1 corner of the cubanes bends out of the O1-Li2-O50-Li3 face with a dihedral angle of 13°. The opposite face of the cubane, Li1-O30-Li4-O40, is planar to within one degree. The 13° bending of the cubane O1 corners effectively increases the separation of the two bridges from each other and this is probably the reason for the ca. 0.4 Å elongation of the Li1-O1 bond beyond that typically found in $Li_4O_4$ structures. The C1-O2 separation in 11 is just 3.1 Å and the quinone rings partially eclipse, with a 3.2 Å ring-to-ring separation, which indicates a fairly strong π-π stacking interaction. See M. Oh, G. B. Carpenter, D. A. Sweigart, *Acc. Chem. Res.* 2004, 37 a) M. Oh, G. B. Carpenter, D. A. Sweigart, *Angew. Chem. Int. Ed.* 2001, 40, 3191; b) M. Oh, G. B. Carpenter, D. A. Sweigart, *Organometallics*, 2003, 22, 1437. If the Li1-O1 bond length was similar to the others (ca. average of 1.95 Å), the bridge-to-bridge separation would be greatly reduced, necessitating significantly different angles from those observed in order to avoid repulsive interactions between the bridges. In terms of the thermodynamic driving force, it is apparent that having a long Li1-O1 bond is the preferred compromise in generating the observed doubly bridged assembly.

Figure 8:
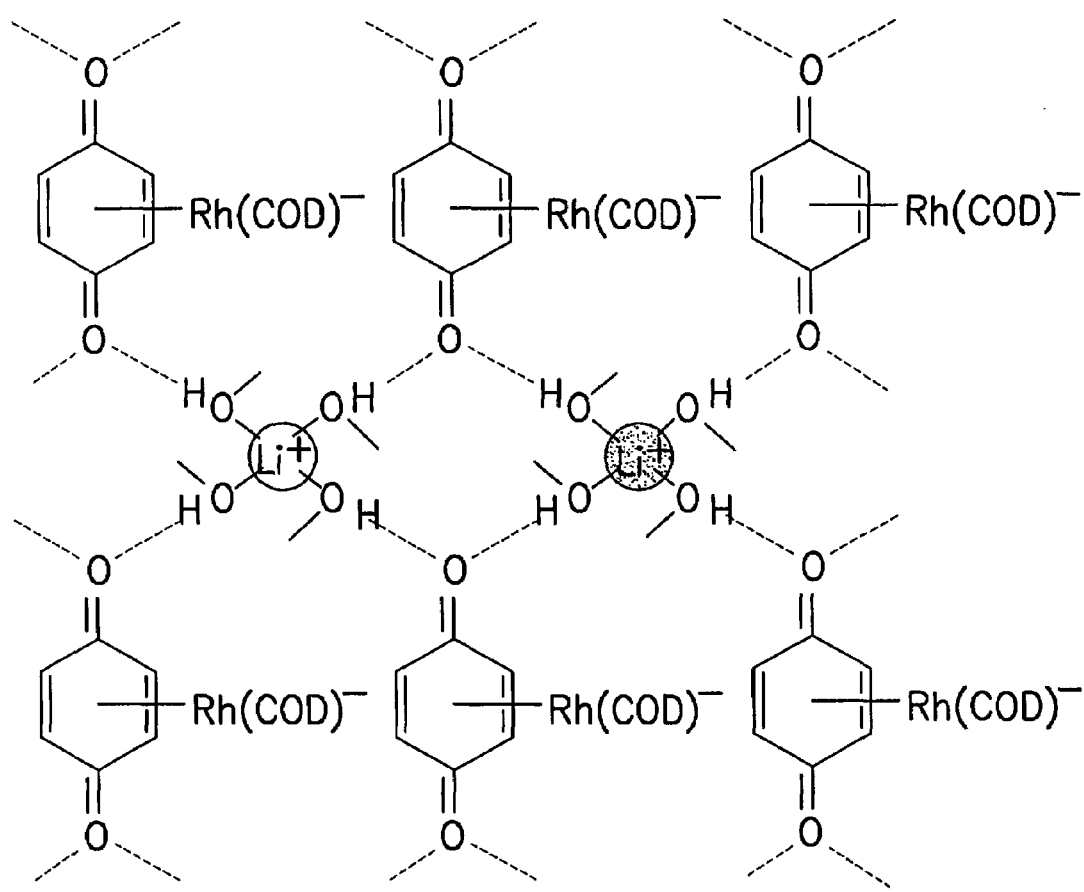
FIG. 8 shows 2-dimensional hydrogen-bonded network of $[Li(MeOH)_4][(\eta^4\text{-quinone})Rh(COD)]_\infty(12)$.

In order to explore possible chemical processes relevant to the formation of 11, a THF solution of complex 1 with five-fold excess $LiOBu^t$ was evaporated before any cubane dimer 11 had formed (one hour after mixing) and the residue was washed with diethyl ether and THF. A portion of the residue dissolved in methanol afforded the salt $[Li(MeOH)_4][(\eta^4\text{-quinone})Rh(COD)]$ (12). The X-ray structure of 12 shows that it included the 2-dimensional hydrogen-bonded network illustrated in FIG. 8. The hydrogen bonds between the quinone oxygens and the methanol ligands have average O—O distances of 2.63 Å.

Figure 9:
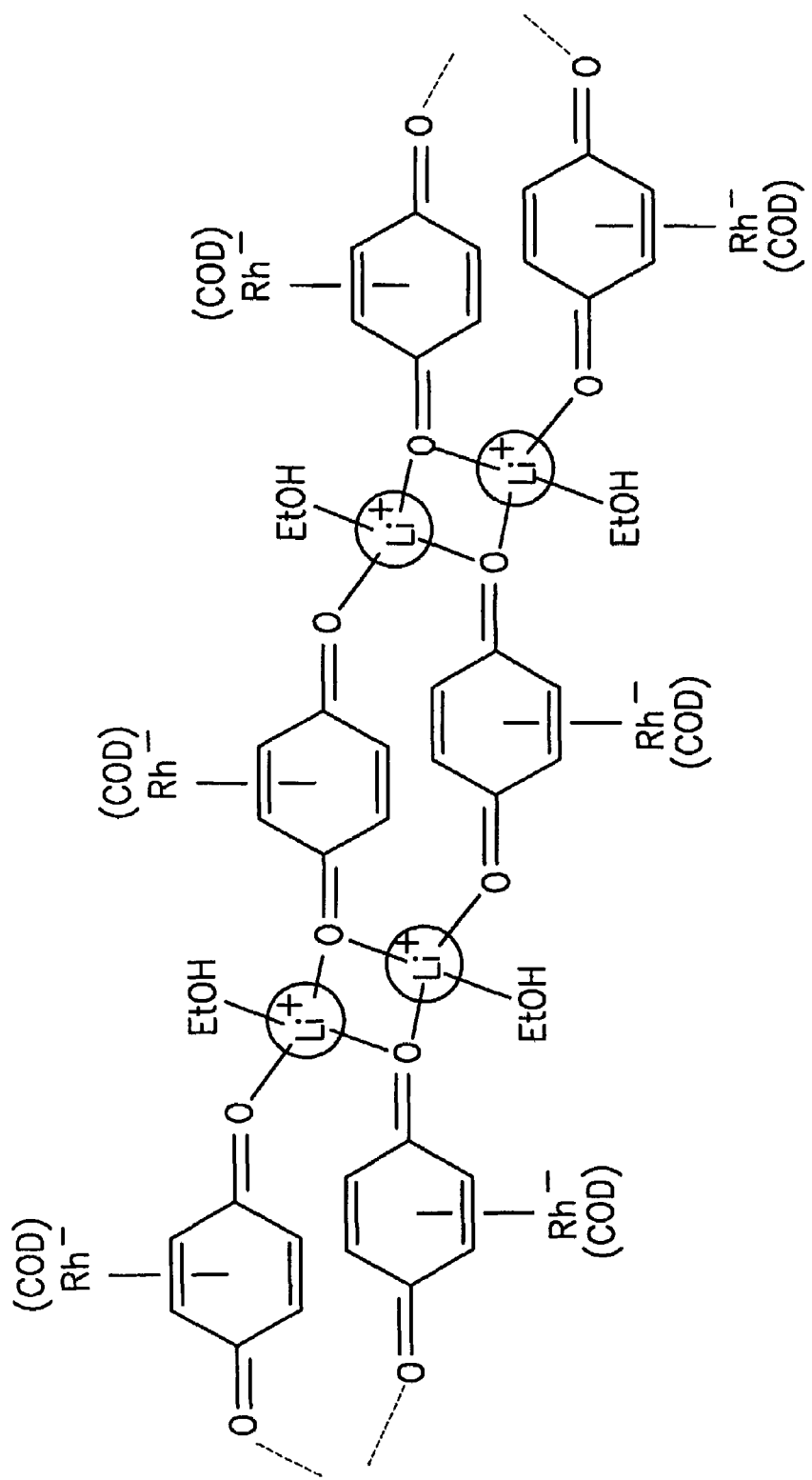
FIG. 9 shows 1-dimensional metal-organometallic coordination network $[Li(EtOH)(BQ)Rh(COD)]_\infty(13)$.

Dissolution of the residue in ethanol instead of methanol afforded product 13 shown in FIG. 9. Complex 13 is a 1-dimensional metal-organometallic coordination network (MOMN) containing rectangular $Li_2O_2$ units linked by anionic $[(\eta^4\text{-quinone})Rh(COD)]^-$ organometalloligands. Each lithium ion is bonded to three quinone oxygens and one ethanol molecule. One quinone oxygen from each spacer molecule is bidentate and forms part of the $Li_2O_2$ ring, while the other oxygen is unidentate and propagates the network by coordinating "externally" to a lithium ion. The X-ray structure of 13 shows that the $Li_2O_2$ rings are nearly square (internal angles 84 and 96°) and the Li—O bond lengths average 1.94 Å, which is in the range found for most of the Li—O bonds in the cubane units in 11 (other than Li1-O1). The coordinated ethanol ligand in 13 is not hydrogen-bonded.

Figure 10:
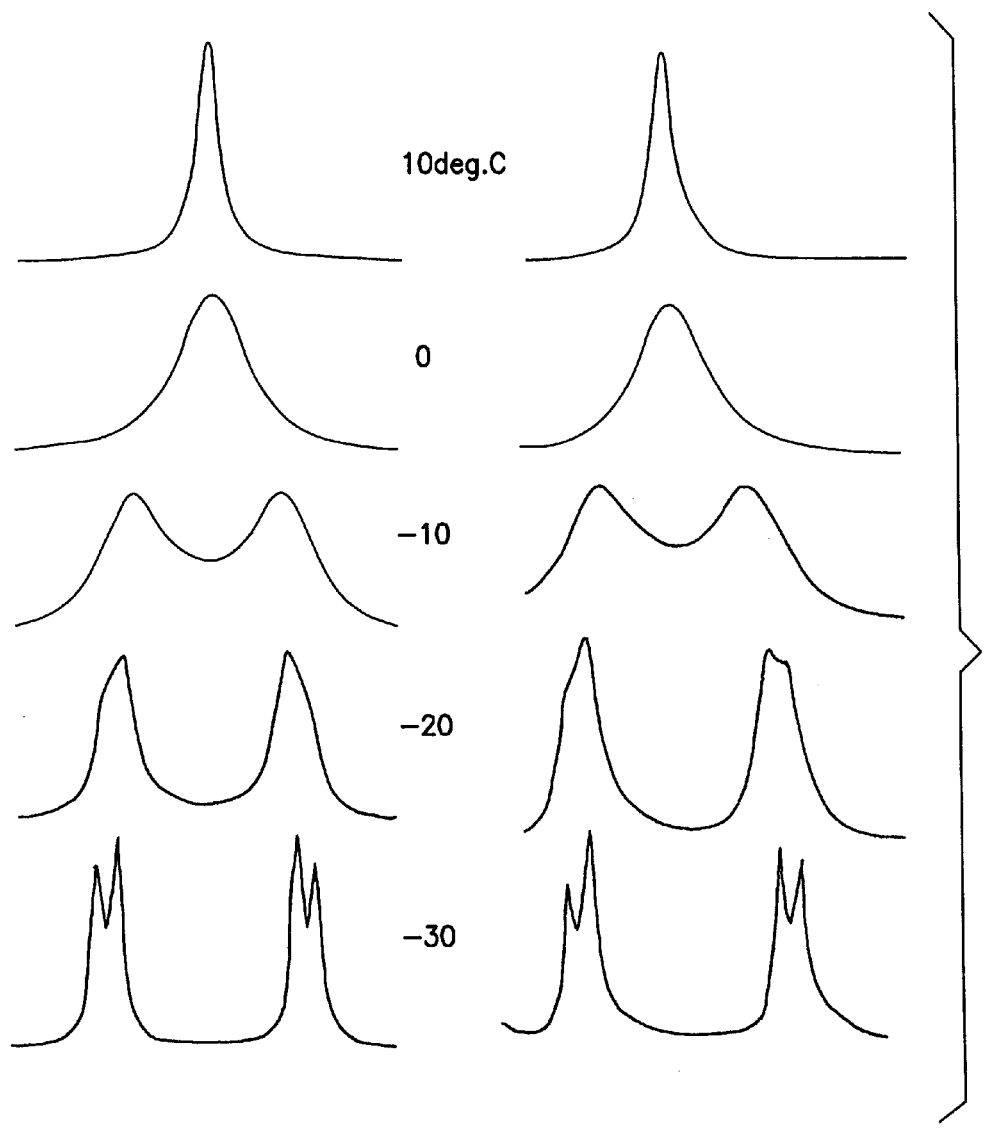
FIG. 10 shows simulated (left) and observed (right) $^1H$ NMR spectra of the quinone hydrogens in a THF-$d^8$ solution of $[(\eta^4\text{-quinone})Rh(COD)]^-$ and excess $LiOBu^t$.
Figure 11:
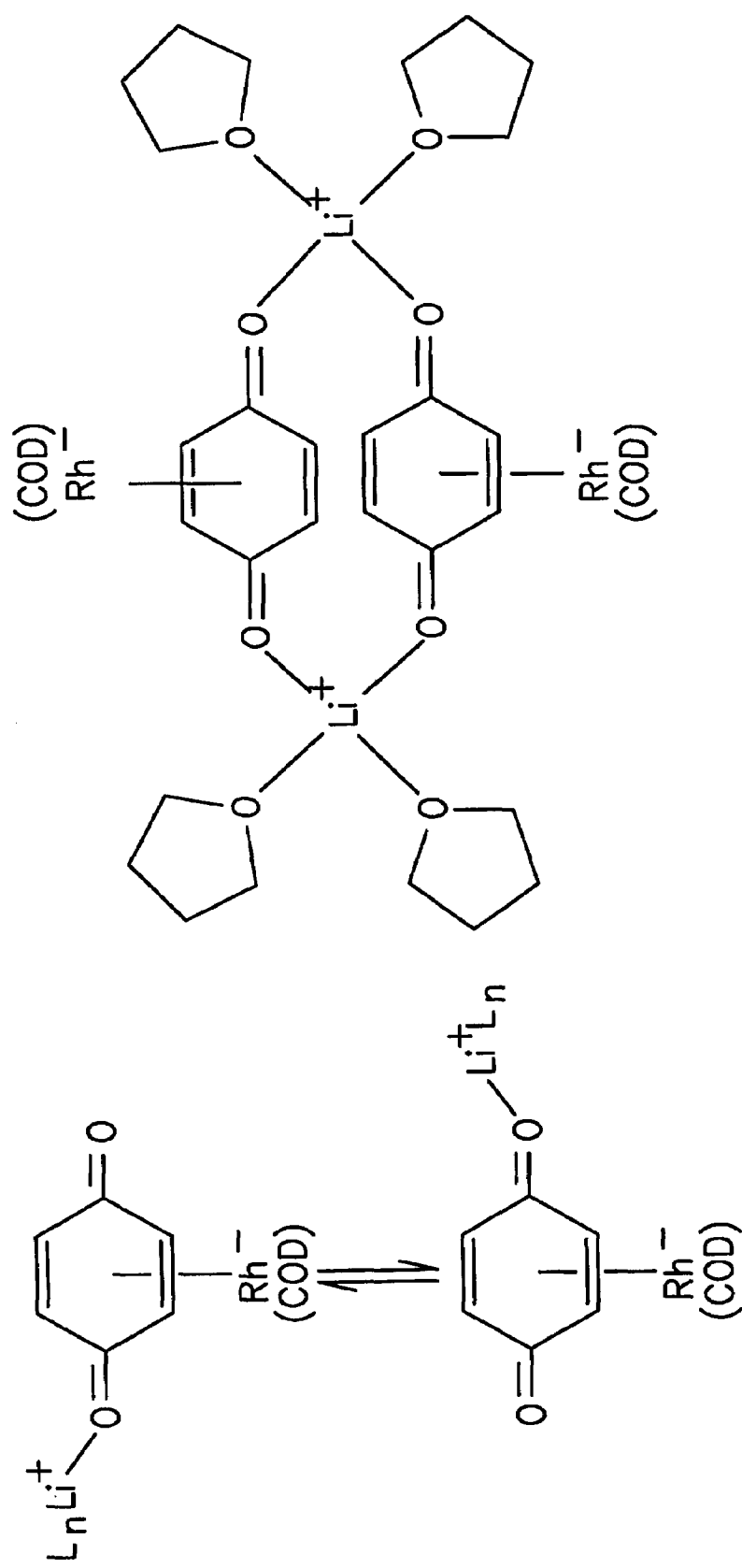
FIG. 11 shows dynamic coordination of the quinone oxygens to lithium in THF solution containing $[(\eta^4\text{-quinone})Rh (COD)]^-$, with possible activated complex shown at right.

Having established the viability of $Li_4O_4$ and $Li_2O_2$ aggregates that incorporate a rhodium $\eta^4$-quinone organometalloligand at a vertex, we next used NMR to probe any dynamic behavior that may be occurring. In THF-d at room temperature, a solution of the slightly soluble cubane 11 gave no evidence for dynamic processes on the NMR timescale. However, a THF solution of hydroquinone complex 1 with ten equivalents of $LiOBu^t$, from which the cubane 11 evolves over a period of days/weeks (vide supra), shows site exchange of the quinone hydrogens in the deprotonated complex $[(\eta^4\text{-benzoquinone})Rh(COD)]^-$ (3), which is rapidly formed in situ according to Scheme 6. The NMR spectra of the quinone hydrogens is illustrated in FIG. 10 for the temperature range 10 to −30° C. Simulations of the observed two-site exchange process gave a very good fit to the Eyring equation with the following activation parameters: $\Delta H^\ddagger = 84$ kJ mol$^{-1}$ and $\Delta S^\ddagger = 110$ J K$^{-1}$mol$^{-1}$. Spectra were simulated using the program WINDNMR, which is freeware downloadable from the website of Professor Hans Reich: www.chem.wisc.edu/areas/reich/plt/windnmr.htm. The process occurring likely involves differential lithium coordination to the quinone oxygens, analogous to that shown in FIG. 11. The "L" ligands likely include THF, although butoxide groups may also be involved. Species with a $Li_2O_2$ core may also be present. The highly positive entropy of activation is suggestive of solvent loss in the transition state to give an activated complex such as that illustrated in FIG. 11. Whatever the specific details, the NMR behavior demonstrates that the quinone oxygen atoms can rapidly change their mode of coordination to lithium in the species that exists prior to the formation of the cubane aggregate 11.

In conclusion, it has been demonstrated that lithium alkoxide aggregates can be synthesized that have two $Li_4O_4$ cubane units bridged by a quinone organometalloligand. See H. Nekola, F. Olbrich, U. Behrens, *Z. Anorg. Allg. Chem.* 2002, 628, 2067; J. F. Allan, R. Nassar, E. Specht, A. Beatty, N. Calin, K. W. Henderson, *J. Am. Chem. Soc.* 2004, 126, 484.

A key to the construction of this discrete species, as well as related polymeric $Li_2O_2$ species, is be the ability of the quinone oxygen atoms in $[(\eta^4\text{-quinone})Rh(COD)]^-$ to function as ligands, both as part of and external to the cubane aggregate itself. The methodology described herein should be readily extendable to anionic π-bonded quinone complexes of a variety of transition metals.

Thus, disclosed herein are organolithium reagents containing bridging transition metals components (e.g. rhodium), which are unique and may have useful applications in organic synthesis. The synthesis and characterization of lithium alkoxide aggregates that differ fundamentally from others previously believed to be known are described. For example, differences include (1) incorporation of quinones into the aggregrates and (2) bridging of the aggregates by a transition metal organometalloligand. Advantageously, lithium cubanes are bridged together with a ligand that simultaneously coordinates to a transition metal. This brings the transition metal into play in future applications of organolithium reagents of this type. Another unique advantage of the $Li_4O_4$ and $Li_2O_2$ aggregates is the incorporation of a quinone oxygen as a vertex in place of an alkoxide.

Experimental Section

All reactions were carried out under $N_2$ in flame-dried glassware. THF and diethyl ether solvents were HPLC grade. $[Rh(COD)Cl]_2$ was purchased from Strem Chemicals, Inc. The $^1H$ NMR spectra were recorded on a 300 MHz Bruker spectrometer. Elemental analyses were performed by Quantitative Technologies Inc., New Jersey, USA.

$Li_4(OBu^t)_3(THF)_3(\eta^4\text{-benzoquinone})Rh(COD)]_2$ (11): At room temperature, $[(\eta^6\text{-hydroquinone})Rh(COD)]BF_4$ (1) (0.10 g, 0.25 mmol) in HPLC grade THF (7 mL) was placed in a flame dried 50 mL Schlenk flask and $LiO^tBu$ (0.10 g, 1.25 mmol) was added with stirring. A yellow precipitate of the neutral ($\eta^5$-semiquinone)Rh(COD) formed initially, but dissolved after addition of the base was complete. The homogeneous yellow solution was stirred for 1 hr and placed in a refrigerator at −15° C. for several weeks. During this time, yellow crystals of 11 formed in 68% isolated yield (0.096 g, 0.085 mmol). $^1H$ NMR (THF-d$^8$): δ=5.64 (d, J=7.0 Hz, benzoquinone, 4H), 4.53 (d, J=6.9 Hz, benzoquinone, 4H), 4.27 (br, COD, 8H), 2.25 (m, COD, 8H), 2.01 (m, COD, 8H), 1.15 (s, t-BuO, 54H).

Preliminaries for the synthesis of complexes 12, 13: At room temperature, $[(\eta^6\text{-hydroquinone})Rh(COD)]BF_4$ (1) and $LiO^tBu$ were combined as described above, stirred for one hr, and the solvent removed with a rotary evaporator. The residue was vacuum dried for 30 min, washed with diethyl ether, then washed with THF and finally dried again under vacuum. The residue, which contained an equivalent of LiBF$_4$, was obtained in 56% yield (0.057 g, 0.14 "mmol"). $^1$H NMR (DMSO-d$^6$): δ=4.96 (s, benzoquinone, 4H), 3.51 (br, COD, 4H), 2.20 (m, COD, 4H), 1.98 (m, COD, 4H). Elemental analysis: calcd. for C14O$_2$H$_{16}$Rh$_1$Li$_2$B$_1$F$_4$: C 40.05, H 3.84; found: C 40.04, H 4.17.

Li(MeOH)$_4$][(η$^4$-benzoquinone)Rh(COD)] (12): The residue described above (20 mg) was dissolved in methanol (1 mL), filtered through a Celite pad and transferred to a 5 mL vial. To this solution, THF (3 mL) was carefully layered and the solution placed in a refrigerator (−15° C.) for three weeks. The yellow crystals formed in an isolated yield of 55% (0.011 g). $^1$H NMR (CD$_3$OD): δ=5.61 (s, benzoquinone ring, 4H), 3.94 (br, COD, 4H), 2.33 (m, COD, 4H), 2.08 (m, COD, 4H). Elemental analysis after drying under vacuum: calcd for C$_{14}$O$_2$H$_{16}$Rh$_1$Li$_1$: C 51.56, H 4.95; found: C 51.50, H 4.60.

Li(EtOH)((η$^4$-benzoquinone)Rh(COD)] (13): The residue described above (25 mg) was dissolved in ethanol (2 mL), filtered through a Celite pad and transferred to a 5 mL vial. After standing for two weeks at room temperature, yellow crystals had formed and were collected in an isolated yield of 90% (0.023 g). $^1$H NMR (CD$_3$OD): δ=5.61 (s, benzoquinone, 4H), 3.94 (br, COD, 4H), 3.59 (q, J=5.2 Hz, EtOH, 2H), 2.33 (m, COD, 4H), 2.08 (m, COD, 4H), 1.16 (t, J=5.2 Hz, EtOH, 3H). Elemental analysis after drying under vacuum: calcd for C$_{14}$O$_2$H$_{16}$Rh$_1$Li$_1$: C 51.56, H 4.95; found: C 51.45, H 5.15.

Dynamic NMR study: [(η$^6$-hydroquinone)Rh(COD)]BF$_4$ (1) (5.0 mg, 0.012 mmol) was dissolved in THF-d$^8$ (1.5 mL) under N$_2$ in an NMR tube and LiOBu$^t$ (9.8 mg, 0.12 mmol) was added at room temperature. The NMR tube was shaken to generate a homogeneous yellow solution, which was then used to record NMR spectra over the temperature range −78° C.-25° C.

Crystallography: X-ray data collection was carried out using a Bruker single-crystal diffractometer equipped with an APEX CCD area detector and controlled by SMART version 5.0. Collection was done either at 100 K. Data reduction was performed by SAINT version 6.0 and absorption corrections were applied by SADABS version 2.0. The structures were typically determined by direct methods and refined on F squared by use of programs in SHELXTL version 5.0. Most hydrogen atoms appeared in a difference map, or they were generally inserted in ideal positions, riding on the atoms to which they are attached. CCDC 281279 (11), 281276 (12), and 281277 (13) contain the supplementary crystallographic data. These data can be obtained free of charge from the Cambridge Crystallographic Data Centre.

Crystal data for [Li$_4$(OBu$^t$)$_3$(THF)$_3$(η$^4$-benzoquinone)Rh (COD)]$_2$ (11). C$_{38}$H$_{67}$Li$_4$O$_8$Rh, M$_r$=782.59, triclinic, P-1, a=10.116(3) Å, b=14.625(4) Å, c=16.304(4) Å, a=101.790(5)°, β=105.855(5)°, Y=107.430(4)0, V=2103.3(9) Å$^3$, Z=2, p$_{clcd}$=1.236 g cm$^{-3}$, F$_{000}$=832, μ=0.451 mm$^{-1}$, 0=1.54-21.04°, reflections collected 13816, independent reflections 4499 (R$_{int}$=0.1682), GoF=1.008, R$_1$=0.0752, wR$_2$=0.1633, largest diffraction peak/hole 0.826/−0.879 Å$^{-3}$.

Crystal data for [Li(MeOH)$_4$] [(η$^4$-benzoquinone)Rh (COD)] (12). C$_{18}$H$_{32}$LiO$_6$Rh, M$_r$=454.29, monoclinic, P2/c, a=11.5682(12) Å, b=8.0923(8) Å, c=12.2963(13) Å, β=105.855(5)°, V=1032.97(18) Å$^3$, Z=2, p$_{cacld}$=1.461 g cm$^{-3}$, F$_{000}$=472, μ=0.855 mm$^{-1}$, θ=1.96-26.42°, reflections collected 9033, independent reflections 1956 (R$_{int}$=0.0876), GoF=0.961, R$_1$=0.0420, wR$_2$=0.0889, largest diffraction peak/hole 1.640/−0.726 Å$^{-3}$.

Crystal data for [Li(EtOH)(η4-benzoquinone)Rh(COD)] (13). C$_{16}$H$_{22}$LiO$_3$Rh, M$_r$=372.19, triclinic, P-1, a=6.962(2) Å, b=7.876(3) Å, c=14.236(5) Å, a=75.933(7)°, β=85.810(8)°, γ=85.434(8)°, V=753.5(4) Åv$^3$, Z=2, p$_{calcd}$=1.640 g cm$^3$, F$_{000}$=380, γ=1.138 mm$^{-1}$, θ=2.67-23.23°, reflections collected 2619, independent reflections 2619 (R$_{int}$=0.0000), GoF=0.950, R$_1$=0.0932, wR$_2$=0.2161, largest diffraction peak/hole 1.365/−1.148 Å$^{-3}$.

IV. Organometallic Crystal Engineering of [1,4- and 1,3-hydroquinone)Rh(P(OPh$_3$)$_2$]$^+$ Salts by Charge Assisted Hydrogen Bonding Organometallic crystal engineering has attracted significant recent attention due to potential catalytic and materials applications. See: D. Braga, F. Grepioni and G. R. Desiraju, *Chem. Rev.*, 1998, 98, 1375; A. D. Burrows, C.-W. Chan, M. M. Chowdhry, J. E. McGrady and D. M. P. Mingos, *Chem. Soc. Rev.*, 1995, 24, 329; S.-S. Sun and A. J. Lees, *Inorg. Chem.*, 2001, 40, 3154; C. J. Kuehl, T. Yamamoto, S. R. Seidel and P. J. Stang, *Org. Lett.*, 4, 913; D. M. Shin, Y. K. Chung and I. S. Lee, *Cryst. Growth Des.*, 2002, 2, 493; Y. Kim and J. G. Verkade, *Inorg. Chem.*, 2003, 42, 4262; R. D. Hartnell and D. P. Arnold, *Organometallics*, 2004, 23, 391; Y.-B. Dong, Y. Geng, J.-P. Ma and R.-Q. Huang, *Inorg. Chem.*, 2005, 44, 1693. D. F. Eaton, A. G. Anderson, W. Tam and W. Wang, *J. Am. Chem. Soc.*, 1987, 109, 1886; I. S. Lee, Y. K. Chung, J. Mun and C. S. Yoon, *Organometallics*, 1999, 18, 5080; I. R. Whittall, A. M. McDonagh, M. G. Humphrey and M. Samoc, *Adv. Organomet. Chem.*, 1999, 43, 349; S. Barlow and S. R. Marder, *Chem. Commun.*, 2000, 1555; M. Albrecht, M. Lutz, A. L. Spek and G. van Koten, *Nature*, 2000, 406, 970; M. Albrecht and G. van Koten, *Angew. Chem., Int. Ed.*, 2001, 40, 3750; P. H. Dinolfo, J. T. Hupp, *Chem. Mater.*, 2001, 13, 3113; S. J. Lee, A. Hu and W. Lin, *J. Am. Chem. Soc.*, 2002, 124, 12948; M. J. E. Resendiz, J. C. Noveron, H. Disteldorf, S. Fischer and P. J. Stang, *Org. Lett.*, 2004, 6, 651.

A variety of inorganic-organometallic coordination polymers using [η$^4$-benzoquinone)Mn(CO)$_3$]$^-$ as the fundamental building block connected to metallic nodes via the quinone oxygen atoms have been reported. See: M. Oh, G. B. Carpenter and D. A. Sweigart, *Acc. Chem. Res.*, 2004, 37, 1; S. U. Son, S. B. Kim, J. A. Reingold, G. B. Carpenter and D. A. Sweigart, *J. Am. Chem. Soc.*, 2005, 127, 12238. Braga and coworkers have reported the syntheses of hydrogen-bond directed organometallic and organic-organometallic supramolecules based on ferrocene, cobaltocene and bis-benzene chromium units. See: D. Braga, L. Maini and F. Grepioni, *Organometallics*, 2001, 20, 1875; D. Braga, G. Cojazzi, D. Emiliani, L. Maini and F. Grepioni, *Organometallics*, 2002, 21, 1315; D. Braga, M. Polito, D. D'Addario, E. Tagliavini, D. M. Proserpio, F. Grepioni and J. W. Steed, *Organometallics*, 2003, 22, 4532; D. Braga, M. Polito, M. Bracaccini, D. D'Addario, E. Tagliavini and L. Sturba, *Organometallics*, 2003, 22, 2142; D. Braga, M. Polito, D. D'Addario and F. Grepioni, *Cryst. Growth Des.*, 2004, 4, 1109; D. Braga, M. Polito and F. Grepioni, *Cryst. Growth Des.*, 2004, 4, 769. In the latter studies it was suggested that charge assisted hydrogen bonding, which can occur in ionic or zwitterionic systems and refers to hydrogen bonding accompanied by coulombic interactions resulting from the inherent electronic charges, can be an effective strategy for fully utilizing the directional properties of hydrogen-bonding mediated assembly. See: D. Braga and F. Grepioni, *Acc. Chem. Res.*, 2000, 33, 601.

The self-assembly of molecules or molecular units into supramolecular arrays can be driven by covalent bond formation and/or can be driven by noncovalent interactions such as π-π stacking, hydrogen bonding and van der Waals forces. Hydrogen bonding has been recognized as a particularly powerful tool in this regard because of its unique directionality and specificity. Supramolecular assemblies predicated on hydrogen bonding can be reinforced by the cooperative action of multi-point H-bonds, or additional cooperative interactions between the modular components of the assembly. An important example of this is so-called charge-assisted hydrogen bonding. This can lead to an exceptionally strong interaction between the oppositely charged components.

Recently, it has been recognized that the structural and chemical versatility of organometallic building blocks can be utilized to prepare supramolecular assemblies with distinct physical and chemical properties that cannot be replicated in purely organic systems. For example, self-assembled coordination networks that feature transition metal nodes and the anionic complex [(η$^4$-quinone)Mn(CO)$_3$]$^-$ as organometalloligand spacers have been extensively reported by us. See Sweigart, et al., *Accounts of Chemical Research*, 2004,37,1. In addition to coordination mediated self-assembly, there has been a considerable interest in supramolecular organometallic assemblies formed via non-covalent interactions. Braga and coworkers, referenced above, for example, have described the self-assembly of a variety of organometallic sandwich compounds through charge-assisted hydrogen bonding.

Figure 12:
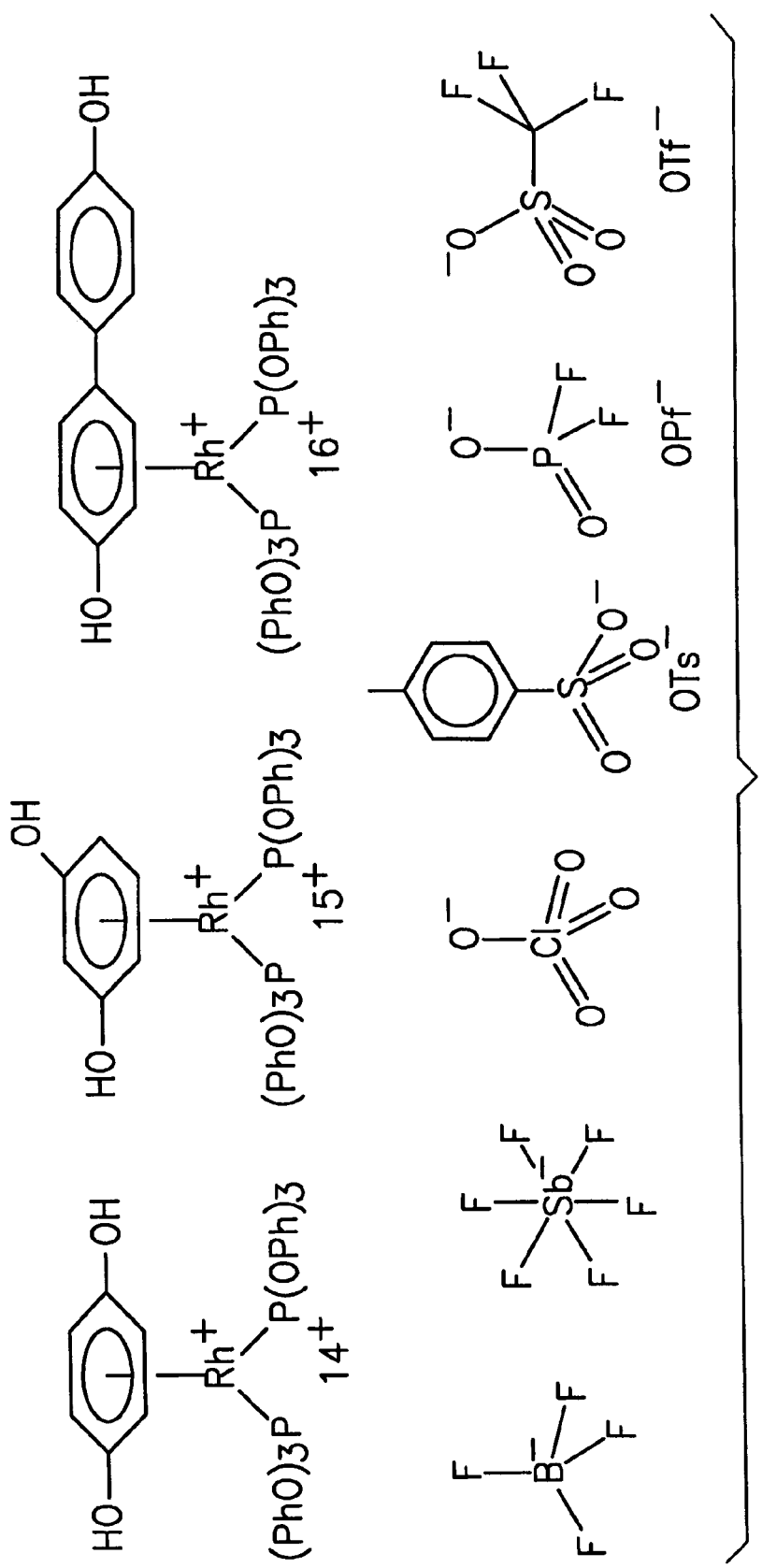
FIG. 12 shows cationic complexes and associated anions used to study the structural consequences charge assisted hydrogen bonding.

In this section, Applicants present the structural consequences of hydrogen bonding within the ionic organometallic complexes of the type [(η$^6$-hydroquinone)Rh(P(OPh)$_3$)$_2$]$^+$ X$^-$ (14$^+$; X=BF$_4$, ClO$_4$, SbF$_6$, OTf, OTs, OPf), [(η$^6$-resorcinol)Rh(P(OPh)$_3$)$_2$]$^+$BF$_4^-$ (15$^+$BF$_4^-$)and [(η$^6$-4,4'-biphenol)Rh(P(OPh)$_3$)$_2$]BF$_4$ (16$^+$BF$_4^-$). FIG. 12 illustrates the complexes. In these complexes, the —OH groups are activated by the electrophilic rhodium moiety to participate in charge-assisted hydrogen bonding to the anionic counterion. The crystal structures feature three kinds of non-covalent interactions: hydrogen bonding, coulombic attraction and π-π stacking, which result in an intriguing array of architectures: dimeric, 1-D chain, C$_2$-helical, and C$_3$ helical. The nature of the charge-assisted hydrogen bonding and the resulting 3-D structure in these systems is remarkably dependent on the identity of the anion. Robust porous networks are formed rapidly (minutes or less) with [(η$^6$-hydroquinone)Rh(P(OPh)$_3$)$_2$]$^+$X$^-$ (X=BF$_4$, ClO$_4$) and [(η$^6$-resorcinol)Rh(P(OPh)$_3$)$_2$]$^+$BF$_4$—. The hydrophobic pores in [(η$^6$-hydroquinone)Rh(P(OPh)$_3$)$_2$]ClO$_4$ bind toluene reversibly. This work demonstrates that self-assembly of well-designed organometallic building blocks via charge-assisted hydrogen bonding is an effective strategy for the construction of robust porous networks. With counterions containing both oxygen and fluorine, it was found that the former is invariably the hydrogen bond acceptor, a result in agreement with atomic charge calculations. It is anticipated that self-assembly via charge-assisted hydrogen bonding is an approach applicable to many organometallic systems.

Complexes 15$^+$BF$_4$ and 16$^+$BF$_4$ were synthesized in good yields by treatment of the precursor [Rh(P(OPh)$_3$)$_2$Cl]$_2$ with AgBF$_4$ in methylene chloride to generate [Rh(P(OPh)$_3$)$_2$]$^+$ in situ, which was then reacted with resorcinol and 4,4'-biphenol, respectively. The 1,4-hydroquinone salts 14$^+$X (X$^-$=BF$_4^-$, SbF$_6^-$, PF$_6^-$, ClO$_4^-$, OTs$^-$, Otf$^-$) were synthesized in a similar manner, with the anion X$^-$ deriving from the silver salt (AgX) utilized. The bulky phosphite ligands were introduced to minimize the probability of interpenetration in the solid state. Examples of the utilization of bulky groups to get non-interpenetrated porous structures include X. Xu, M. Nieuwenhuyzen and S. L. James, *Angew. Chem. Int. Ed.*, 2002, 41, 764; N. G. Pschirer, D. M. Ciurtin, M. D. Smith, U. H. F, Bunz and H. C. Zur Loye, *Angew. Chem. Int. Ed.*, 2002, 41, 583; B. Moulton and M. J. Zaworotko, *Curr. Opin. Sol. State Mat. Sci.*, 2002, 6, 117.

Figure 13:
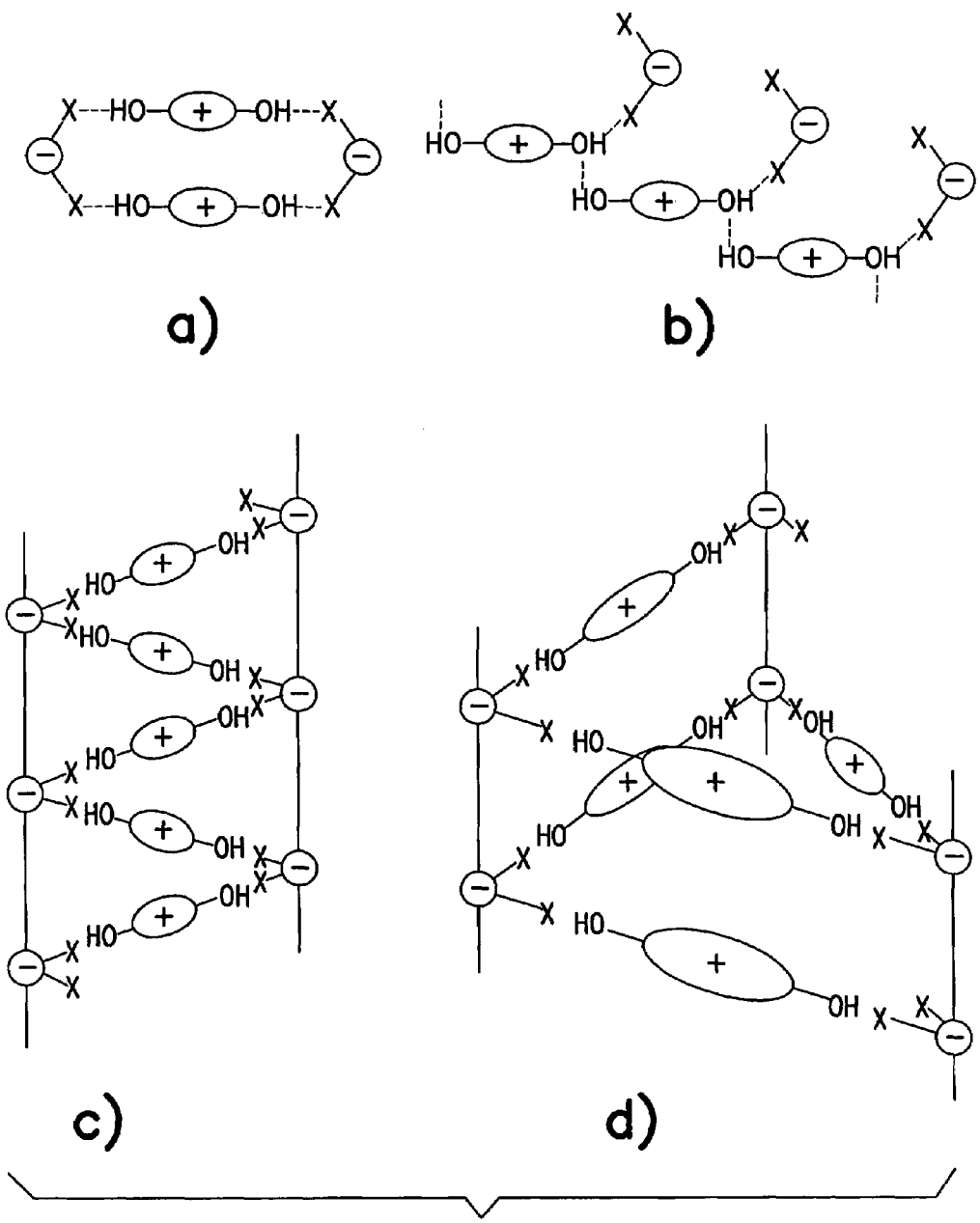
FIG. 13 shows hydrogen bonded structural patterns found in the solid state for [14$^+$-16$^+$]X$^-$ can be (a) dimeric, (b) 1-D chain, (c) C$_2$-helical, (d) C$_3$-helical.
Figure 14:
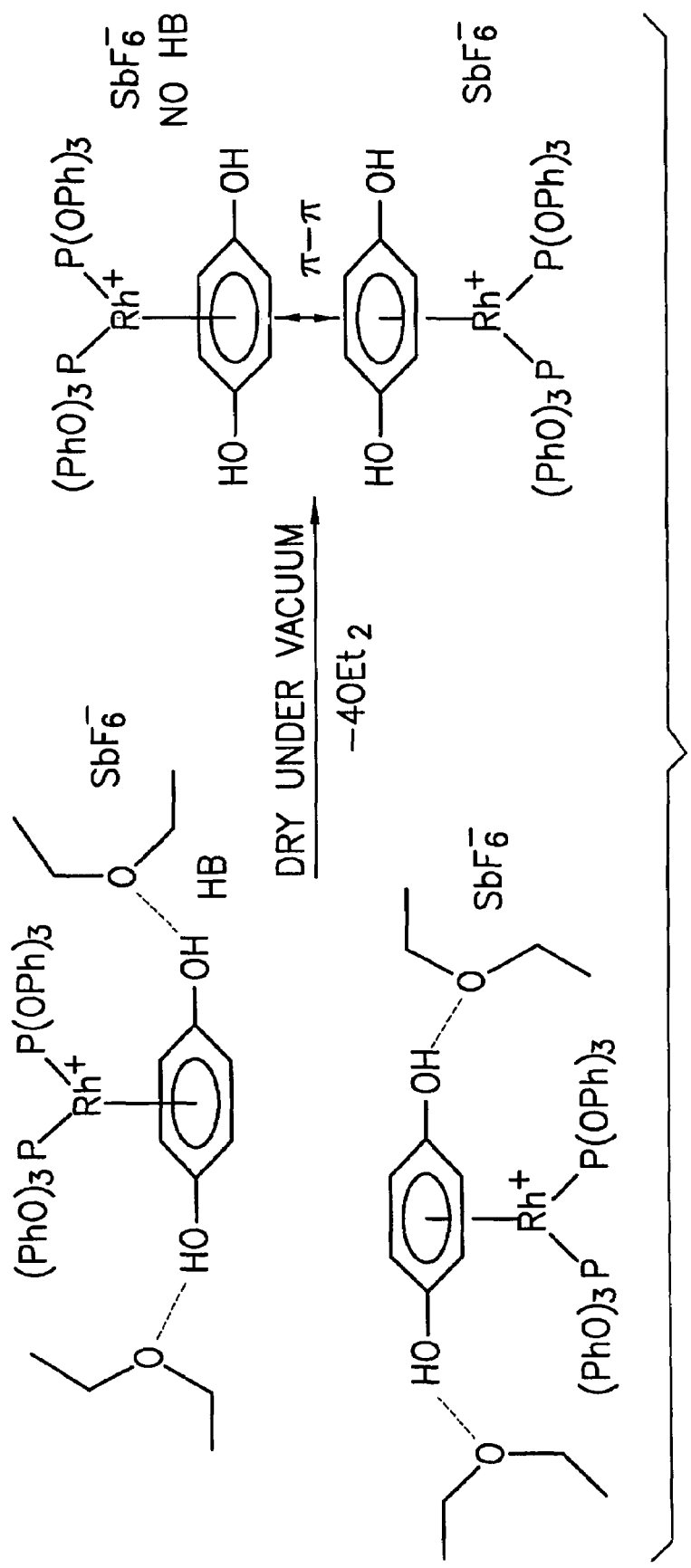
FIG. 14 shows hydrogen bonded structure of crystalline 14$^+$SbF$_6^-$ as a diethyl ether solvate (left) and slippage to a π-π stacked structure upon drying (right)

Cartoon diagrams of the different types of solid state structural patterns found are shown in FIG. 13. The cationic hydroxybenzene complexes (14$^+$-16$^+$) and the anionic companion (X$^-$) can assemble to generate dimeric, 1-D chain, C$_2$-helical or C$_3$-helical motifs, most of which feature charge-assisted hydrogen bonding. Relevant sample X-ray crystallographic data are summarized in Table 7.

Figure 19:
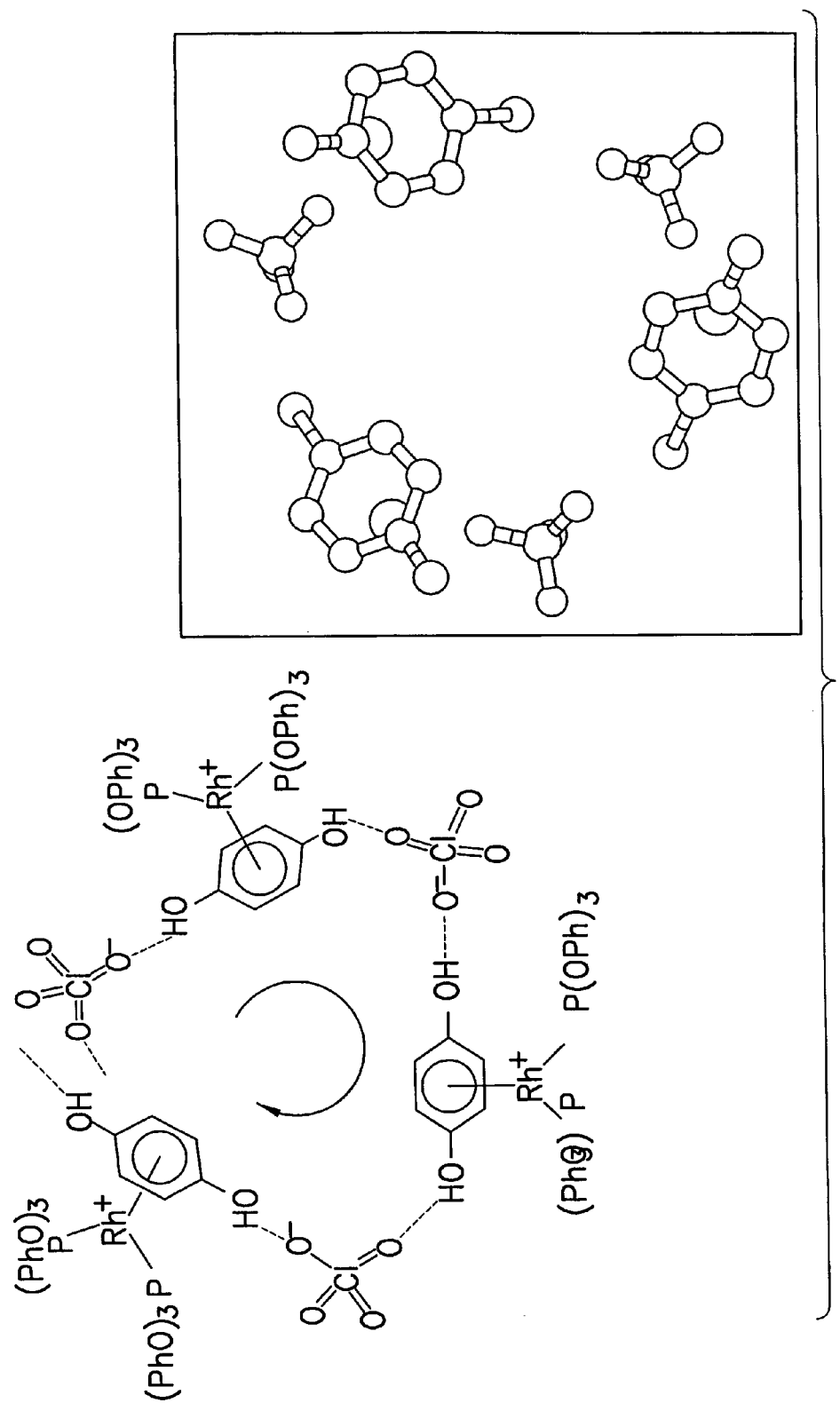
FIG. 19 shows the C$_3$ helical hydrogen bonded structure found in 14$^+$ClO$_4^-$ and 14$^+$BF$_4^-$.

Crystals of [(η$^6$-1,4-hydroquinone)Rh(P(OPh)$_3$)$_2$]$^+$SbF$_6^-$ (14$^+$SbF$_6^-$) suitable for the single crystal X-ray analysis were prepared by layering a methylene chloride solution at −20° C. with diethyl ether or hexane. Cubic-shaped orange crystals and plate-shaped yellow crystals were obtained with diethyl ether and hexane co-solvents, respectively. The X-ray structure of the orange crystals revealed that the hydroquinone —OH groups are hydrogen bonded to diethyl ether present in the crystal lattice (O . . . O=2.6 Å), as shown in FIG. 19 (left). The hydroquinone rings are arranged in pairs due to an edge-to-edge π-π stacking interaction involving two carbon atoms of each ring. The average C . . . C contact between the edges of adjacent rings is 3.3 Å. After drying under vacuum for one day, the XRPD (X-ray powder diffraction) pattern of 14$^+$SbF$_6^-$ changed significantly, from which it is inferred that the solid remains crystalline but undergoes a substantial structural change upon solvent loss. It proved possible to ascertain the nature of this change because the simulated XRPD obtained from single crystal data for 14$^+$SbF$_6^-$ grown with hexane co-solvent matched that obtained after drying 14$^+$SbF$_6^-$.2 Et$_2$O, suggesting that they have the same structure. The structure of the former, reveals a π-π stacked dimeric aggregate with nearly eclipsed hydroquinone rings that are separated by an average of 3.4 Å. It is concluded that, upon drying, 14$^+$SbF$_6^-$.2 Et$_2$O undergoes a remarkable concerted hydroquinone ring slippage of ca. 3 Å with concomitant loss of hydrogen bonding to the ether and gain of 7-7 stacking interactions, all without the loss of crystallinity.

TABLE 7

| | Crystallographic Data | | | |
|---|---|---|---|---|
| | 14+SbF6− | 14+SbF6−(hex) | 14+OTf− | 14+OPf− |
| formula | $C_{50}H_{56}F_6O_{10}P_2RhSb$ | $C_{42}H_{36}F_6O_8P_2RhSb$ | $C_{44}H_{38}Cl_2F_3O_{11}P_2RhS$ | $C_{42}H_{36}F_2O_{10}P_3Rh$ |
| fw | 1217.55 | 1069.31 | 1067.55 | 934.53 |
| T, K | 100(2) | 100(2) | 100(2) | 100(2) |
| cryst syst | Triclinic | Triclinic | Triclinic | Triclinic |
| space group | P-1 | P-1 | P1 | P1 |
| a, Å | 12.834(1) | 10.669(2) | 10.597(1) | 10.843(1) |
| b, Å | 13.259(1) | 14.186(3) | 13.952(1) | 11.245(1) |

TABLE 7-continued

Crystallographic Data

|  | 14+SbF6− | 14+SbF6−(hex) | 14+OTf− | 14+OPf− |
|---|---|---|---|---|
| c, Å | 17.158(1) | 16.884(3) | 16.587(1) | 17.908(1) |
| α, deg | 94.600(1) | 65.795(4) | 74.722(1) | 105.394(1) |
| β, deg | 99.863(1) | 85.774(4) | 84.604(2) | 90.398(1) |
| γ, deg | 116.234(1) | 70.863(4) | 70.769(1) | 107.279(1) |
| V, Å$^3$ | 2540(1) | 2196(1) | 2233(1) | 2001(1) |
| Z | 2 | 2 | 2 | 2 |
| $D_{calcd}$, g/cm$^3$ | 1.592 | 1.617 | 1.587 | 1.551 |
| F(000) | 1232 | 1064 | 1079 | 952 |
| cryst size, mm | 0.17 × 0.16 × 0.15 | 0.15 × 0.11 × 0.05 | 0.10 × 0.09 × 0.05 | 0.07 × 0.05 × 0.05 |
| θ range, deg | 1.74 to 28.42 | 1.65 to 26.47 | 1.60 to 26.45 | 1.98 to 26.55 |
| no. of rflns collected | 30290 | 23725 | 24103 | 21442 |
| no. of data/restraints/params | 12161/6/635 | 8995/0/541 | 17842/657/1123 | 16047/603/1020 |
| Goodness-of-fit on F$^2$ | 1.026 | 1.074 | 1.023 | 1.033 |
| final R indices [I>2σ(I)] | R1 = 0.0377 | R1 = 0.1121 | R1 = 0.0758 | R1 = 0.0688 |
|  | wR2 = 0.0808 | wR2 = 0.3021 | wR2 = 0.1221 | wR2 = 0.1385 |

|  | 16+BF4− | 14+OTs− | 14+ClO4− |
|---|---|---|---|
| formula | $C_{48}H_{40}BF_4O_8P_2Rh$ | $C_{50}H_{45}Cl_2O_{11}P_2RhS$ | $C_{42}H_{36}ClO_{12}P_2Rh$ |
| fw | 996.46 | 1089.67 | 933.01 |
| T, K | 100(2) | 293(2) | 100(2) |
| cryst syst | Monoclinic | Orthorombic | Rhombohedral |
| space group | P2/c | P2$_1$2$_1$2$_1$ | R-3 |
| a, Å | 17.960(5) | 11.947(6) | 38.625(1) |
| b, Å | 11.306(3) | 17.660(8) | 38.625(1) |
| c, Å | 23.267(7) | 24.201(11) | 15.096(1) |
| α, deg | 90 | 90 | 90 |
| β, deg | 105.502(5) | 90 | 90 |
| γ, deg | 90 | 90 | 120 |
| V, Å$^3$ | 4553(2) | 5106(4) | 19505(2) |
| Z | 4 | 4 | 18 |
| $D_{calcd}$, g/cm$^3$ | 1.454 | 1.417 | 1.43 |
| F(000) | 2032 | 2232 | 8568 |
| cryst size, mm | 0.14 × 0.14 × 0.10 | 0.135 × 0.11 × 0.038 | 0.12 × 0.114 × 0.096 |
| θ range, deg | 1.82 to 23.25 | 1.43 to 28.79 | 1.48 to 28.38 |
| no. of rflns collected | 35882 | 57426 | 77869 |
| no. of data/restraints/params | 6529/730/618 | 12656/6/606 | 10732/0/523 |
| Goodness-of-fit on F$^2$ | 1.067 | 0.735 | 0.930 |
| final R indices [I>2σ(I)] | R1 = 0.1212 | R1 = 0.0705 | R1 = 0.0762 |
|  | wR2 = 0.2917 | wR2 = 0.1151 | wR2 = 0.2386 |

Crystals of the triflate salt 14$^+$OTf were grown by layering hexane on a methylene chloride solution at −20° C. The solid state structure consists of the dimeric unit illustrated in FIG. 15 and follows the general pattern depicted in FIG. 13a. The two hydroquinone rings are π-π stacked (3.6 Å) and the —OH groups are hydrogen bonded to the sulfonate oxygens of the triflate anion (average O . . . O=2.65 Å). Since the sulfonate end of the triflate anion contains most of the net negative charge (vide infra), the hydrogen bonding would be expected to involve the oxygens rather than the fluorines, and may be classified as charge assisted.

The synthesis of 14$^+$PF$_6^−$, with AgPF$_6$ as the anion source, proceeded smoothly and gave a product with a satisfactory elemental analysis. After slow recrystallization from methylene chloride, however, it became evident from subsequent single crystal X-ray analysis and altered bulk elemental analysis that hydrolysis of the anion to PF$_2$O$_2^−$ (OPf) had occurred during the recrystallization process. The hydrolysis reaction probably stems from trace water and may have been accelerated by the acidic nature of the coordinated hydroquinone. Hydrolysis of PF$_6^−$ in this manner has been observed previously. See Kannan, S.; James, A. J.; Sharp, P. R., *Inorg. Chim. Acta,* 2003, 345, 8. The X-ray structure of 14$^+$OPf$^−$ (FIG. 20) is very similar to that found for 14$^+$OTf. Charge-assisted hydrogen bonding and π-π stacking (3.4 Å) interactions dominate the observed dimeric units. Careful analysis of the X-ray data confirmed that the hydrogen bonding from the hydroquinone —OH groups is to oxygen and not fluorine acceptors on the OPf$^−$ anion (average O . . . O=2.65 Å).

Figure 16:
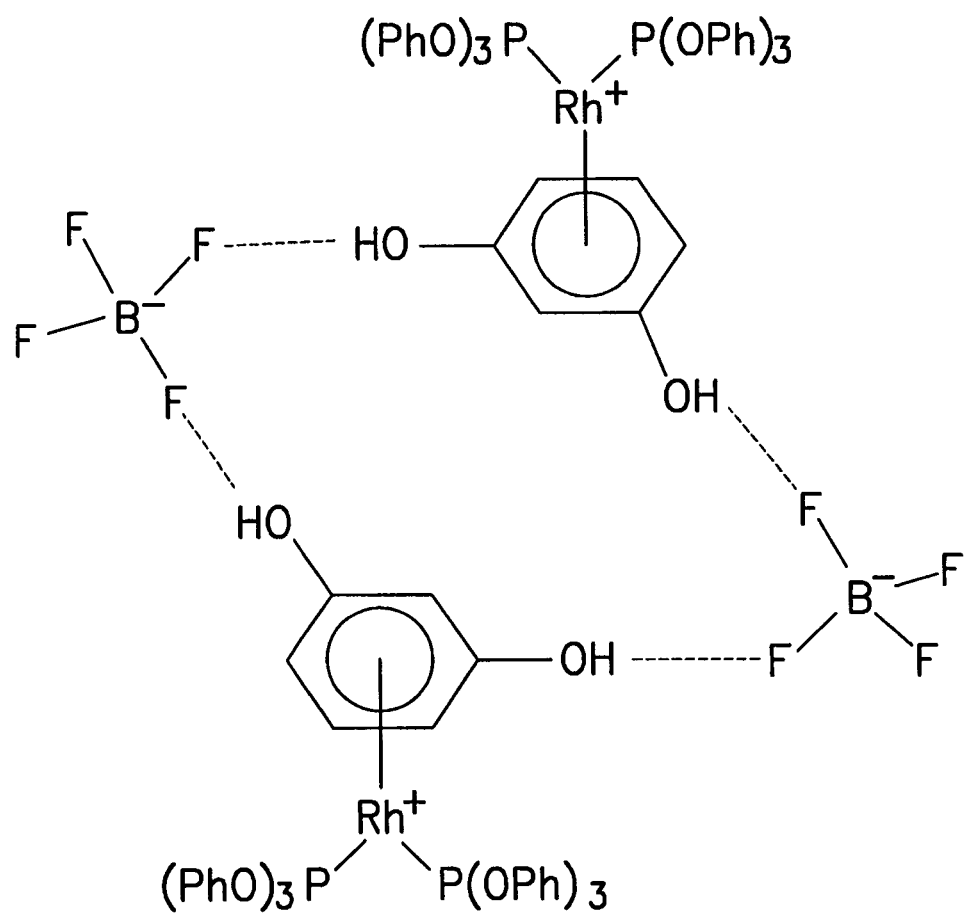
FIG. 16 shows the dimeric structure of 15$^+$BF$_4^-$.

The dimeric structure found for 14$^+$OPf$^−$ and 14$^+$OTf$^−$ combines in a cooperative manner three types of non-covalent interactions: charge-pairing, hydrogen bonding and π-π stacking. A different type of dimeric assembly was found for [(η$^6$-1,3-hydroquinone)Rh(P(OPh)$_3$)$_2$]$^+$BF$_4^−$ (15$^+$BF$_4^−$). In this case, the dimer is held together by charge-assisted hydrogen bonding but geometric restrictions prevent π-π stacking between the 1,3-hydroquinone rings (FIG. 16). The hydrogen bond distances in 15$^+$BF$_4^−$ average O . . . F=2.8 Å.

Figure 17:
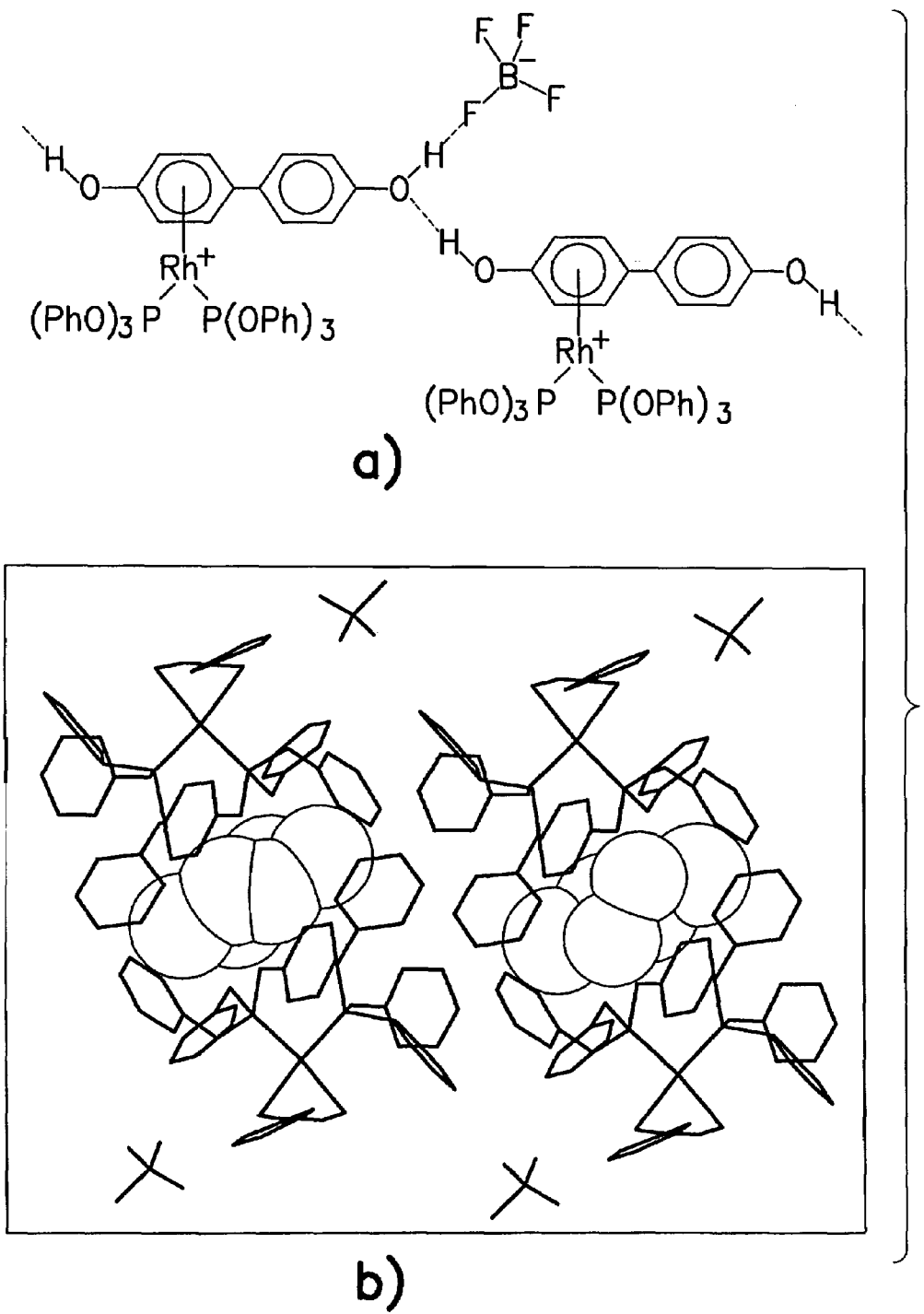
FIG. 17 shows (a) 1-D hydrogen bonded chain structure in 16$^+$BF$_4^-$ with (b) disordered solvent (violet) in channels that are lined with phenyl rings.
Figure 18:
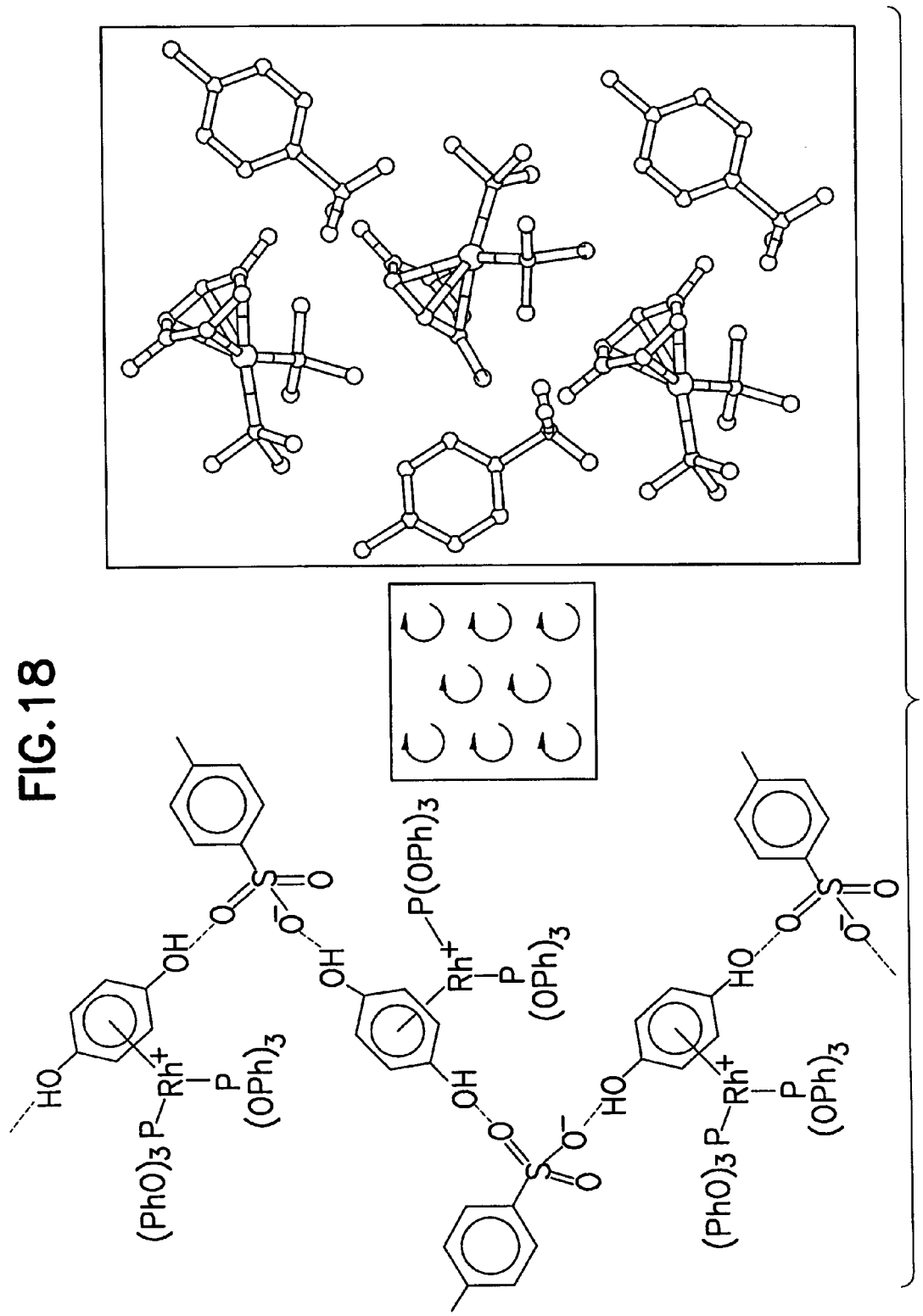
FIG. 18 showing the C$_2$ helical hydrogen bonded structure found in 14$^+$OTs$^-$. The helices all pack with the same twist direction, resulting in a chiral crystal.

[(η$^6$-4,4'-Biphenol)Rh(P(OPh)$_3$)$_2$]$^+$BF$_4^−$ (16$^+$BF$_4^−$) forms the hydrogen bonding network depicted in FIG. 18. Only one F atom in the BF$_4^−$ anion participates in hydrogen bond formation with the phenolic —OH groups. A 1-D polymeric chain structure results, shown in FIG. 17a, with the hydrogen bond distances O . . . F=2.6 Å and O . . . O=2.8 Å. The 3-D crystal structure features small channels which are lined with phenyl groups from the triphenyl phosphite ligands that undergo π-π stacking. The channels were found to be filled with unidentified disordered solvent molecules, (FIG. 17b).

The C$_2$-helical chain motif shown in FIG. 13c was found for the tosylate salt of [(η$^6$-1,4-hydroquinone)Rh (P(OPh)$_3$)$_2$]$^+$ (14$^+$OTs$^−$). Long rod-shaped single crystals of 14$^+$OTs$^-$ were grown by layering a methylene chloride solution with hexane at 0° C. The helical hydrogen bonding network has C$_2$ projection symmetry (FIG. 18). The space group (P2$_1$2$_1$2$_1$) implies the generation of chirality during the crystallization process, which means that the helices pack such that all possess the same direction of rotation (CW or CCW). The two independent hydrogen bonds in 14$^+$OTs$^-$ have O . . . O=2.43 and 2.67 Å.

Single crystals of 14$^+$BF$_4^-$ and 14$^+$ClO$_4^-$ were grown by layering a methylene chloride solution with diethyl ether. These two salts have virtually identical structures, which feature the intriguing C$_3$-helical hydrogen bonded network shown in FIG. 13$d$. Structural details for 14$^+$ClO$_4^-$ are shown in FIG. 19. The hydrogen bonding distances in 14$^+$BF$_4^-$ are F . . . O=2.47, 2.60 Å and those in 14+ClO$_4^-$ are O . . . O=2.41, 2.91 Å. In each compound, six C$_3$ helices assemble to generate the hexagonal channels or pores illustrated in FIG. 20. The structure belongs to the centrosymmetric space group R-3 and the direction of rotation of the helices alternates around the channels. The channels themselves located at the core of the six helices consist of hydrophobic phosphite phenyl groups (FIG. 20). Two of the three phenyl groups from each P(OPh)$_3$ ligand contribute to the channels, which have a diameter of ca. 10.5 Å and are separated by ca. 23 Å.

The ease of formation of the pore structure shown in FIG. 20$b$ for 14$^+$ClO$_4^-$ and 14$^+$BF$_4$ was investigated by comparing the XRPD pattern of slowly grown macrocrystals with that found for microcrystals obtained by rapid precipitation. The addition of diethyl ether to a methylene chloride solution of 14$^+$ClO$_4^-$ led to rapid precipitation of a powder that appeared under a microscope to consist of good quality microcrystals. XRPD patterns showed that microcrystalline 1+ClO$_4^-$ formed by simple rapid precipitation is (i) indeed crystalline and (ii) has the same porous structure possessed by slowly grown single crystals (FIG. 20). We come to the significant conclusion that the dynamic processes occurring in the assembly of organometallic building block 14+ClO$_4^-$ into an intricate 3-D supramolecular architecture with hexagonal channels operate on a fast preparative time scale. Thus, the synthesis of crystalline porous materials such as 14+ClO$_4^-$ can be accomplished within seconds (precipitation) rather than requiring days (slow single crystal growth). See also: Son UK Seung, Reingold Jeffrey A., Carpenter Gene B., Czech Paul T., Sweigart Dwight A., *Organometallics* 2006. Analogous conclusions obtain for the 14$^+$BF$_4^-$ analogue.

Experiments were done to probe the possible interaction of appropriate aromatic molecules with the hydrophobic channels present in 14+ClO$_4^-$ (FIG. 20). The XRPD pattern of solid 14+ClO$_4^-$ changes significantly after exposure to toluene for five days and then reverts to the original pattern after drying under vacuum. It may be concluded that toluene interacts reversibly with the host channels in 14+ClO$_4^-$.

Figure 21:
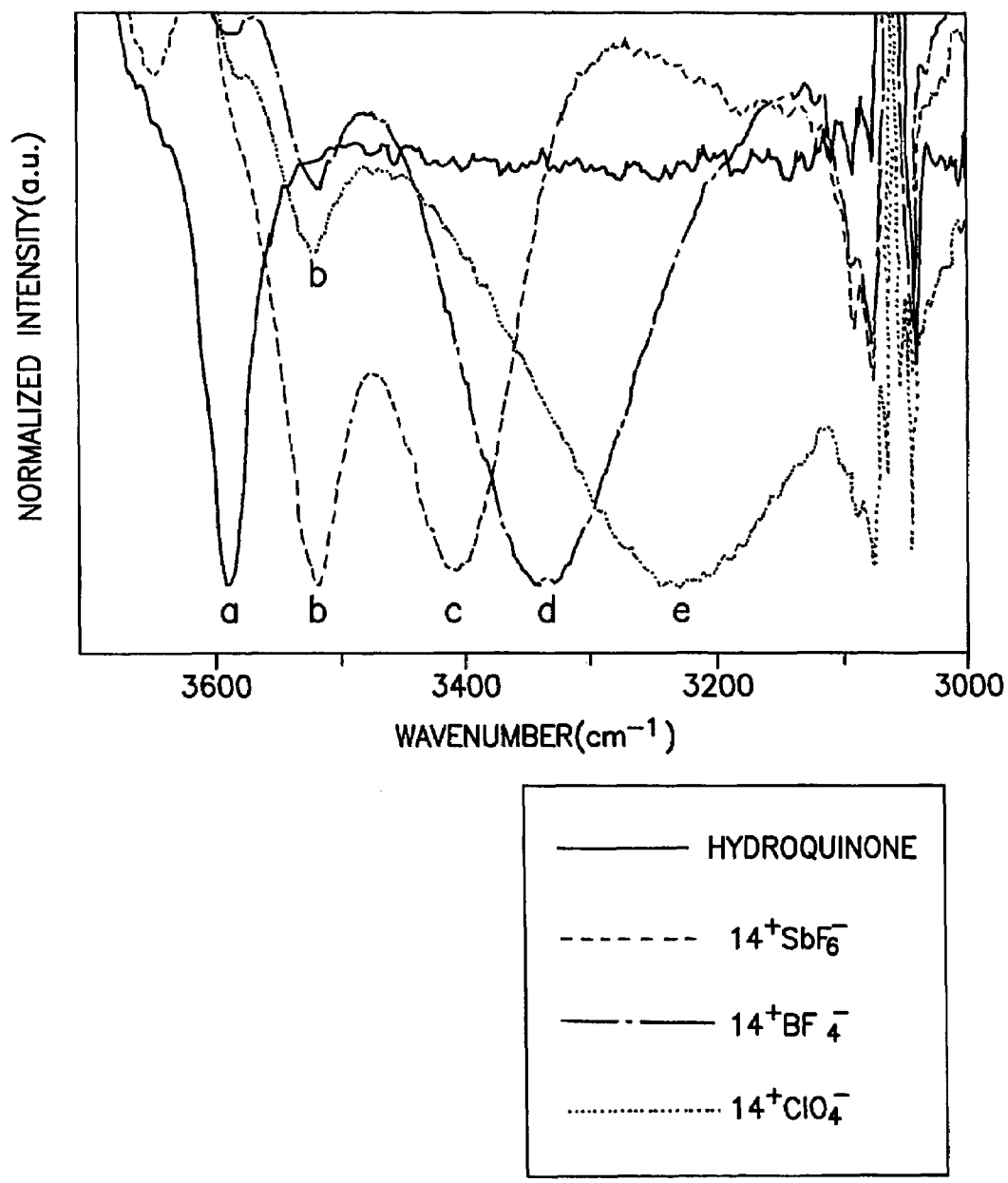
FIG. 21 shows IR spectra in the $v_{OH}$ region (11 mM, CH$_2$Cl$_2$ solvent) for (a) free 1,4-hydroquinone; (b) 14$^+$X$^-$ without hydrogen bonding between 14$^+$ and X$^-$; (c-e) 14$^+$X$^-$ with hydrogen bonding between 14$^+$ and the X$^-$.

The hydrogen bonding interactions between the organometallic cations and the counter anions shown in FIG. 12 were studied in methylene chloride solution via FT-IR. The results are summarized in FIG. 21 and in Table 8. As shown in FIG. 21, $v_{OH}$ in 14$^+$ is red-shifted by hydrogen bonding to the anion. With 14$^+$SbF$_6^-$, two IR peaks are seen at 3517 and 3405 cm$^{-1}$ (labeled b and c). The peak at 3517 cm$^{-1}$ is assigned to "free" 14$^+$, i.e., the complex not hydrogen bonded to the counter anion. In support of this assertion, peak "b" also appears at the same frequency with counterions BF$_4^-$ and ClO$_4^-$. The much greater intensity of this peak in the case of SbF$_6^-$ reflects the relatively poor ability of SbF$_6^-$ to function as a hydrogen bond acceptor, a fact also indicated by the X-ray structures.

Peaks c-e in FIG. 21 are assigned to hydrogen bonded —OH groups. The shift of these $v_{OH}$ bands from the "free" position (peak b) can be used to estimate the strength of the H-bonding between the hydroquinone —OH groups and the counterion by application of Iogansen's equation. It is noted that the Iogansen equation related to hydrogen bonding enthalpy is ΔHo=−1.28(Δv)½. See also S. G. Kazarian, P. A. Hamley and M. Poliakoff, *J. Am. Chem. Soc.*, 1993, 115, 9069; A. V. Iogansen, G. A. Kurkchi, V. M. Furman, V. P. Glazunov and S. E. Odinokov, *Zh. Prikl. Spektrosk.*, 1980, 33, 460. The results, presented in Table 8, indicate that H-bonding between 14$^+$ or 15$^+$ and the counter anion is greater for O-based acceptors than for F-based acceptors. The hydrogen bonding strength spans the range 14-27 kJ/mol and follows the order SbF$_6^-$<BF$_4^-$<ClO$_4^-$≦OTf$^-$≦OPf$^-$, OTs$^-$.

TABLE 8

Summary of IR Study of Hydrogen Bonding[a]

| Compound | Free $v_{OH}$ (cm$^{-1}$) | H-bonded $v_{OH}$ (cm$^{-1}$) | Shift in $v_{OH}$ (cm$^{-1}$) | −ΔH[b] (kJ/mol) |
|---|---|---|---|---|
| hydroquinone | 3585[c] | | | |
| resorcinol | 3580 | | | |
| 4,4'-biphenol | 3598 | | | |
| 1$^+$ClO$_4^-$ | 3517[d] | 3231 | 286 | 21.6 |
| 1$^+$OTf | 3517[d] | 3170 | 347 | 23.8 |
| 1$^+$OPf | 3517[d] | 3078 | 439 | 26.8 |
| 1$^+$OTs$^-$ | 3517[d] | 3058 | 459 | 27.4 |
| 1$^+$BF$_4^-$ | 3517[d] | 3330 | 187 | 17.5 |
| 1$^+$SbF$_6^-$ | 3517[d] | 3405 | 112 | 13.5 |
| 2$^+$BF$_4^-$ | 3505[d] | 3321 | 184 | 17.4 |
| 3$^+$BF$_4^-$ | 3573[e] | 3296 | | |

[a]Data obtained using 11 mM solutions in methylene chloride.
[b]Calculated with Iogansen equation[17].
[c]Peak unchanged in 3 mM solution.
[d]$v_{OH}$ peak in coordinated hydroquinone which is not hydrogen-bonded.
[e]The $v_{OH}$ peak in uncoordinated phenol ring.

The $v_{OH}$ bands in the IR spectra of free hydroquinone, resorcinol and 4,4'-biphenol were found to be invariant over the concentration range utilized (3-11 mM), indicating the absence of intermolecular hydrogen bonding at these concentrations. In contrast, FIG. 21 clearly shows that hydrogen bonding in 14$^+$X$^-$ can be extensive at 11 mM. The enhanced hydrogen bonding in 14$^+$X$^-$ can be attributed to (1) the positive charge on the cation brought about by the electrophilic rhodium fragment and (2) the obligatory anionic counterion that can act as a hydrogen bond acceptor. Charge pairing of the species in 14$^+$X$^-$ undoubtedly complements the hydrogen bonding. In order to probe the "charge assisted" nature of the hydrogen bonding, IR spectra of CH$_2$Cl$_2$ solutions of 1,4-hydroquinone (11 mM) containing varying amounts of Bu$_4$ClO$_4$ were recorded. One equivalent of Bu$_4$NClO$_4$ has little effect on the IR spectrum and even with ten equivalents of Bu$_4$NClO$_4$ present, a significant amount of free hydroquinone remains. It is concluded that the hydrogen bonding observed with (14$^+$-16$^+$), X$^-$ has as important components both ionic charge pairing and electrophilic activation imparted by coordination to the transition metal.

Next, molecular orbital calculations were performed using Spartan to assign atomic charges to the key terminal atoms for the range of counterions. Atomic charges are notoriously difficult to define which led us to include the results from three differing approaches. See Spartan '04, Version 1.0.3; Wavefunction, Inc., Irvine, Calif. 2004 and Hehre, W. J. *A Guide to Molecular Mechanics and Quantum Chemical Calcultions*, Chapter 16, Wavefunction, Inc., Irvine Calif. 2003. Regardless of the charge partitioning scheme used, the oxygen atoms are calculated to be more electron-rich than the fluorine atoms. These results are in agreement with the observed preference for charge-assisted hydrogen-bonding to oxygen over fluorine in OTf⁻ and OPf⁻, as well as the trends observed in the IR spectra.

In crystal engineering, it is common for slight modification in ligand geometry and/or reaction conditions to result in supramolecular isomerization. This is typically the reason it is difficult to rationally design or predict supramolecular structures. In the case of $14^+BF_4^-$ and $15^+BF_4^-$ it is interesting that two iso-structures can be obtained from the self-assembly of geometrically different building blocks. This suggests that the bulky triphenyl phosphite groups, which are common to $14^+BF_4^-$, $14+ClO_4^-$ and $15^+BF_4^-$, play a major role in the supramolecular construction. This hypothesis is strengthened by an examination of the chemical composition of the channels.

Figure 22:
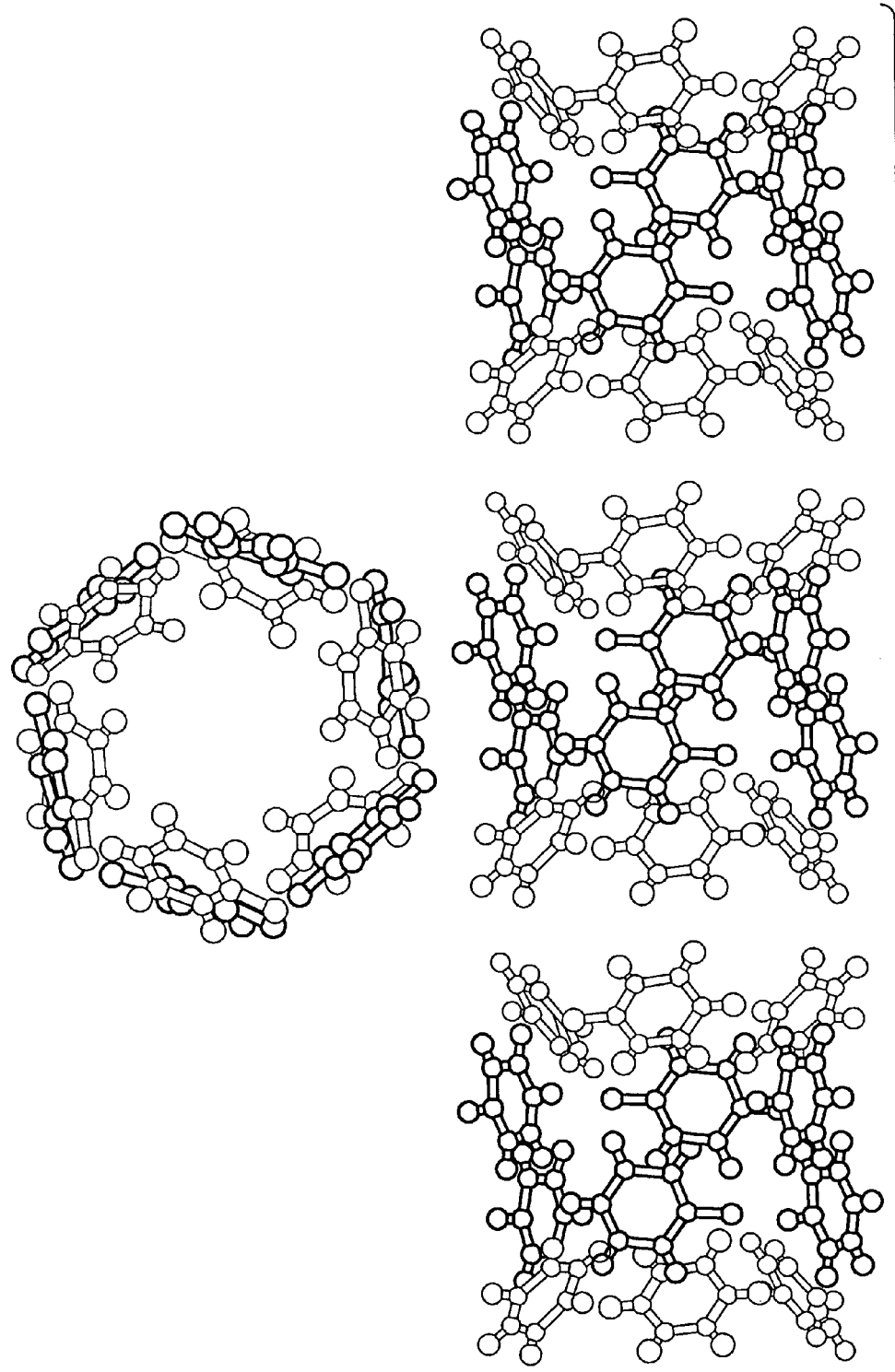
FIG. 22 shows views perpendicular and parallel to the channel axis in 14$^+$BF$_4^-$; two types of phenyl groups are shown.

The channels or pores located at the core of the six helices in $14^+BF_4^-$ and in $14^+ClO_4^-$ include hydrophobic phosphite phenyl groups (FIG. 20). Two of the three phenyl groups from each $P(OPh)_3$ ligand contribute to the channels. FIG. 22 illustrates the view perpendicular and parallel to the channel axis. There are two types of phenyl groups present: half are situated parallel to the channel axis and define a pore diameter of ca. 10.5 Å; the other half are inclined by ca. 45° to the axis, reducing the effective pore diameter to ca. 6 Å. These two subgroups together form interesting sphere like units linked by linear units. In $15^+BF_4^-$ completely analogous channels exist with the difference that the phenyl groups are more inclined (ca. 75°), with the result that the channels are much more blocked in comparison to the situation in $14^+BF_4^-$ and $14+ClO_4^-$.

The micropores in $14^+BF_4^-$ are likely to be robust because the hydrogen bonding is "charge-assisted" by coulombic interactions. Complementing this is the relatively small pore size and the large distance of ca. 23 Å between successive pore centers. See: B. Moulton and M. J. Zaworotko, *Curr. Opin. Sol. State Mat. Sci.*, 2002, 6, 117. Metal-organic networks with pores in the size range reported herein have recently been found to be excellent hosts for suitably small guest molecules (e.g., acetylene). Aside from size the important factor influencing adsorption is the chemical environment of the pore interior. In the case of $14^+BF_4^-$ and $14+ClO_4^-$, the channels or pores consist of aromatic rings, which may make the material a particularly useful model for hydrogen adsorption. See: B. Kesanli, Y. Cui, M. R. Smith, E. W. Bittner, B. C. Bockrath and W. Lin, *Angew. Chem. Int. Ed.*, 2005, 44, 72.

In summary, the complexes [(1,4- and 1,3-hydroquinone) Rh(P(OPh)$_3$)$_2$]BF$_4$ ($14^+BF_4^-$, $15^+BF_4^-$) were found to exhibit charge assisted hydrogen bonding between the —OH groups and the BF$_4^-$ or ClO$_4^-$ counterion. In the solid state, this hydrogen bonding interaction gives rise to iso-structural supramolecular networks containing hydrophobic channels that consist of phenyl groups from the triphenyl phosphite ligands. Applications of these materials to guest-host chemistry are being examined.

Additionally, porous media for gas storage has potential applications in the development of hydrogen storage systems. Rhodium quinones are not believed to have been used before for this purpose. The rhodium hydroquinone cationic complex [(hydroquinone)RhL$_2$]$^+$X$^-$ has a solid state structure that is dominated by charge assisted hydrogen bonding and pi-pi stacking of the aromatic rings. With anions such as tetrafluoroborate and perchlorate, the solid material possesses hydrophobic channels that are lined with aromatic rings and that may provide an excellent environment for modeling the storage of hydrogen gas for application in storage and transport for energy applications.

It is further noted that additional crystallographic (CIF) data have been deposited with the Cambridge Crystallographic Data Center as registry numbers CCDC 285472, 285473 and 299584-299590. See Table 8 for crystal data. Additional data are as follows: for $14^+BF_4^-$: $C_{42}H_{36}O_8P_2B_1F_4Rh_1$, M=920.37, rhombohedral, space group R-3, a=38.46(1), b=38.46(1), c=14.93(1) Å, α=90, β=90, γ=120°, V=19125(2)Å$^3$, Z=18, F(000)=8424, gof=0.855, final R1=0.0743; Crystal Data for $15^+BF_4^-$: $C_{42}H_{36}O_8P_2B_1F_4Rh_1$, M=920.37, rhombohedral, space group R-3, a=38.72(1), b=38.72(1), c=14.66(1) Å, α=90, β=90, γ=120°, V=19037(4)Å$^3$, Z=18, F(000)=8424, gof=1.098, final R1=0.0895

Synthetic Procedures and Characterization

General Considerations All reactions were carried out under N$_2$ in flame-dried glassware. HPLC grade methylene chloride and diethyl ether solvents were used as received without further purification. [Rh(COD)Cl]$_2$ was provided by Strem Chemicals. The $^1$H NMR spectra were recorded on Bruker (300 MHz) spectrometers. Elementary analyses were performed by Quantitative Technologies Inc. (QTI, New Jersey). Thermogravimetric analyses (TGA, Q500 from Texas Instruments) and differential scanning calorimetry (DSC, DuPont DSC 2910) were performed at a scan rate of 5° C./min and 10° C./min using N$_2$, respectively. X-ray powder diffraction (XRPD) data were recorded on a Bruker D8 ADVANCE at 40 kV and 40 mA with Cu Kα radiation (k=1.54050 Å) and a scan speed of 0.3°/sec and a step size of 0.1° in 2θ.

($\eta^6$-1,4-Hydroquinone)Rh[bis(triphenylphosphite)]BF$_4$ ($14^+BF_4^-$). After flame drying the glassware, [Rh (P(OPh)$_3$)$_2$Cl]$_2$ (0.36 g, 0.24 mmol) and AgBF$_4$ (0.11 g, 0.56 mmol) were mixed for 1 h at room temperature in methylene chloride (5 mL). While stirring, a white precipitate was formed on the bottom of the glassware. 1,4-hydroquinone (0.10 g, 0.91 mmol) was added to the reaction mixture. After stirring for 2 h at r.t., the solvent was removed using rotary evaporator. The residue was dissolved in methylene chloride (3 mL) and slowly dropped to ethereal solution trough the Celite pad. The formed yellow solid in ether was collected by filter and washed with diethyl ether (10 mL, three times). The isolated yield was 71% (0.31 g, 0.34 mmol). To get the crystals: $\eta^6$-1,4-hydroquinone Rh[bis(triphenylphosphite)]$^+$ BF$_4^-$ (30 mg) was dissolved in methylene chloride (1.0 mL) in 5 mL-vial. Diethylether (3 mL) was carefully added to upper layer. After standing in a refrigerator for 3 days, reddish-yellow crystals formed on the wall of vial. $^1$H NMR (CD$_2$Cl$_2$): δ 7.36(t, J=7.8 Hz, OPh, 12H) 7.26 (t, J=7.6 Hz, OPh, 6H), 7.02 (d, J=8.0 Hz, OPh, 12H), 6.56 (brs, OH, 2H), 5.63 (s, hydroquinone ring, 4H) ppm. Elemental Anal. Calcd for C$_{42}$O$_8$H$_{36}$P$_2$Rh$_1$B$_1$F$_4$: C, 54.81; H, 3.94. Found: C, 54.66; H, 3.86.

($\eta^6$-1,4-Hydroquinone)Rh[bis(triphenylphosphite)]ClO$_4$ ($14^+ClO_4^-$). The same procedure was followed using AgClO$_4$ instead of AgBF$_4$. The isolated yield was 79%. Crystals of $14^+ClO_4^-$ were grown by layering a methylene chloride solution with hexane and cooling in a refrigerator for four days. $^1$H NMR (CD$_2$Cl$_2$): δ 7.37(t, J=7.9 Hz, OPh, 12H), 7.25 (t, J=7.8 Hz, OPh, 6H), 7.01 (d, J=7.8 Hz, OPh, 12H), 6.96 (br s, OH, 2H), 5.67 (s, hydroquinone ring, 4H). Elemental anal. Calcd (%) for C$_{42}$O$_{12}$H$_{36}$P$_2$Rh$_1$Cl$_1$: C, 54.07; H, 3.89. Found (%): C, 54.08; H, 4.01.

($\eta^6$-1,4-Hydroquinone)Rh[bis(triphenylphosphite)]SbF$_6$ ($14^+SbF_6^-$). After flame drying the glassware, [Rh(P (OPh)₃)₂Cl]₂ (0.36 g, 0.24 mmol) and AgSbF₆ (0.19 g, 0.56 mmol) were mixed for 1 h at room temperature in methylene chloride (5 mL). While stirring, a white precipitate formed on the bottom of the glassware after which 1,4-hydroquinone (0.10 g, 0.91 mmol) was added to the reaction mixture. After stirring for 2 h at RT, the solvent was removed by rotary evaporation. The residue was dissolved in methylene chloride (3 mL) and slowly dropped into an ether solution through a Celite pad. A yellow solid formed in the ether solution and was collected by filtration (washed with diethyl ether, 10 mL, three times). The isolated yield was 83% (0.42 g, 0.39 mmol). Crystals were grown by dissolving 14⁺SbF₆⁻ (30 mg) in methylene chloride (1.0 mL) in a 5 mL-vial and layering with 3 mL of diethyl ether. The solution was placed in a refrigerator for 2 weeks, after which yellow crystals formed on the wall of the vial. ¹H NMR (CD₂Cl₂): δ 7.37(t, J=7.8 Hz, OPh, 12H), 7.27 (t, J=7.6 Hz, OPh, 6H), 7.03 (d, J=7.8 Hz, OPh, 12H), 6.11 (br s, OH, 2H), 5.68 (s, hydroquinone ring, 4H). Elemental anal. calcd (%) for $C_{42}O_8H_{36}P_2Rh_1Sb_1F_6$: C, 47.18; H, 3.39. Found: C, 47.85; H, 3.48.

(η⁶-1,4-Hydroquinone)Rh[bis(triphenylphosphite)] TfO (14⁺OTf). The same procedure as above was followed using AgTf instead of AgSbF₆. The isolated yield was 91%. Crystals of 14⁺OTf were grown by layering a methylene chloride solution with hexane and cooling in a refrigerator for two days. Yellow crystals formed on the wall of vial. ¹H NMR (CD₂Cl₂): δ 8.26 (br s, OH, 2H), 7.31 (t, J=8.0 Hz, OPh, 12H), 7.21 (t, J=7.9 Hz, OPh, 6H), 6.97 (d, J=8.0 Hz, OPh, 12H), 5.47 (s, hydroquinone ring, 4H). Elemental anal. calcd (%) for $C_{43}O_{11}H_{36}P_2Rh_1S_1F_3$: C, 52.56; H, 3.69. Found (%): C, 53.08; H, 3.63.

(η⁶-1,4-Hydroquinone)Rh[bis(triphenylphosphite)] PF₂O₂ (14⁺OPf). The same procedure as above was followed using AgPF₆ instead of AgSbF₆. Before recrystallization, the complex had PF₆⁻ as the counter anion. Elemental anal. calcd (%) for $C_{42}O_8H_{36}P_3Rh_1F_6$: C, 51.55; H, 3.71. Found (%): C, 52.04; H, 3.69. During recrystallization from methylene chloride, however, hydrolysis of the anion to PF₂O₂⁻ (OPf) occurred to afford 14⁺OPf⁻ in a 66% isolated yield. ¹H NMR (CD₂Cl₂): δ 9.59 (brs, OH, 2H), 7.37 (t, J=8.0 Hz, OPh, 12H), 7.20 (t, J=7.9 Hz, OPh, 6H), 6.98 (d, J=8.0 Hz, OPh, 12H), 5.50 (s, hydroquinone ring, 4H). Elemental anal. Calcd (%) for $C_{42}O_{10}H_{36}P_3Rh_1F_2$: C, 53.98; H, 3.88. Found (%): C, 53.50; H, 3.73.

(η⁶-1,4-Hydroquinone)Rh[bis(triphenylphosphite)]OTs (14⁺OTs⁻). The same procedure was followed using silver tosylate instead of AgSbF₆. The isolated yield was 95%. Crystals of 14⁺OTs⁻ were grown by layering a methylene chloride solution with hexane and cooling in a refrigerator for three days. ¹H NMR (CD₂Cl₂): δ 7.38 (d, J=7.5 Hz, OTs, 2H), 7.27 (t, J=7.8 Hz, OPh, 12H), 7.25 (d, J=7.5 Hz, OTs, 2H), 7.15 (t, J=7.6 Hz, OPh, 6H), 6.95 (d, J=7.8 Hz, OPh, 12H), 6.69 (br s, OH, 2H), 5.55 (s, hydroquinone ring, 4H), 2.39 (s, OTs methyl, 3H). Elemental anal. Calcd (%) for $C_{50}O_{11}H_{43}P_2Rh_1S_1$: C, 54.81; H, 3.94. Found (%): C, 54.66; H, 3.86.

(η⁶-Resorcinol)Rh[bis(triphenylphosphite)]BF₄ (14⁺BF₄). The same procedure as above was followed but using resorcinol instead of hydroquinone. The isolated yield was 89%. To get the crystals: (η⁶-resorcinol)Rh[bis(triphenylphosphite)]+BF₄⁻ (25 mg) was dissolved in methylene chloride (0.7 mL) in a 5 mL vial. Toluene (3 mL) was carefully added to upper layer. The solution stands in refrigerator for 3 days. The orange crystals were formed on the wall of vial. ¹H NMR (CD₂Cl₂): δ 8.41 (brs, OH, 2H), 7.35 (t, J=7.8 Hz, protons in OPh, 12H), 7.25 (t, J=7.6 Hz, OPh, 6H), 7.02 (t, J=7.00, resorcinol, 1H), 7.00 (d, J=7.8 Hz, OPh, 12H), 6.31 (s, resorcinol, 1H), 4.88 (d, J=7.8 Hz, resorcinol, 2H) ppm. Elemental Anal. Calcd for $C_{42}O_8H_{36}P_2Rh_1B_1F_4$: C, 54.81; H, 3.94. Found: C, 54.55; H, 4.10.

(η⁶-4,4-Biphenol)Rh[bis(triphenylphosphite)]BF₄ (16⁺BF₄⁻). The same procedure was as above was followed using 4,4-biphenol instead of hydroquinone. The isolated yield was 87%. Crystals of 16⁺BF₄⁻ were grown by layering a methylene chloride solution with hexane and cooling in a refrigerator for three days. Orange crystals formed on the wall of vial. ¹H NMR (CD₂Cl₂): δ 8.39 (br s, OH, 1H), 7.26 (t, J=7.5 Hz, OPh, 12H), 7.22 (t, J=7.5 Hz, OPh, 6H), 6.90 (t, J=7.6 Hz, OPh, 6H), 6.83 (d, J=8.9 Hz, biphenol, 2H), 6.75 (d, J=6.75 Hz, biphenol, 2H), 6.00 (br s, OH, 1H), 5.92 (s, biphenol, 4H). Elemental anal. Calcd (%) for $C_{48}O_8H_{40}P_2Rh_1B_1F_4$: C, 57.86; H, 4.05. Found (%): C, 57.74; H, 3.91.

Single Crystal X-ray Structure. X-ray data collection was carried out using a Bruker single-crystal diffractometer equipped with an APEX CCD area detector and controlled by SMART version 5.0. Collection was done either at 100 K or 293K. Data reduction was performed by SAINT version 6.0. The structures were generally determined by direct methods and refined on F squared by use of programs in SHELXTL version 5.0. Most hydrogen atoms appeared in a difference map, or they were generally inserted in ideal positions, riding on the atoms to which they are attached.

In view of the foregoing, it can be seen that novel embodiments include the combination of rhodium and quinones for use in catalysis, use in generation of new organolithium reagents and use as porous media for possible gas storage. Only a few rhodium quinones have been previously reported and none with the chemical formula or constitution set forth herein, and none that are believed to have been applied or are believed likely to be useful for any of the uses mentioned above. The rhodium and quinone components both play an integral role in the uses. In catalysis, the compounds function as multifunctional catalysts, which is also believed to be unique, in that the quinone part binds to a substrate while the rhodium center acts as a receptor site for a second substrate.

In conclusion, it should be noted that some of the features of the various non-limiting embodiments of this invention may be used to advantage without the corresponding use of other features. As such, the foregoing description should be considered as merely illustrative of the principles, teachings and exemplary embodiments of this invention, and not in limitation thereof. Also, the numerical values, such as temperature, weight percent, etc., may also be understood in approximate (about) values.

What is claimed is:

1. A rhodium quinonoid catalyst or catalyst precursor comprising the formula (I)

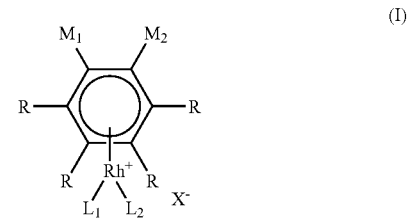

wherein X⁻ is selected from the group consisting of BF₄⁻, SbF₆⁻, PO₂F₂⁻, PF₆⁻, OTf⁻, ⁻OTs, SO₄²⁻, B(C₆F₅)₄⁻, B(C₆H₅)₄⁻, ClO₄⁻, NO₃⁻, NO₂⁻, HOSO₃⁻, CO₃²⁻, O₃SCF₂CF₂CF₂CF₃⁻ wherein OTf=$O_3SCF_3^-$; OTs=$O_3SC_6H_4CH_3^-$; R'$CO_2^-$;

wherein R' is selected from the group consisting of hydrogen or an alkyl, aryl or carbon atom bearing three identical or non-identical substituents;

wherein $L_1$ and $L_2$ are each a ligand that donates electron density to rhodium to stabilize it;

wherein

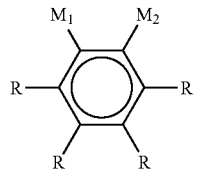

is either chiral or achiral and $M_1$ and $M_2$ are OH and R is selected from the group consisting of H, C, O, N and S, with or without substituents, said substituents being identical or non-identical.

2. A rhodium quinonoid catalyst or catalyst precursor of comprising the formula (II)

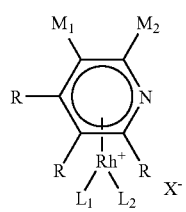

(II)

wherein $X^-$ is selected from the group consisting of $BF_4^-$, $SbF_6^-$, $PO_2F_2^-$, $PF_6^-$, OTf$^-$, $^-$OTs, $SO_4^{2-}$, $B(C_6F_5)_4^-$, $B(C_6H_5)_4^-$, $ClO_4^-$, $NO_3^-$, $NO_2^-$, $HOSO_3^-$, $CO_3^{2-}$, $O_3SCF_2CF_2CF_2CF_3^-$ wherein OTf=$O_3SCF_3^-$; OTs=$O_3SC_6H_4CH_3^-$; R'$CO_2^-$;

wherein R' is selected from the group consisting of hydrogen or an alkyl, aryl or carbon atom bearing three identical or non-identical substituents;

wherein $L_1$ and $L_2$ are each a ligand that donates electron density to rhodium to stabilize it;

wherein R is selected from the group consisting of H, C, O, N and S, with or without substituents, said substituents being identical or non-identical.

3. A rhodium quinonoid catalyst or catalyst precursor comprising formula (III)

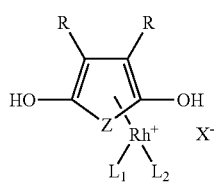

wherein Z is nitrogen, oxygen or sulfur;

wherein R is selected from the group consisting of H, C, O, N and S, with or without substituents, said substituents being identical or non-identical;

wherein $X^-$ is selected from the group consisting of $BF_4^-$, $SbF_6^-$, $PO_2F_2^-$, $PF_6^-$, OTf$^-$, $^-$OTs, $SO_4^{2-}$, $B(C_6F_5)_4^-$, $B(C_6H_5)_4^-$, $ClO_4^-$, $NO_3^-$, $NO_2^-$, $HOSO_3^-$, $CO_3^{2-}$, $O_3SCF_2CF_2CF_2CF_3^-$ wherein OTf=$O_3SCF_3^-$; OTs=$O_3SC_6H_4CH_3^-$; R'$CO_2^-$;

wherein R' is selected from the group consisting of hydrogen or an alkyl, aryl or carbon atom bearing three identical or non-identical substituents;

wherein $L_1$ and $L_2$ are each a ligand that donates electron density to rhodium to stabilize it;

or formula (IV)

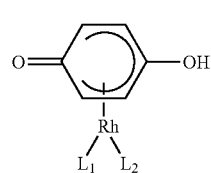

(IV)

wherein $L_1$ and $L_2$ are each a ligand that donates electron density to rhodium to stabilize it;

or formula (V)

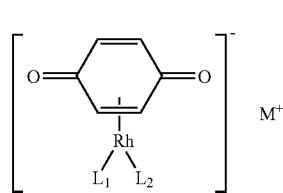

(V)

wherein $L_1$ and $L_2$ are each a ligand that donates electron density to rhodium to stabilize it; and wherein $M^+$ is a positively charged ion including any metal ion having an oxidation state at or higher than +1.

4. A rhodium quinonoid catalyst or catalyst precursor comprising 1,4-hydroquinones π-bonded to rhodium.

5. The catalyst or catalyst precursor of claim 4 comprising [1,4-(hydroquine)Rh(COD)]$^+$ cation, wherein COD is cyclooctadiene.

6. A rhodium quinonoid catalyst or catalyst precursor of comprising 1,3-hydroquinone 71-bonded to rhodium.

7. The catalyst or catalyst precursor of claim 6 comprising [1,3-(hydroquine)Rh(COD)]$^+$ cations.

8. A rhodium quinonoid catalyst or catalyst precursor of claim 1 comprising 1,2-hydroquinone π-bonded to rhodium.

9. A rhodium quinonoid catalyst or catalyst precursor comprising 1,2-hydroquinone, 1,3-hydroquinone or 1,4-hydroquinone π-bonded to Rh(P(OPh)$_3$)$_2^+$ cation.

10. A porous organometallic structure comprising rhodium quinonoid salt [1,4-(hydroquine)Rh(P(OPh)$_3$)$_2$]$^+$X$^-$ (X$^-$=BF$_4^-$, ClO$_4^-$) and [1,3-(hydroquine)Rh(P(OPh)$_3$)$_2$]$^+$ BF$_4^-$.

11. The porous organometallic structure of claim 10 wherein the structure is a porous media for gas storage.

12. A rhodium quinonoid catalyst or catalyst precursor wherein the catalyst comprises an anionic rhodium η$^4$-quinoid complex.

13. The catalyst or catalyst precursor of claim 12 wherein the catalyst is a multifunctional catalyst for the arylation of aldehydes with arylboronic acids and conjugate addition to activated carbon-carbon double bonds with arylboronic acids, wherein both the quinone and the rhodium participate in a catalytic reaction.

14. The catalyst or catalyst precursor of claim 12 wherein the complex comprises η$^6$-hydroquinone complex 1$^+$BF$_4^-$ synthesized by reaction of [Rh(COD)Cl]$_2$ with AgBF$_4$ and hydroquinone.

15. The catalyst of claim 12 wherein the rhodium complex comprises two independent complexes of rhodium with hydroquinone and COD ligands and a $BF_4$ counterion.

16. The catalyst of claim 12 wherein the complex comprises $1^+BF_4^-$ or $2^+BF_4^-$.

17. The catalyst of claim 12 wherein the rhodium complex comprises anionic rhodium $\eta^4$-quinonoid complex 3.K or 3.Li.

18. The catalyst or catalyst precursor of claim 12 wherein the rhodium complex comprises a $\eta^6$-1,4 hydroquinone rhodium complex.

19. A rhodium quinonoid catalyst or catalyst precursor comprising complex [(1,4- and 1,3-hydroquinone)Rh(P(OPh)$_3$)$_2$]BF$_4$(14$^+$BF$_4^-$, 15$^+$BF$_4^-$).

20. A method comprising:
 a) mixing [Rh(COD)Cl]$_2$ and AgBF$_4$ in a solution of methylene chloride and acetone to form a precipitate;
 b) dissolving 1,4-hydroquinone in acetone and adding to a);
 c) followed by removing the solvent wherein a residue remained.

21. A rhodium quinoid complex bridging a lithium alkoxide cubane, wherein a Li$_4$O$_4$ cubane is linked by an organometalloligand [$\eta^4$ quinone)Rh(COD)]$^-$.

22. The complex of claim 21 wherein two Li$_4$O$_4$ cubane units are bridged by a quinone organometalloligand.

23. The complex of claim 22 comprising formula (VI) wherein THF is tetrahydrofuran; COD is cyclooctadiene; and Bu$^t$ is tetramethylmethyl

VI

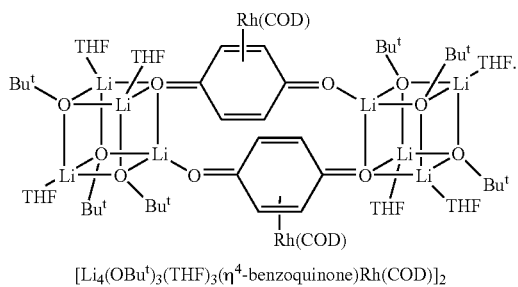

[Li$_4$(OBu$^t$)$_3$(THF)$_3$($\eta^4$-benzoquinone)Rh(COD)]$_2$

24. The rhodium quinonoid catalyst or catalyst precursor of claim 1 wherein the R' substituents are selected from the group consisting of methyl, phenyl, $CF_3$ and combinations thereof.

25. The rhodium quinonoid catalyst or catalyst precursor of claim 3 wherein the R' substituents are selected from the group consisting of methyl, phenyl, $CF_3$ and combinations thereof.

26. The porous organometallic structure of claim 11 wherein the structure is a porous media for hydrogen gas storage.

27. The rhodium quinonoid catalyst or catalyst precursor of claim 1 wherein $L_1$ and $L_2$ are identical or non-identical ligands that are either chiral or achiral and selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitriles, and combinations thereof.

28. The rhodium quinonoid catalyst or catalyst precursor of claim 2 wherein $L_1$ and $L_2$ are identical or non-identical ligands that are either chiral or achiral and selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitriles, and combinations thereof.

29. The rhodium quinonoid catalyst or catalyst precursor of claim 3 wherein M$^+$ is selected from the group consisting of cationic Li, K, Cs, Be, Sr, Ba, Al, Ti, Zr, B, Si, Cd, Ag, Ph$_3$PNPPh$_3$, Rb, Mg$^{2+}$, Ca$^{2+}$, Na, R$_4$N$^+$, Zn$^{2+}$, ammonium salts including tetraalkylammonium cations, tetraalkylarsonium cations, guanidinium salts, amidinium salts, and combinations thereof;

and $L_1$ and $L_2$ are identical or non-identical ligands that are either chiral or achiral and selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitrites, and combinations thereof.

* * * * *

UNITED STATES PATENT AND TRADEMARK OFFICE
CERTIFICATE OF CORRECTION

PATENT NO. : 7,495,097 B2
APPLICATION NO. : 11/454760
DATED : February 24, 2009
INVENTOR(S) : Sweigart et al.

It is certified that error appears in the above-identified patent and that said Letters Patent is hereby corrected as shown below:

Claim 2, column 39, line 22, delete "of".

Claim 6, column 40, line 39, delete "of".

Claim 6, column 40, line 40, delete "71" and replace with --π--.

Claim 8, column 40, lines 43-44, delete "of claim 1".

Signed and Sealed this

Twenty-first Day of July, 2009

JOHN DOLL
*Acting Director of the United States Patent and Trademark Office*